US010738242B2

(12) United States Patent
Kodera et al.

(10) Patent No.: US 10,738,242 B2
(45) Date of Patent: Aug. 11, 2020

(54) COMPOUND, CURED PRODUCT, POLYMER, PHOTO-ALIGNMENT FILM, OPTICALLY ANISOTROPIC BODY AND LIQUID CRYSTAL DISPLAY ELEMENT

(71) Applicant: DIC Corporation, Tokyo (JP)

(72) Inventors: Fumiaki Kodera, Kita-adachi-gun (JP); Yoshitaka Saito, Kita-adachi-gun (JP); Hiroshi Hasebe, Kita-adachi-gun (JP); Masanao Takashima, Kita-adachi-gun (JP); Shuuhei Yamamoto, Kita-adachi-gun (JP); Kouzi Satou, Kita-adachi-gun (JP); Sayaka Nose, Kita-adachi-gun (JP); Kazuki Obi, Kita-adachi-gun (JP); Hiroyuki Itou, Kita-adachi-gun (JP)

(73) Assignee: DIC CORPORATION, Tokyo (JP)

( * ) Notice: Subject to any disclaimer, the term of this patent is extended or adjusted under 35 U.S.C. 154(b) by 126 days.

(21) Appl. No.: 15/954,045

(22) Filed: Apr. 16, 2018

(65) Prior Publication Data

US 2018/0230385 A1 Aug. 16, 2018

Related U.S. Application Data

(63) Continuation of application No. PCT/JP2016/079761, filed on Oct. 6, 2016.

(30) Foreign Application Priority Data

Oct. 16, 2015 (JP) ................................ 2015-204830

(51) Int. Cl.

| | |
|---|---|
| ***G02F 1/1333*** | (2006.01) |
| ***C09K 19/56*** | (2006.01) |
| ***C09K 19/24*** | (2006.01) |
| ***C07C 245/08*** | (2006.01) |
| ***C08F 220/30*** | (2006.01) |
| ***C08F 222/20*** | (2006.01) |
| *C08F 220/34* | (2006.01) |
| *C09K 19/04* | (2006.01) |
| *G02F 1/1337* | (2006.01) |

(52) U.S. Cl.

CPC ............ *C09K 19/56* (2013.01); *C07C 245/08* (2013.01); *C08F 220/30* (2013.01); *C08F 222/20* (2013.01); *C09K 19/24* (2013.01); *C08F 220/303* (2020.02); *C08F 220/34* (2013.01); *C09K 2019/0448* (2013.01); *G02F 1/133711* (2013.01); *G02F 1/133788* (2013.01)

(58) Field of Classification Search

CPC .................................................... C09K 19/56; C09K 19/24; C09K 2019/0448; G02F 1/1333; G02F 1/133711; G02F 1/133788; C07C 245/08; C08F 220/30; C08F 220/34; C08F 222/20; C08F 2220/303

USPC ......................................................... 526/299

See application file for complete search history.

(56) References Cited

U.S. PATENT DOCUMENTS

2018/0230385 A1* 8/2018 Kodera ................ C08F 220/34

* cited by examiner

*Primary Examiner* — Geraldina Visconti

(74) *Attorney, Agent, or Firm* — Westerman, Hattori, Daniels & Adrian, LLP

(57) ABSTRACT

A compound and a polymer which can each form a photo-alignment film having excellent ability of controlling alignment, a photo-alignment film obtained using the polymer and an optically anisotropic body and a liquid crystal display element each having the photo-alignment film are provided. A compound represented by the general formula (1). In the formula, P represents a polymerizable group, Z and $Z^1$ represent divalent linking groups, A and $A^1$ represent divalent cyclic groups, and $X^1$ to $X^5$ each independently represent a hydrogen atom, a fluorine atom, a chlorine atom, a hydroxy group, a nitro group, a cyano group or an alkyl group having 1 to 40 carbon atoms which may have a substituent, provided that $X^1$, $X^2$, $X^4$ and $X^5$ are not simultaneously hydrogen atoms.

(1)

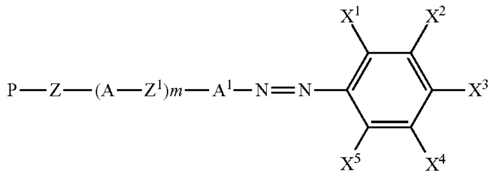

21 Claims, No Drawings

COMPOUND, CURED PRODUCT, POLYMER, PHOTO-ALIGNMENT FILM, OPTICALLY ANISOTROPIC BODY AND LIQUID CRYSTAL DISPLAY ELEMENT

TECHNICAL FIELD

The present invention relates to a compound, a cured product, a polymer, a photo-alignment film, an optically anisotropic body and a liquid crystal display element.

BACKGROUND ART

Photo-alignment films have excellent characteristics, namely, the films are free of very small scratches introduced by mechanical rubbing, dusting due to rubbing, and the risk of breaking of a TFT element, which may accompany the dusting, and enable high-definition patterning. For this reason, the films have been applied energetically to various liquid crystal displays. The demand for photo-alignment films for the horizontal alignment (planar alignment) used for IPS/FFS displays is particularly enormous.

In a general method for producing a photo-alignment film without a rubbing treatment, a solution containing a photo-alignment polymer is first applied onto a substrate to form a dried coating film, and then the ability of controlling the alignment of liquid crystals is given to the surface of the photo-alignment film by applying polarized light to the coating film (for example, see PTL 1).

CITATION LIST

Patent Literature

[PTL 1] WO2013/002260

SUMMARY OF INVENTION

Technical Problem

When a photo-alignment film having poor ability of controlling alignment is used for a liquid crystal display element, a problem called AC burn-in is caused. AC burn-in is a defective mode which is caused because the alignment of liquid crystal molecules does not completely return to the alignment direction determined by the photo-alignment film even when the liquid crystal molecules are returned to a state without voltage application after the liquid crystal molecules are kept in a state where a voltage is applied. Because AC burn-in causes a serious decrease in the contrast, a photo-alignment film which is unlikely to cause AC burn-in is greatly to be desired.

To meet the demand, a photo-alignment polymer having a cinnamic acid derivative and an azobenzene derivative in the side chains as photo-alignment side-chain units is disclosed in PTL 1. Excellent ability of controlling alignment is obtained through dimerization of the cinnamic acid derivative due to polarized ultraviolet rays, and, at the same time, the azobenzene increases the sensitivity to polarized ultraviolet rays and reduces the irradiation period. In PTL 1, a photo-alignment film obtained using a polymer having a side-chain unit in which only the para-position of the azobenzene is substituted is investigated for the purpose of enhancing the ability of controlling alignment and the like.

However, the ability of controlling alignment is not satisfactory, and a photo-alignment film which exhibits superior ability of controlling alignment and a photo-alignment polymer as the material for the film have been required.

The invention has been made under the circumstances and provides a compound, a cured product and a polymer which can each form a photo-alignment film having excellent ability of controlling alignment, a photo-alignment film obtained using the polymer and an optically anisotropic body and a liquid crystal display element each having the photo-alignment film.

Solution to Problem

A first embodiment of the invention is a compound represented by the following general formula (1):

[Chem. 1]

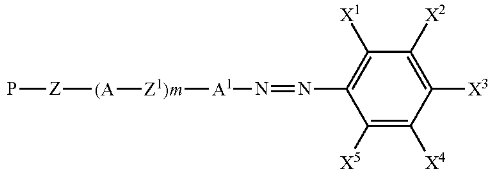

(1)

(in the formula (1),

P represents a polymerizable group,

A and $A^1$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein A and $A^1$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2$O—, —O$CF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$ to $X^5$ each independently represent a hydrogen atom, a fluorine atom, a chlorine atom, a hydroxy group, a nitro group, a cyano group or the following formula (G):

[Chem. 2]

$$-A^{2}\text{-}(Z_2\text{-}A_3)_n\text{-}R \qquad (G)$$

in the formula (G), $A^2$ and $A^3$ each independently represent a single bond, a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein $A^2$ and $A^3$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$, $X^2$, $X^4$ and $X^5$ are not simultaneously hydrogen atoms, Z, $Z^1$ and $Z^2$ each independently represent a single bond or a linear or branched alkylene group having 1 to 40 carbon atoms, wherein one or more non-adjacent —$CH_2$—'s in the alkylene group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms on the —$CH_2$—'s in the alkylene group may be substituted with a fluorine atom, a chlorine atom, a hydroxy group or a cyano group, m and n each independently represent 0 or 1, and R represents a hydrogen atom or a linear or branched alkyl group having 1 to 40 carbon atoms, wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the —$CH_2$—'s in the alkyl group having 1 to 40 carbon atoms may be substituted with a fluorine atom, a chlorine atom, a hydroxy group or a cyano group, with the proviso that R is not a hydrogen atom when n is 0 and $A^2$ is a single bond).

A second embodiment of the invention is a polymer having one or more kinds of side-chain unit represented by the following general formula (2):

[Chem. 3]

(2)

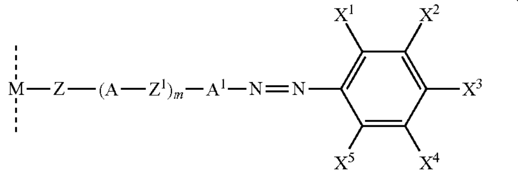

(in the formula (2), the broken line represents the main chain of the polymer, M represents a monomer unit of the polymer, A and $A^1$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein A and $A^1$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$ to $X^5$ each independently represent a hydrogen atom, a fluorine atom, a chlorine atom, a hydroxy group, a nitro group, a cyano group or the following formula (G):

[Chem. 4]

$$-A^2\text{-}(Z^2\text{-}A^3)_n\text{-}R \qquad (G)$$

in the formula (G), $A^2$ and $A^3$ each independently represent a single bond, a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein $A^2$ and $A^3$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$, $X^2$, $X^4$ and $X^5$ are not simultaneously hydrogen atoms, Z, $Z^1$ and $Z^2$ each independently represent a single bond or a linear or branched alkylene group having 1 to 40 carbon atoms, wherein one or more non-adjacent —$CH_2$—'s in the alkylene group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—Si$(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the —$CH_2$—'s in the alkylene group may be substituted with a fluorine atom, a chlorine atom, a hydroxy group or a cyano group, m and n each independently represent 0 or 1, and R represents a hydrogen atom or a linear or branched alkyl group having 1 to 40 carbon atoms, wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the —$CH_2$—'s in the alkyl group having 1 to 40 carbon atoms may be substituted with a fluorine atom, a chlorine atom, a hydroxy group or a cyano group, with the proviso that R is not a hydrogen atom when n is 0 and $A^2$ is a single bond).

A third embodiment of the invention is a cured product obtained by polymerizing the compound of the first embodiment.

A fourth embodiment of the invention is a photo-alignment film containing any of the compound of the first embodiment, the polymer of the second embodiment and the cured product of the third embodiment.

A fifth embodiment of the invention is an optically anisotropic body having the photo-alignment film of the fourth embodiment.

A sixth embodiment of the invention is a liquid crystal display element having the photo-alignment film of the fourth embodiment.

Advantageous Effects of Invention

Using the polymer of the invention, a photo-alignment film having excellent ability of controlling alignment is obtained. A film obtained by casting this polymer is highly sensitive to a polarized ultraviolet ray, and thus a photo-alignment film having excellent ability of controlling alignment is obtained by a small amount of light irradiation. As a result, when the photo-alignment film according to the invention is used, a liquid crystal display element having excellent display picture quality can be produced with short takt time. Moreover, because the photo-alignment film of the invention has excellent liquid crystal alignment property, AC burn-in of a liquid crystal display element having the photo-alignment film can be reduced.

DESCRIPTION OF EMBODIMENTS

The invention is explained below based on preferable embodiments, but the invention is not limited to the embodiments.

<<Compound>>

The first embodiment of the invention is a compound represented by the following general formula (1), which is sometimes called a compound (1) below.

[Chem. 5]

(1)

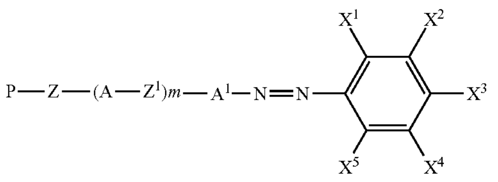

(In the formula (1),

P represents a polymerizable group,

A and $A^1$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein A and $A^1$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$ to $X^5$ each independently represent a hydrogen atom, a fluorine atom, a chlorine atom, a hydroxy group, a nitro group, a cyano group or the following formula (G):

[Chem. 6]

$$-A^2-(Z^2-A^3)_n-R \quad (G)$$

in the formula (G), $A^2$ and $A^3$ each independently represent a single bond, a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, wherein $A^2$ and $A^3$ are unsubstituted, or one or more hydrogen atoms may be substituted with a fluorine atom, a chlorine atom or a linear or branched alkyl group having 1 to 20 carbon atoms (one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —Si$(CH_3)_2$—O—$Si(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the alkyl group having 1 to 20 carbon atoms may be substituted with a fluorine atom, a chlorine atom, a hydroxy group or a cyano group), $X^1$, $X^2$, $X^4$ and $X^5$ are not simultaneously hydrogen atoms, Z, $Z^1$ and $Z^2$ each independently represent a single bond or a linear or branched alkylene group having 1 to 40 carbon atoms, wherein one or more non-adjacent —$CH_2$—'s in the alkylene group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the —$CH_2$—'s in the alkylene group may be substituted with a fluorine atom, a chlorine atom, a hydroxy group or a cyano group, m and n each independently represent 0 or 1, and R represents a hydrogen atom or a linear or branched alkyl group having 1 to 40 carbon atoms, wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent a hydrogen atom or an alkyl group having 1 to 5 carbon atoms), and one or more hydrogen atoms of the —$CH_2$—'s in the alkyl group having 1 to 40 carbon atoms may be substituted with a fluorine atom, a chlorine atom, a hydroxy group or a cyano group, with the proviso that R is not a hydrogen atom when n is 0 and $A^2$ is a single bond.)

The polymerizable group P represented by P in the formula (1) is not particularly limited, and same polymerizable groups as those of the polymer materials of conventional photo-alignment films can be used. Examples thereof include known polymerizable groups which can form at least one polymer main chain selected from the group consisting of polyolefins, polyethers, polyamides, polyesters, polycarbonates and polysiloxanes. Of the examples, polyolefins, polyethers, polyamides and polyesters, which are more suitable for the formation of a photo-alignment film, are preferable, and polyolefins are more preferable. In the present description, a polymerizable group which can form a polyolefin (an olefinic polymerizable group) means a group containing a polymerizable vinyl group, and examples thereof are groups which can form polymethacrylate, polyacrylate, polyvinyl, polymethacrylamide, polyacrylamide, polyvinylacetamide or the like.

The polymerizable group P in the formula (1) is preferably a polymerizable group represented by any of the following formulae (III-1) to (III-17), more preferably an olefinic polymerizable group represented by any of the following formulae (III-1) to (III-8), further preferably an acrylic polymerizable group represented by any of the following formulae (III-1) to (III-5).

[Chem. 7]

(III-1)

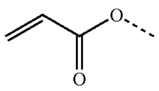

(III-2)

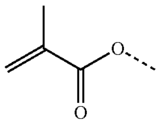

(III-3)

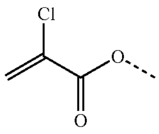

(III-4)

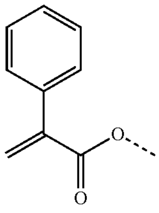

-continued (III-5)

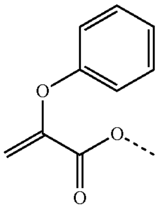

(III-6)

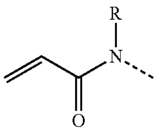

(III-7)

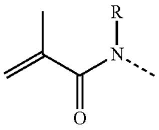

(III-8)

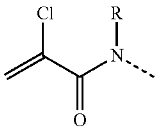

(III-9)

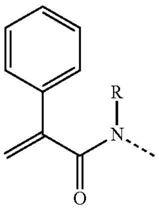

(III-10)

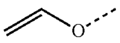

(III-11)

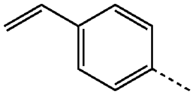

(III-12)

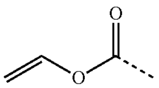

(III-13)

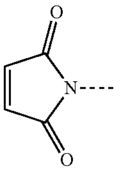

(III-14)

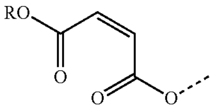

(III-15)

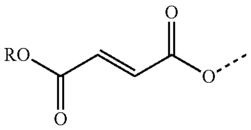

(III-16)

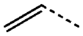

-continued (III-17)

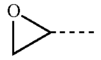

(In the formulae, the broken lines represent bonds to Z, and R's independently represent hydrogen or an alkyl group having 1 to 5 carbon atoms.)

In the general formula (1), Z is preferably a linear alkylene group. The number of the carbon atoms of the alkylene group is preferably 2 to 12, more preferably 3 to 9.

Because the solubility of the polymer of the invention improves, one or more non-adjacent $—CH_2—$ groups in the alkylene group are preferably independently substituted with —O—, —COO— or —OCO—.

In the general formula (1), m is preferably 0.

A and $A^1$ in the general formula (1) are preferably each independently a trans-, 4-cyclohexylene group, a 1,4-naphthylene group, a 2,6-naphthylene group, a 2,5-furanylene group, a pyrimidine-2,5-diyl group or a 1,4-phenylene group. Of the groups, a 1,4-phenylene group is more preferable because the solubility of the polymer of the invention improves.

$Z^1$ in the general formula (1) is preferably a single bond, —COO—, —OCO—, $—OCH_2—$, $—CH_2O—$, $—CF_2O—$, $—OCF_2—$, $—CF_2CF_2—$, —NR—, —CO— or —C≡C—. Of these, $—OCH_2—$, $—CH_2O—$, $—CF_2O—$, $—OCF_2—$, $—CF_2CF_2—$, —NR— or —CO— is more preferable because the solubility of the polymer of the invention improves. Moreover, because the ability of controlling alignment of the invention is enhanced, a single bond, —COO—, —OCO—, $—CF_2O—$ or $—OCF_2—$ is more preferable, and a single bond, —COO— or —OCO— is further preferable.

In the general formula (1), the combination of $—Z-(A-Z^1)_m—$ is preferably, for example, one represented by any of the chemical formula (Sp-a-1) to the chemical formula (Sp-ah1-8) below. In each of the chemical formulae, the broken line on the left represents the bond to the polymerizable group P, and the broken line on the right represents the bond to $A^1$.

Although the combination can be selected according to the need, of these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-l-13) to (Sp-l-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9) and the chemical formulae (Sp-aa-1) to (Sp-aa-9) are more preferable.

[Chem. 8]

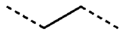
(Sp-a-1)

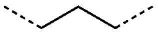
(Sp-a-2)

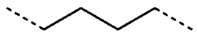
(Sp-a-3)

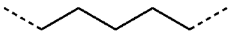
(Sp-a-4)

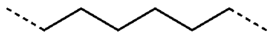
(Sp-a-5)

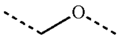
(Sp-a-6)

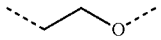
(Sp-a-7)

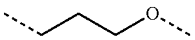
(Sp-a-8)

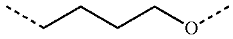
(Sp-a-9)

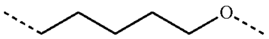
(Sp-a-10)

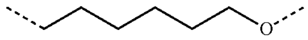
(Sp-a-11)

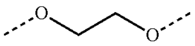
(Sp-a-12)

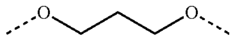
(Sp-a-13)

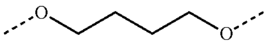
(Sp-a-14)

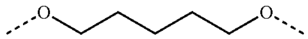
(Sp-a-15)

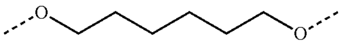
(Sp-a-16)

[Chem. 9]

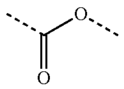
(Sp-b-1)

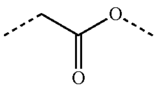
(Sp-b-2)

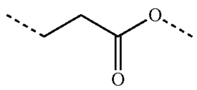
(Sp-b-3)

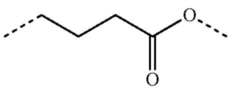
(Sp-b-4)

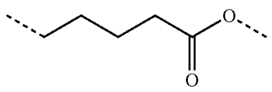
(Sp-b-5)

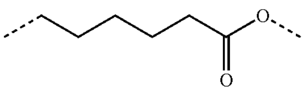
(Sp-b-6)

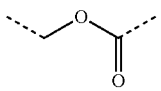
(Sp-b-7)

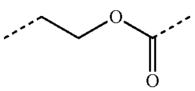
(Sp-b-8)

-continued
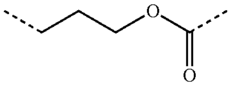
(Sp-b-9)
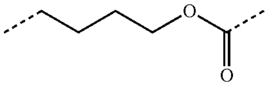
(Sp-b-10)
[Chem. 10]
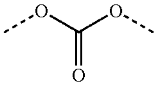
(Sp-c-1)
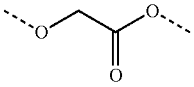
(Sp-c-2)
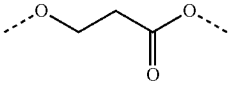
(Sp-c-3)
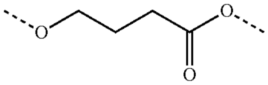
(Sp-c-4)
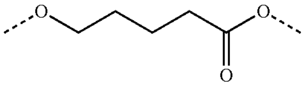
(Sp-c-5)
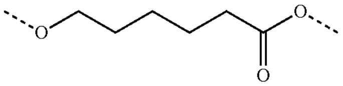
(Sp-c-6)
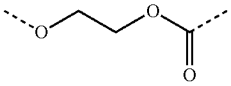
(Sp-c-7)
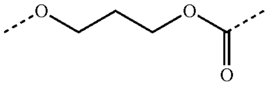
(Sp-c-8)
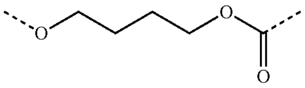
(Sp-c-9)
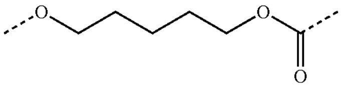
(Sp-c-10)
[Chem. 11]
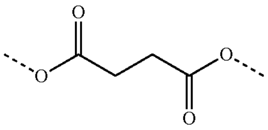
(Sp-d-1)
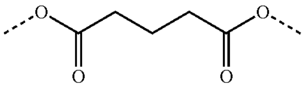
(Sp-d-2)
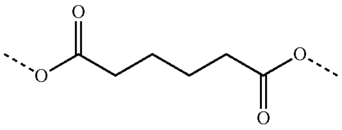
(Sp-d-3)
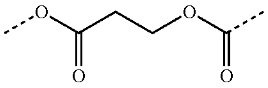
(Sp-d-4)
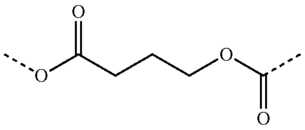
(Sp-d-5)
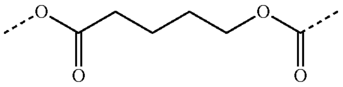
(Sp-d-6)
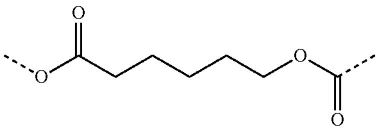
(Sp-d-7)
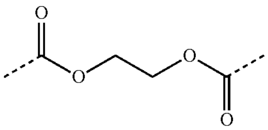
(Sp-d-8)
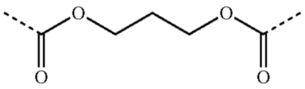
(Sp-d-9)
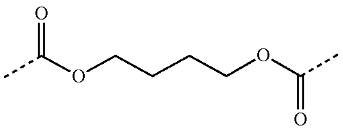
(Sp-d-10)
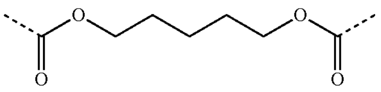
(Sp-d-11)
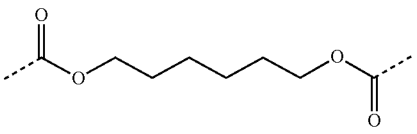
(Sp-d-12)

-continued
[Chem. 12]
(Sp-e-1)
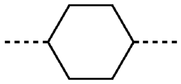
(Sp-e-2)
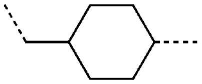
(Sp-e-3)
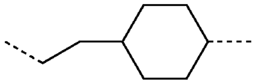
(Sp-e-4)
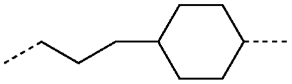
(Sp-e-5)
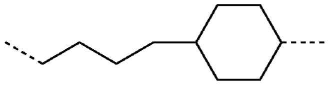
(Sp-e-6)
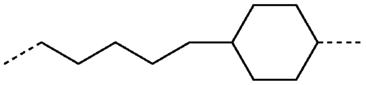
(Sp-e-7)
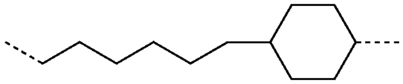
(Sp-e-8)
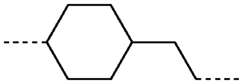
(Sp-e-9)
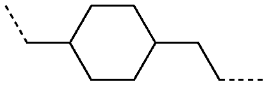
(Sp-e-10)
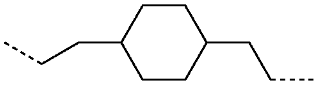
(Sp-e-11)
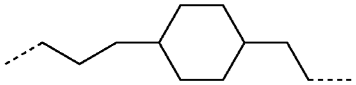
(Sp-e-12)
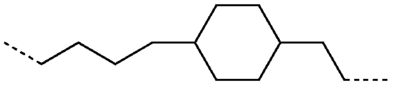
(Sp-e-13)
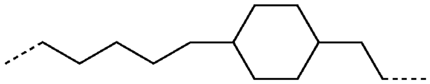
(Sp-e-14)
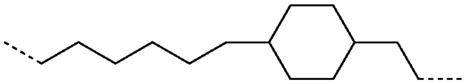
[Chem. 13]
(Sp-f-1)
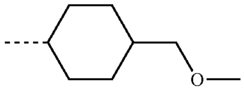
(Sp-f-2)
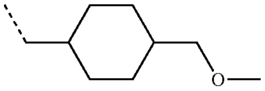
(Sp-f-3)
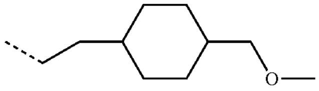
(Sp-f-4)
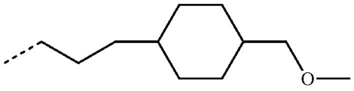
(Sp-f-5)
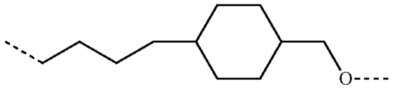
(Sp-f-6)
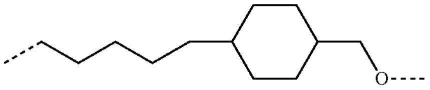
(Sp-f-7)
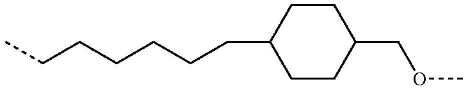
[Chem. 14]
(Sp-g-1)
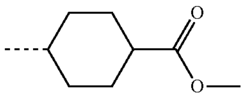
(Sp-g-2)
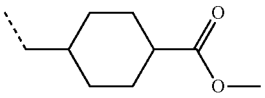
(Sp-g-3)
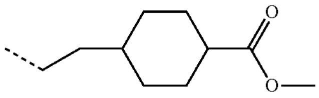
(Sp-g-4)
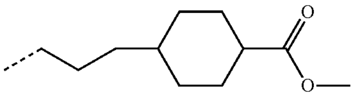
(Sp-g-5)
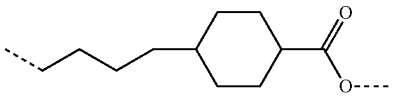
(Sp-g-6)
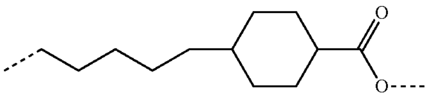

-continued
(Sp-g-7)
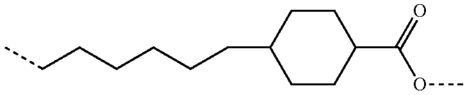
[Chem. 15]
(Sp-h-1)
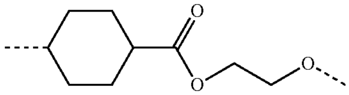
(Sp-h-2)
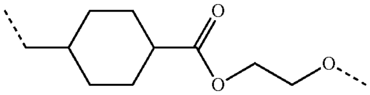
(Sp-h-3)
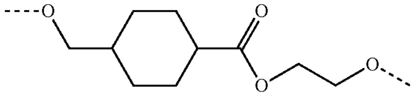
(Sp-h-4)
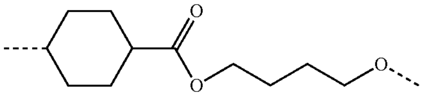
(Sp-h-5)
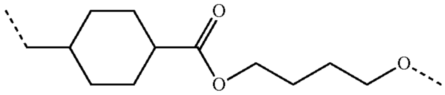
(Sp-h-6)
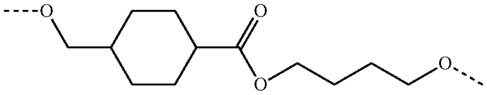
(Sp-h-7)
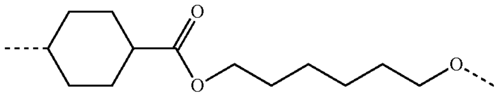
(Sp-h-8)
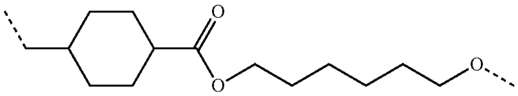
(Sp-h-9)
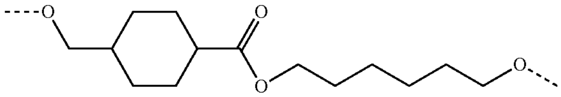
[Chem. 16]
(Sp-i-1)
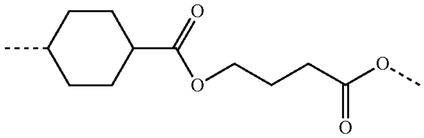
(Sp-i-2)
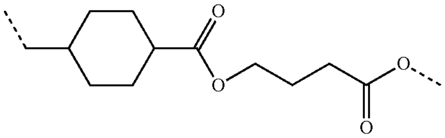
(Sp-i-3)
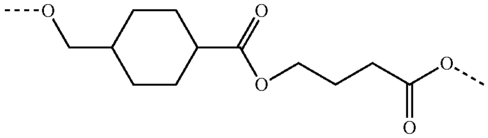
(Sp-i-4)
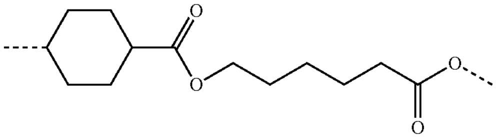
(Sp-i-5)
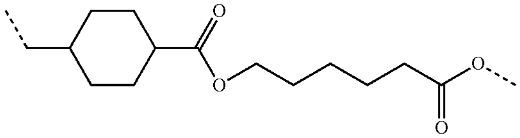
(Sp-i-6)
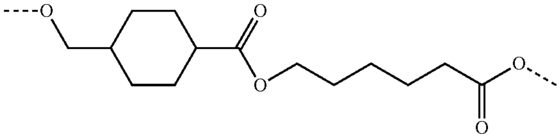
[Chem. 17]
(Sp-j-1)
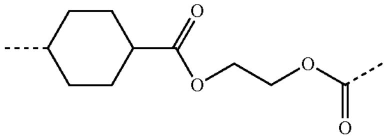
(Sp-j-2)
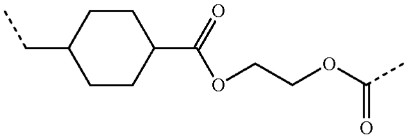
(Sp-j-3)
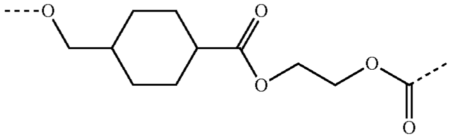
(Sp-j-4)
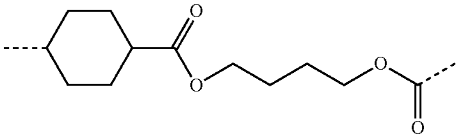

-continued
(Sp-j-5)
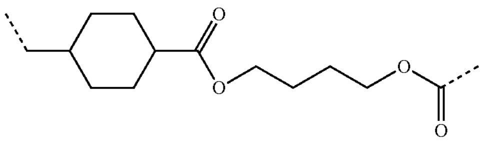
(Sp-j-6)
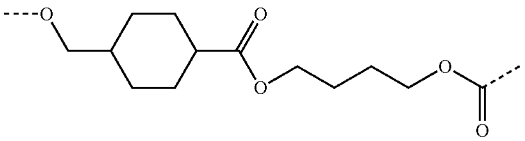
(Sp-j-7)
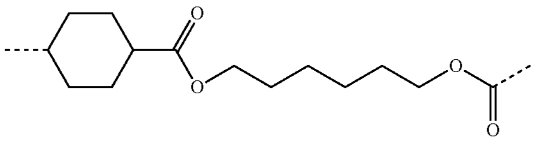
(Sp-j-8)
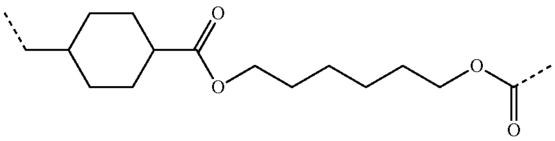
(Sp-j-9)
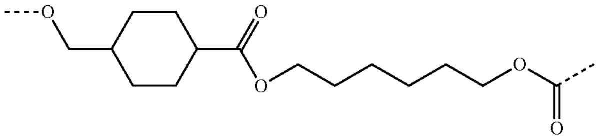
[Chem. 18]
(Sp-k-1)
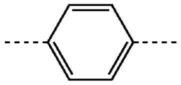
(Sp-k-2)
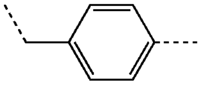
(Sp-k-3)
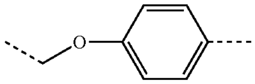
(Sp-k-4)
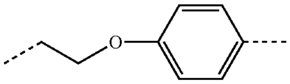
(Sp-k-5)
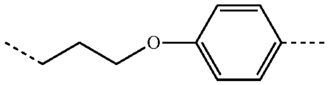
(Sp-k-6)
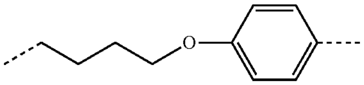
(Sp-k-7)
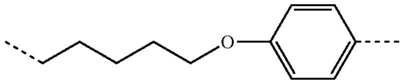
(Sp-k-8)
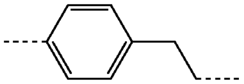
(Sp-k-9)
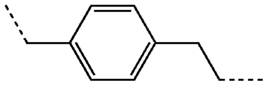
(Sp-k-10)
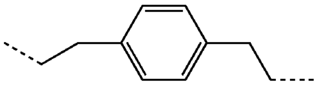
(Sp-k-11)
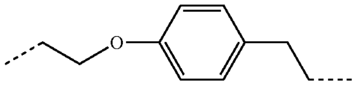
(Sp-k-12)
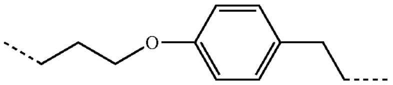
(Sp-k-13)
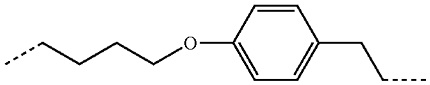
(Sp-k-14)
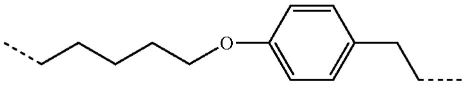
[Chem. 19]
(Sp-l-1)
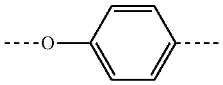
(Sp-l-2)
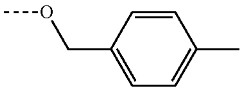
(Sp-l-3)
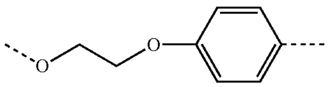
(Sp-l-4)
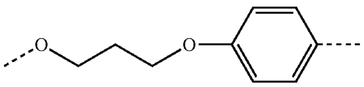
(Sp-l-5)
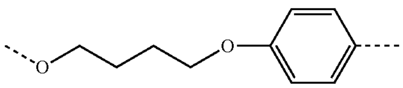
(Sp-l-6)
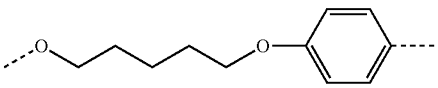

-continued
(Sp-l-7)
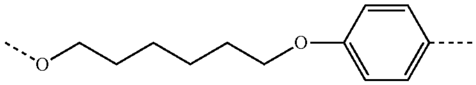
(Sp-l-8)
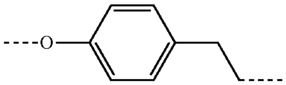
(Sp-l-9)
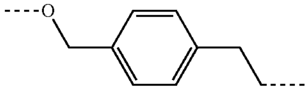
(Sp-l-10)
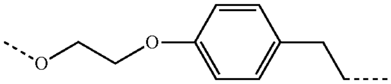
(Sp-l-11)
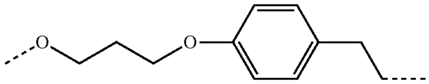
(Sp-l-12)
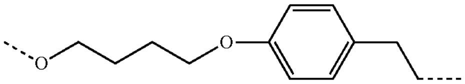
(Sp-l-13)
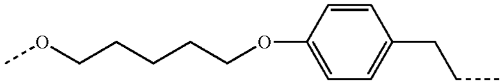
(Sp-l-14)
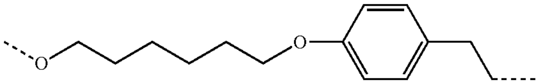
[Chem. 20]
(Sp-m-1)
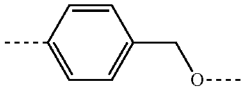
(Sp-m-2)
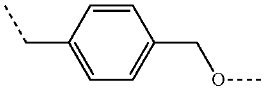
(Sp-m-3)
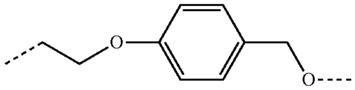
(Sp-m-4)
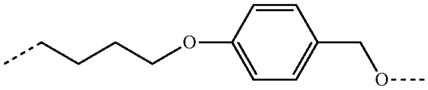
(Sp-m-5)
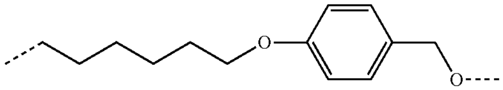
(Sp-m-6)
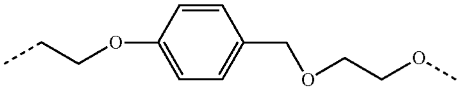
(Sp-m-7)
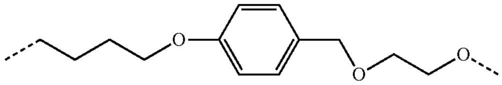
(Sp-m-8)
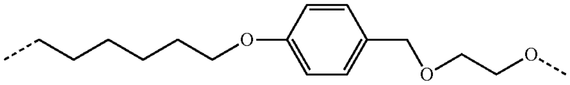
(Sp-m-9)
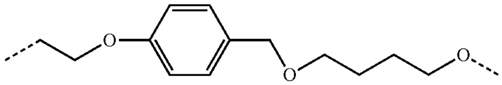
(Sp-m-10)
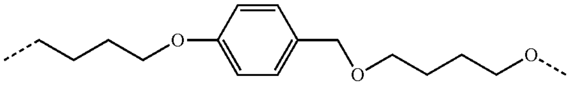
(Sp-m-11)
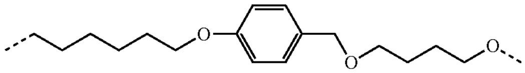
(Sp-m-12)
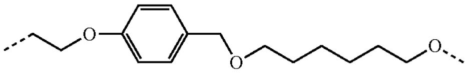
(Sp-m-13)
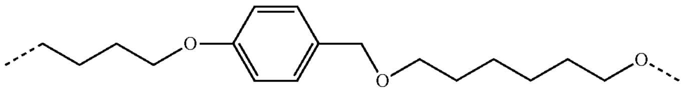
(Sp-m-14)
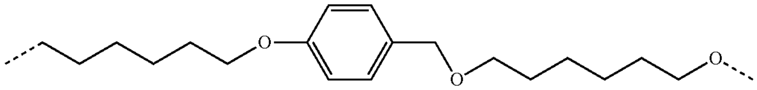
[Chem. 21]
(Sp-n-1)
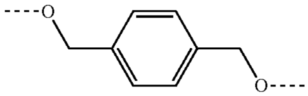
(Sp-n-2)
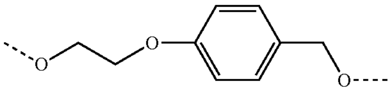

-continued
(Sp-n-3)
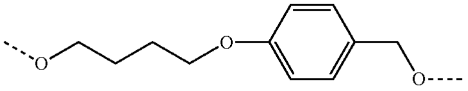
(Sp-n-4)
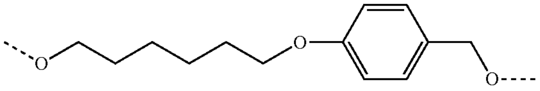
(Sp-n-5)
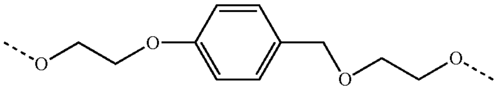
(Sp-n-6)
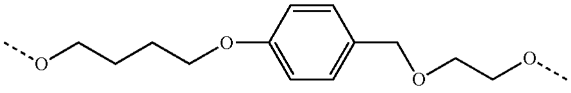
(Sp-n-7)
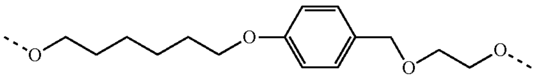
(Sp-n-8)
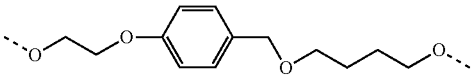
(Sp-n-9)
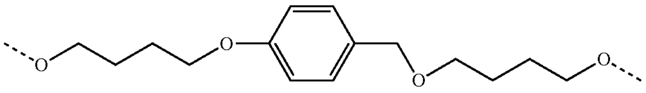
(Sp-n-10)
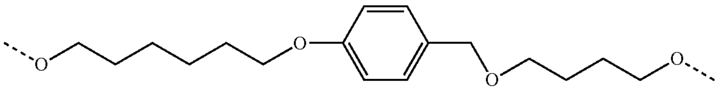
(Sp-n-11)
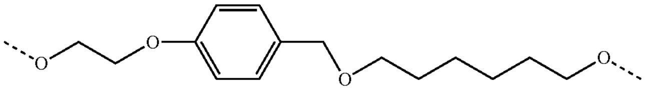
(Sp-n-12)
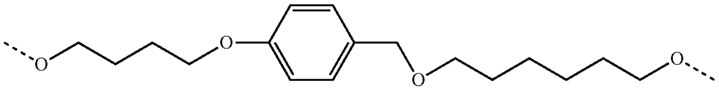
(Sp-n-13)
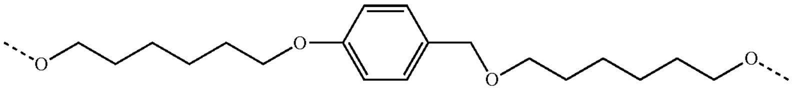
[Chem. 22]
(Sp-o-1)
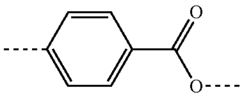
(Sp-o-2)
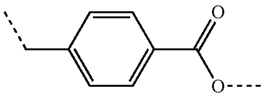
(Sp-o-3)
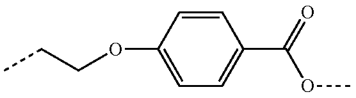
(Sp-o-4)
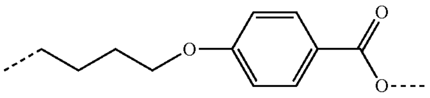
(Sp-o-5)
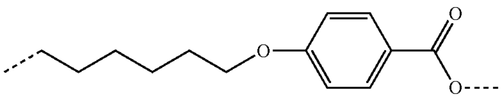
(Sp-o-6)
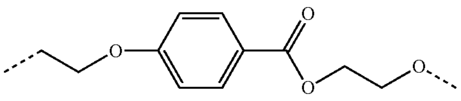
(Sp-o-7)
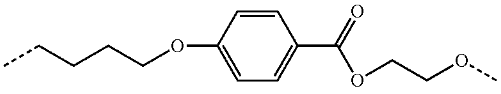
(Sp-o-8)
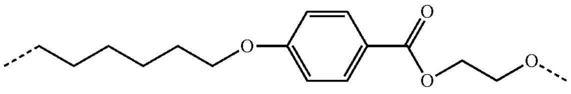
(Sp-o-9)
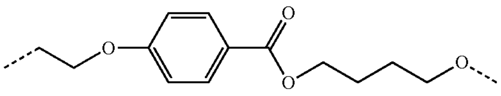
(Sp-o-10)
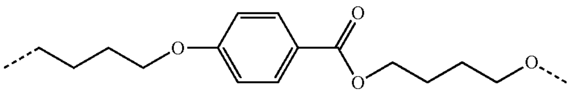

-continued
(Sp-o-11)
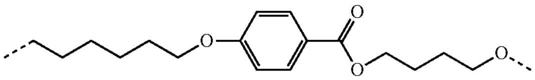
(Sp-o-12)
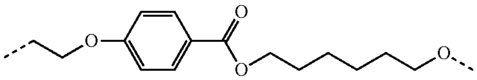
(Sp-o-13)
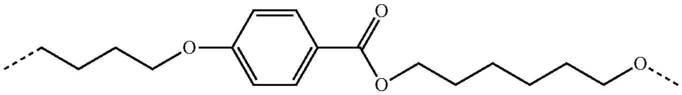
(Sp-o-14)
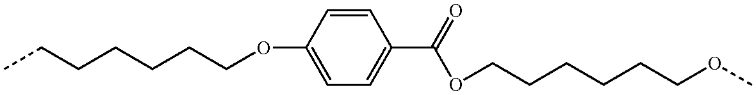
[Chem. 23]
(Sp-p-1)
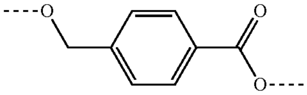
(Sp-p-2)
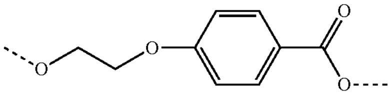
(Sp-p-3)
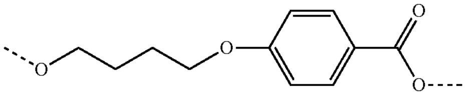
(Sp-p-4)
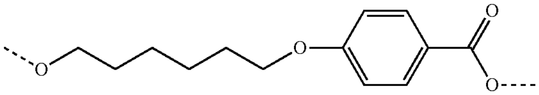
(Sp-p-5)
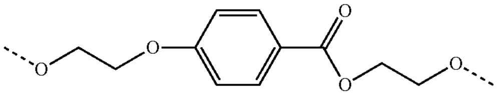
(Sp-p-6)
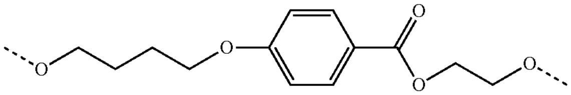
(Sp-p-7)
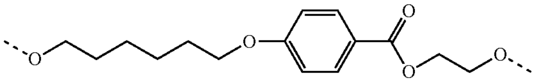
(Sp-p-8)
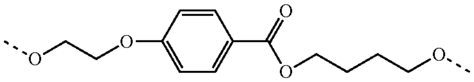
(Sp-p-9)
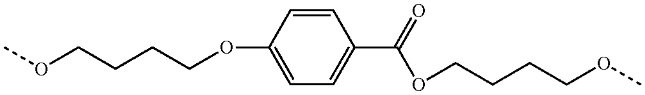
(Sp-p-10)
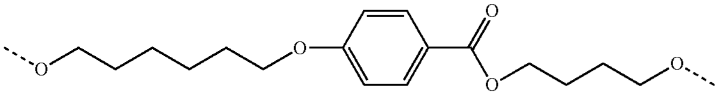
(Sp-p-11)
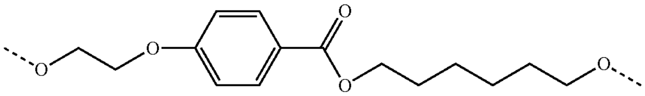
(Sp-p-12)
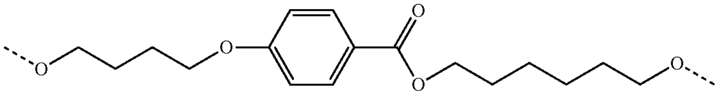
(Sp-p-13)
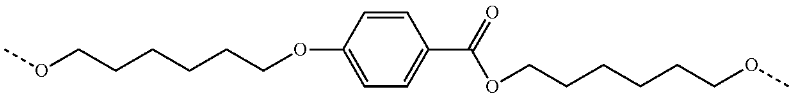
[Chem. 24]
(Sp-q-1)
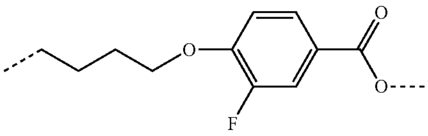
(Sp-q-2)
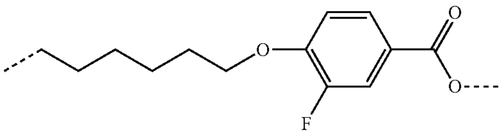

-continued
(Sp-q-3)
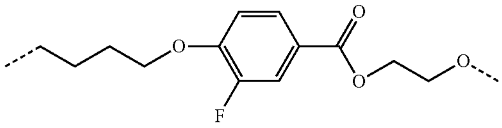
(Sp-q-4)
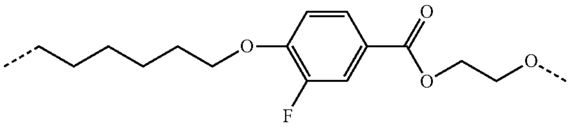
(Sp-q-5)
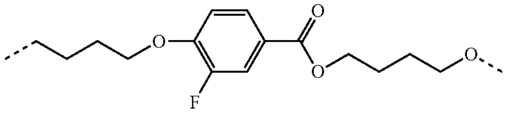
(Sp-q-6)
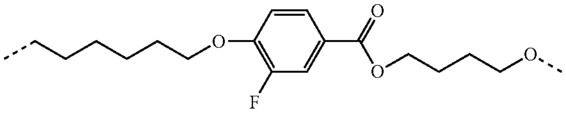
(Sp-q-7)
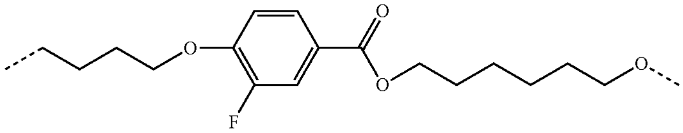
(Sp-q-8)
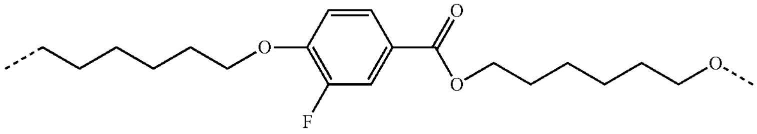
[Chem. 25]
(Sp-r-1)
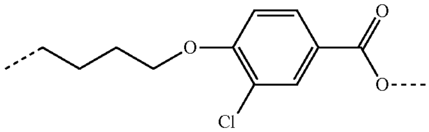
(Sp-r-2)
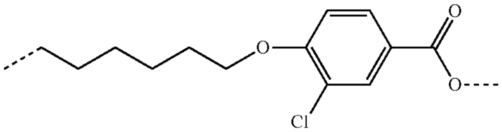
(Sp-r-3)
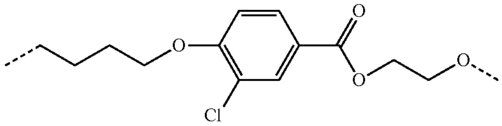
(Sp-r-4)
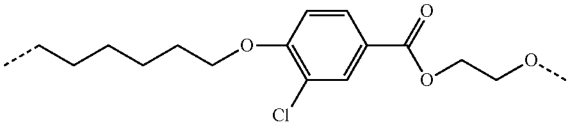
(Sp-r-5)
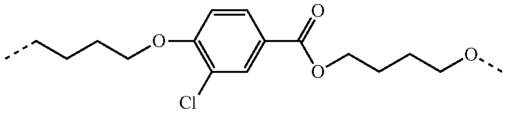
(Sp-r-6)
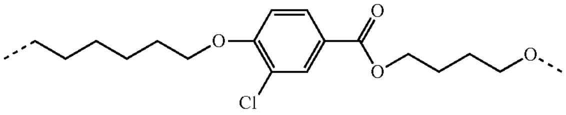
(Sp-r-7)
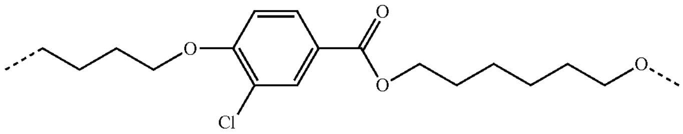
(Sp-r-8)
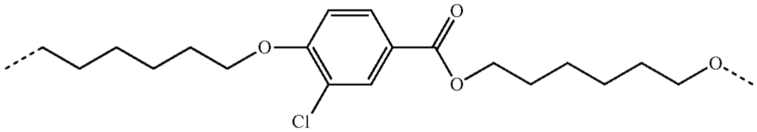
[Chem. 26]
(Sp-s-1)
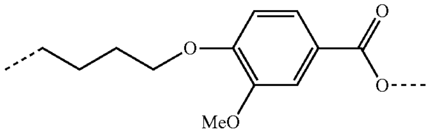
(Sp-s-2)
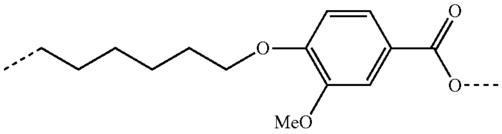

-continued
(Sp-s-3)
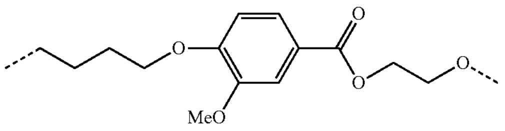
(Sp-s-4)
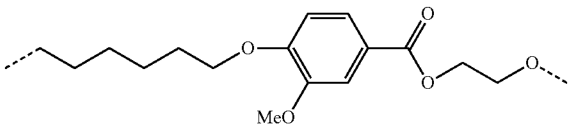
(Sp-s-5)
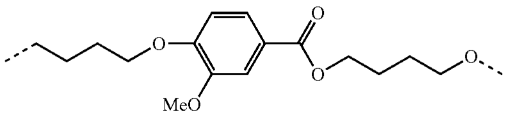
(Sp-s-6)
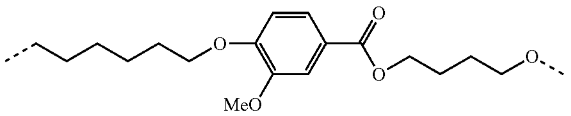
(Sp-s-7)
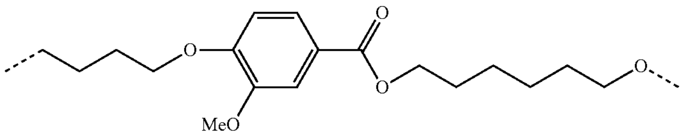
(Sp-s-8)
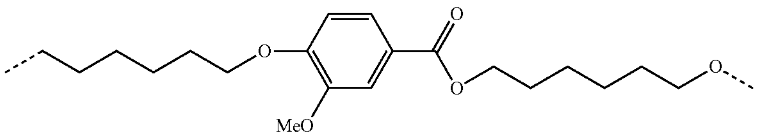
[Chem. 27]
(Sp-t-1)
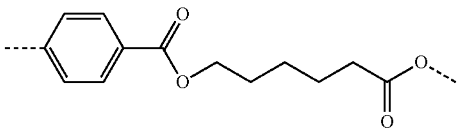
(Sp-t-2)
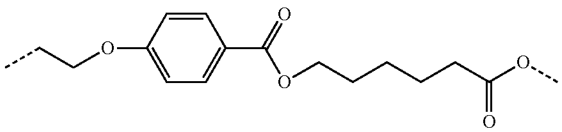
(Sp-t-3)
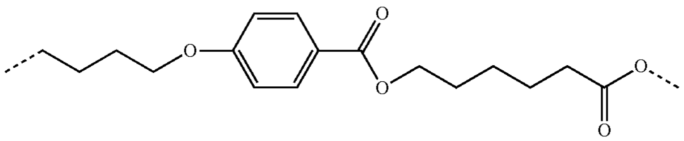
(Sp-t-4)
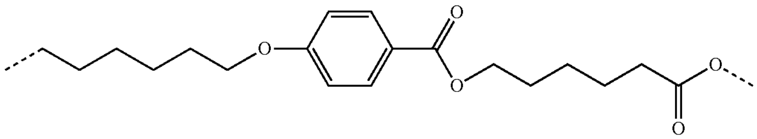
(Sp-t-5)
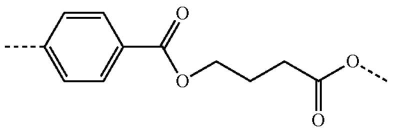
(Sp-t-6)
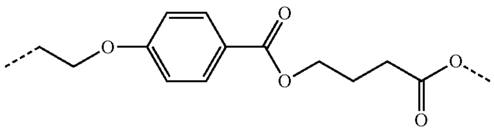
(Sp-t-7)
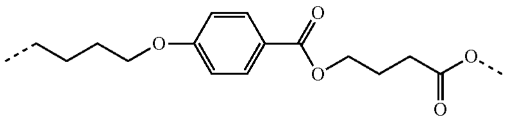
(Sp-t-8)
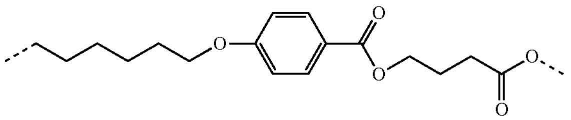
[Chem. 28]
(Sp-u-1)
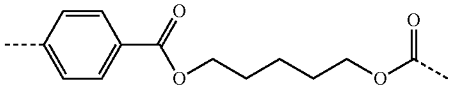
(Sp-u-2)
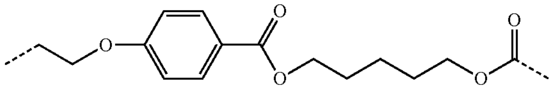

-continued
(Sp-u-3)
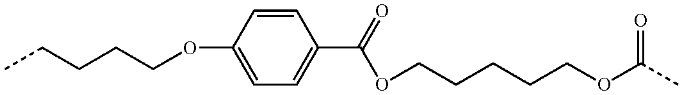
(Sp-u-4)
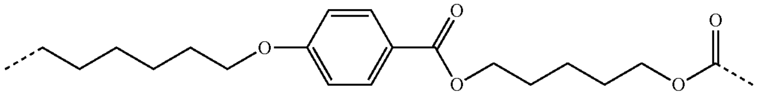
(Sp-u-5)
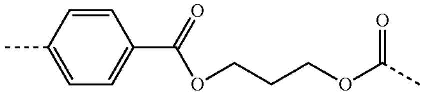
(Sp-u-6)
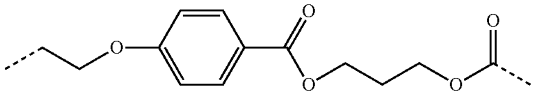
(Sp-u-7)
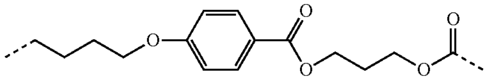
(Sp-u-8)
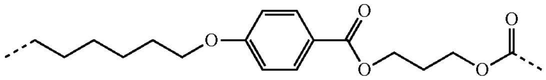
[Chem. 29]
(Sp-v-1)
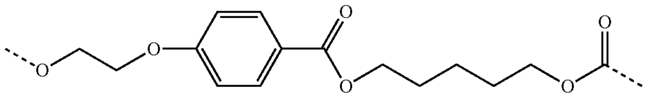
(Sp-v-2)
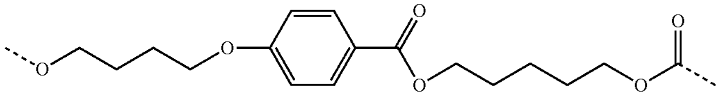
(Sp-v-3)
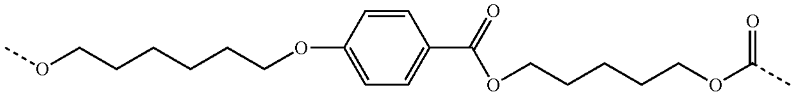
(Sp-v-4)
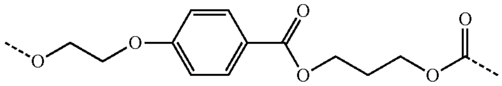
(Sp-v-5)
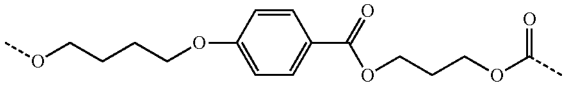
(Sp-v-6)
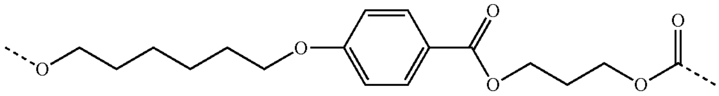
[Chem. 30]
(Sp-w-1)
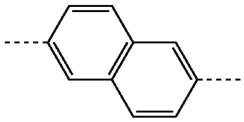
(Sp-w-2)
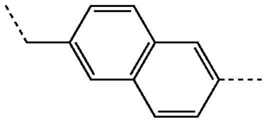
(Sp-w-3)
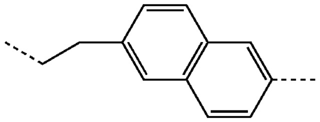
(Sp-w-4)
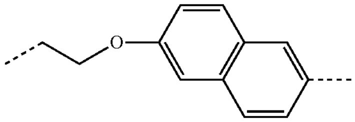
(Sp-w-5)
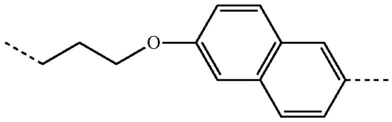
(Sp-w-6)
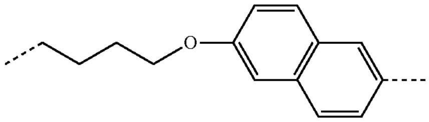

-continued
(Sp-w-7)
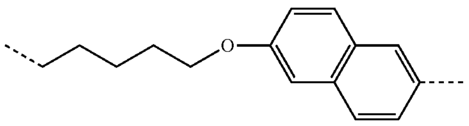
(Sp-w-8)
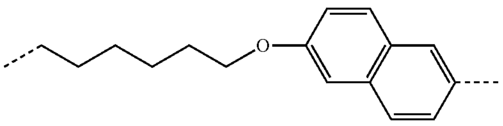
[Chem. 31]
(Sp-x-1)
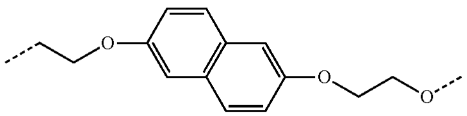
(Sp-x-2)
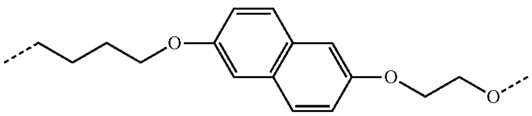
(Sp-x-3)
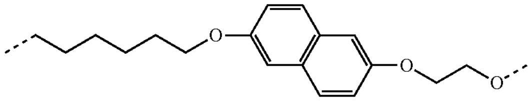
(Sp-x-4)
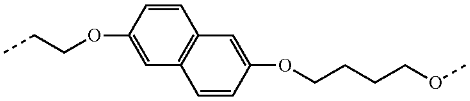
(Sp-x-5)
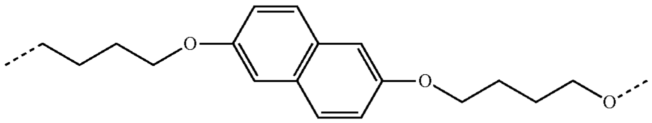
(Sp-x-6)
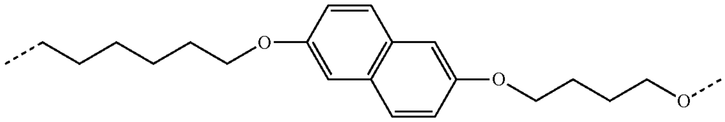
(Sp-x-7)
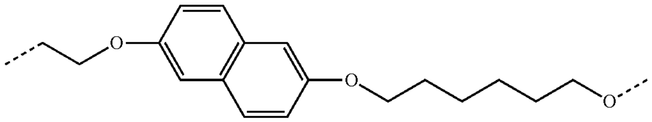
(Sp-x-8)
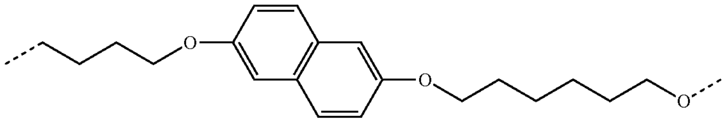
(Sp-x-9)
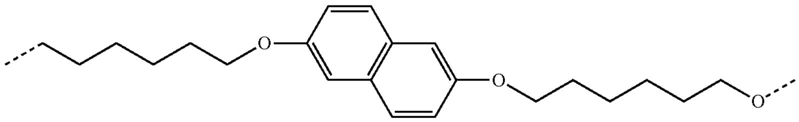
[Chem. 32]
(Sp-y-1)
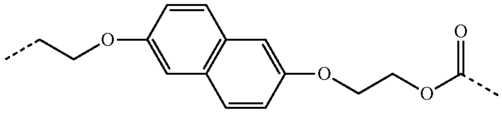
(Sp-y-2)
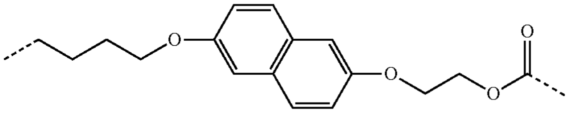
(Sp-y-3)
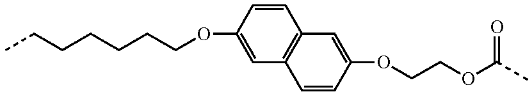
(Sp-y-4)
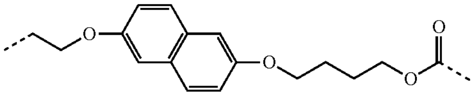
(Sp-y-5)
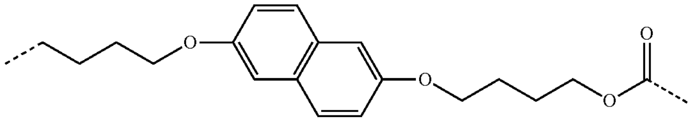

-continued
(Sp-y-6)
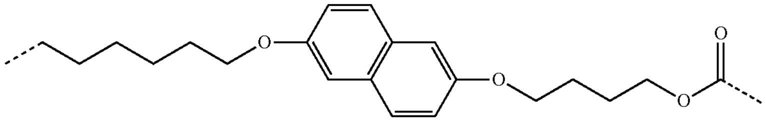
(Sp-y-7)
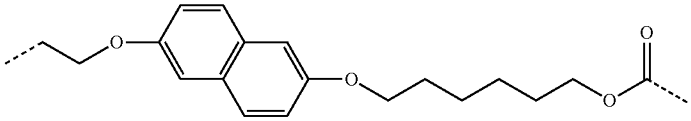
(Sp-y-8)
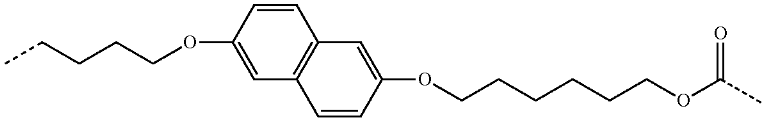
(Sp-y-9)
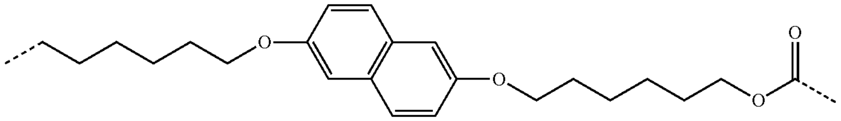
[Chem. 33]
(Sp-z-1)
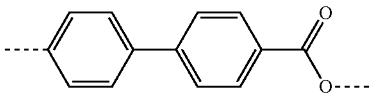
(Sp-z-2)
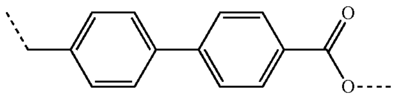
(Sp-z-3)
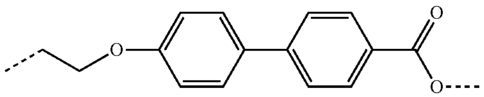
(Sp-z-4)
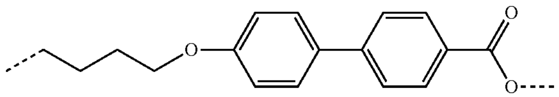
(Sp-z-5)
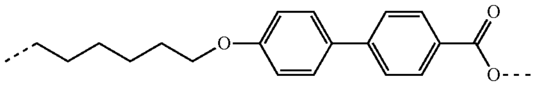
(Sp-z-6)
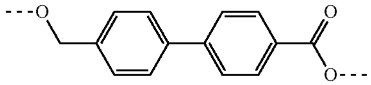
(Sp-z-7)
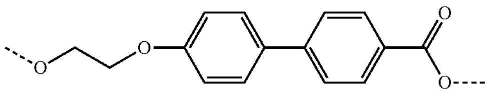
(Sp-z-8)
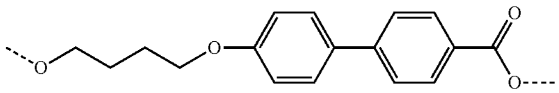
(Sp-z-9)
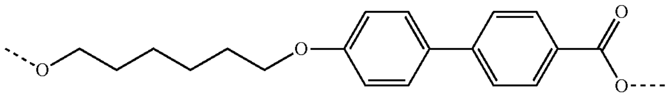
[Chem. 34]
(Sp-aa-1)
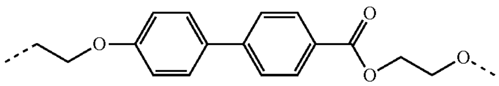
(Sp-aa-2)
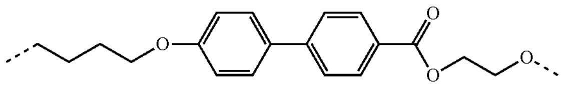
(Sp-aa-3)
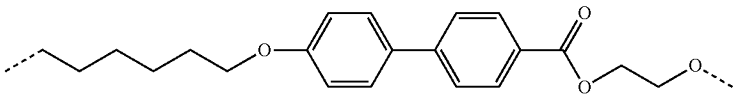
(Sp-aa-4)
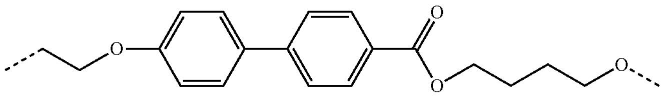

-continued
(Sp-aa-5)
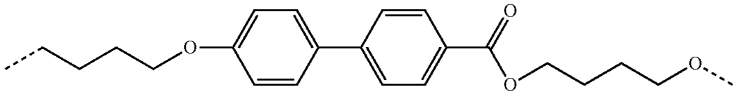
(Sp-aa-6)
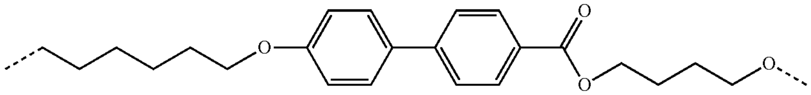
(Sp-aa-7)
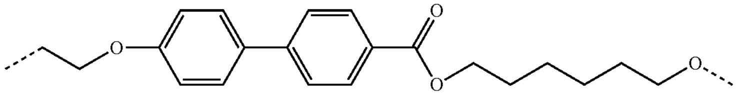
(Sp-aa-8)
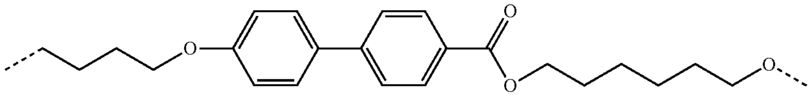
(Sp-aa-9)
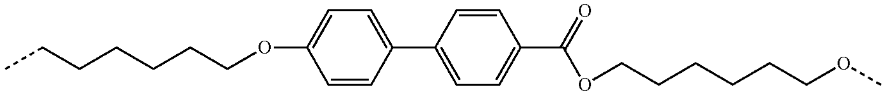
[Chem. 35]
(Sp-ab-1)
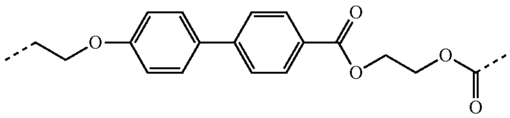
(Sp-ab-2)
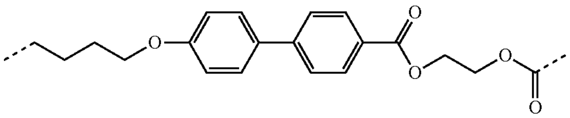
(Sp-ab-3)
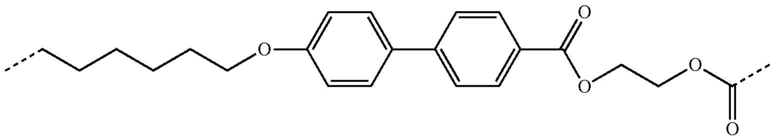
(Sp-ab-4)
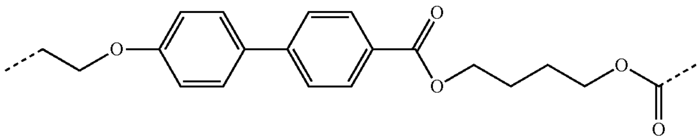
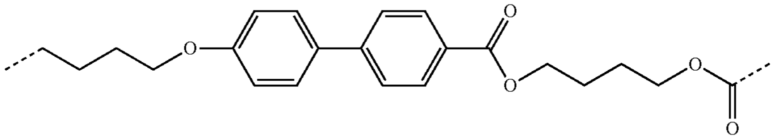
(Sp-ab-6)
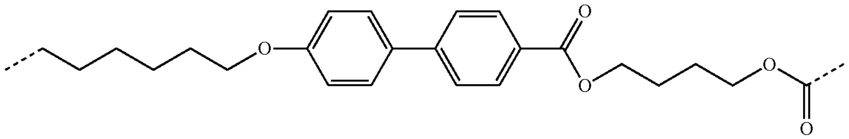
(Sp-ab-7)
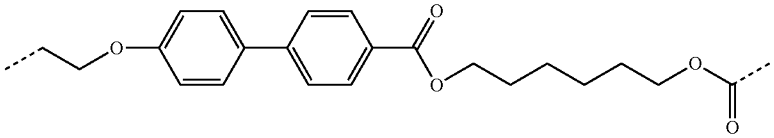
(Sp-ab-8)
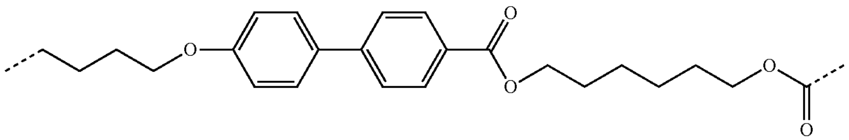

-continued
(Sp-ab-9)
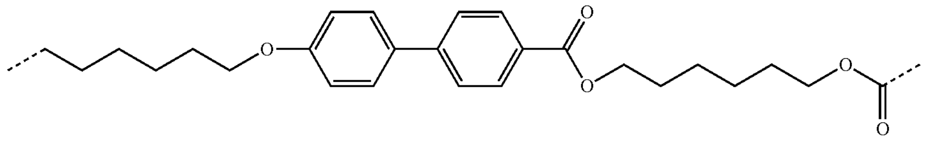
[Chem. 36]
(Sp-ac-1)
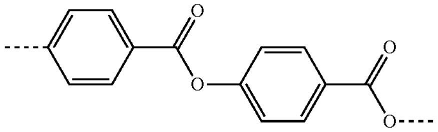
(Sp-ac-2)
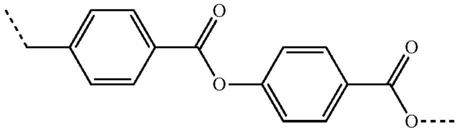
(Sp-ac-3)
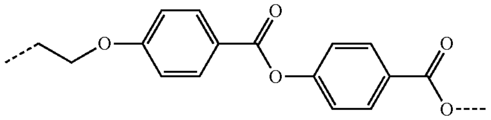
(Sp-ac-4)
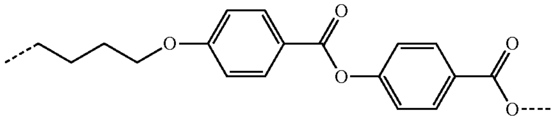
(Sp-ac-5)
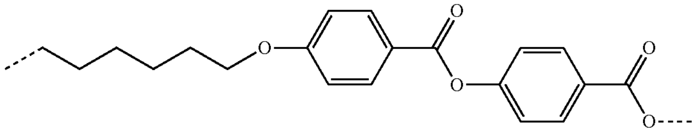
[Chem. 37]
(Sp-ad-1)
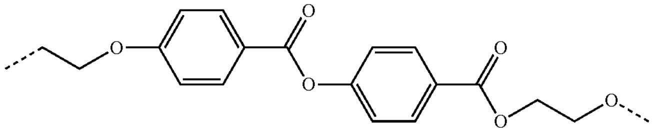
(Sp-ad-2)
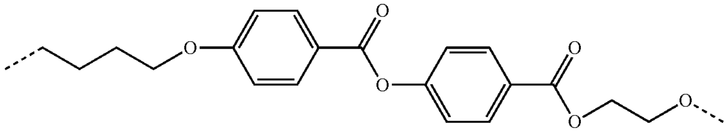
(Sp-ad-3)
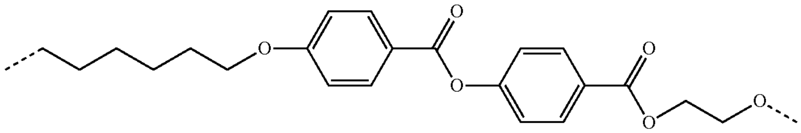
(Sp-ad-4)
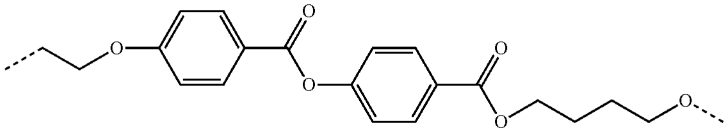
(Sp-ad-5)
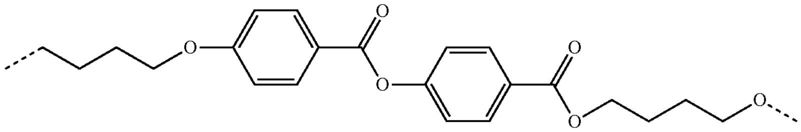
(Sp-ad-6)
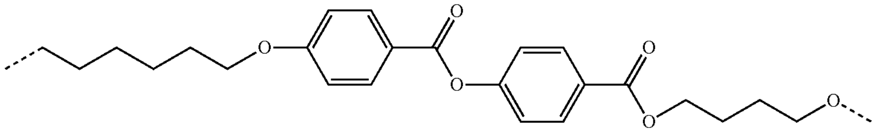

-continued
(Sp-ad-7)
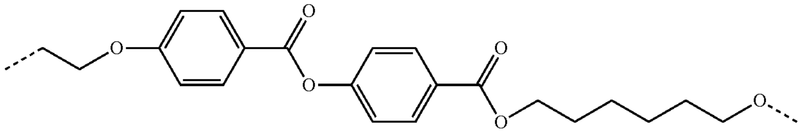
(Sp-ad-8)
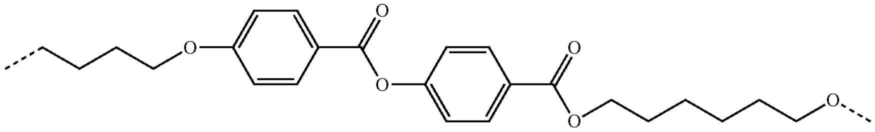
(Sp-ad-9)
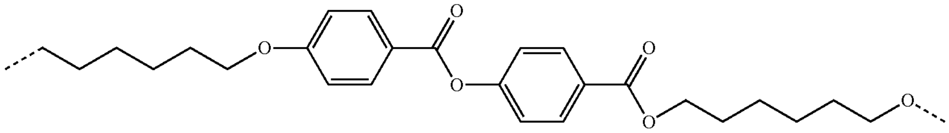
[Chem. 38]
(Sp-ae-1)
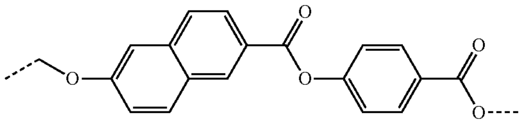
(Sp-ae-2)
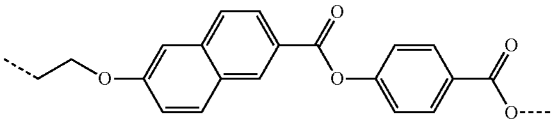
(Sp-ae-3)
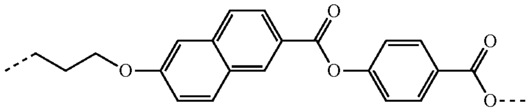
(Sp-ae-4)
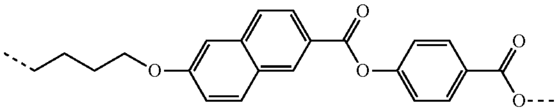
(Sp-ae-5)
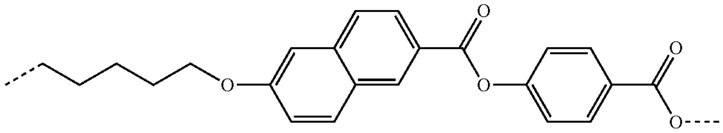
(Sp-ae-6)
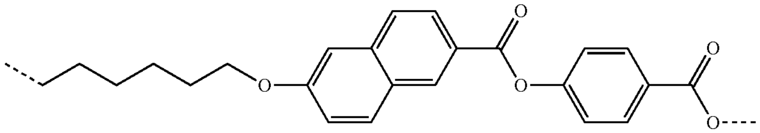
(Sp-ae-7)
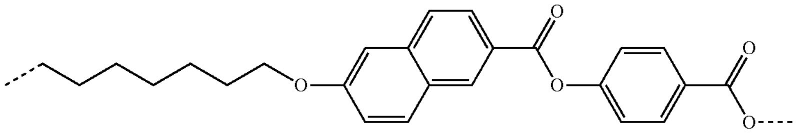
(Sp-ae-8)
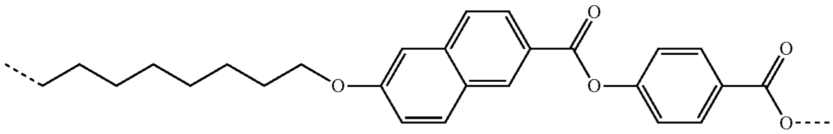
(Sp-ae-9)
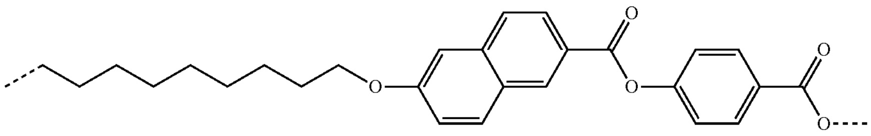

-continued
[Chem. 39]
(Sp-af-1)
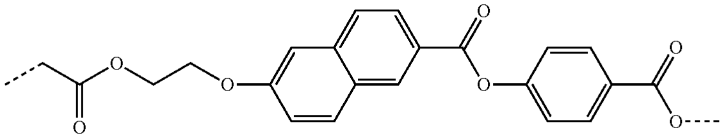
(Sp-af-2)
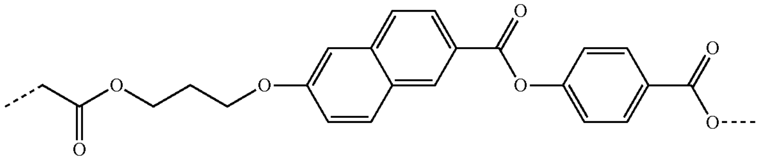
(Sp-af-3)
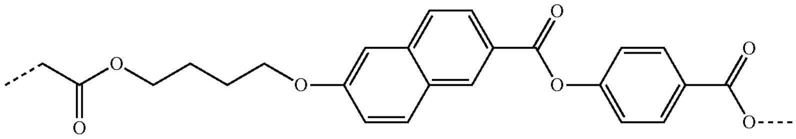
(Sp-af-4)
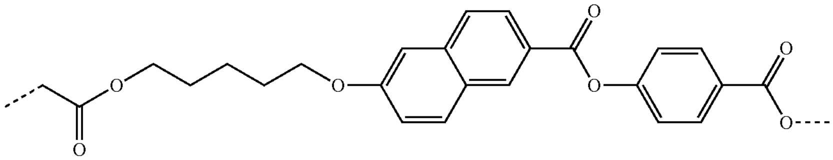
(Sp-af-5)
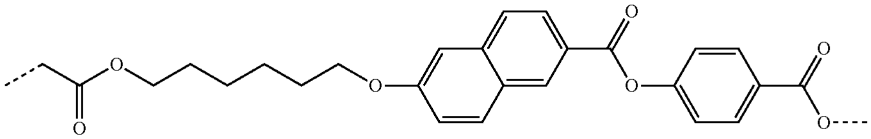
(Sp-af-6)
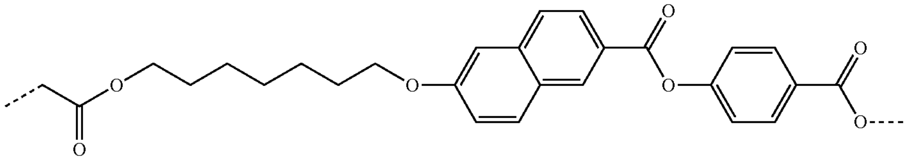
(Sp-af-7)
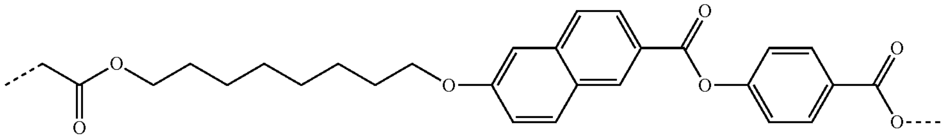
(Sp-af-8)
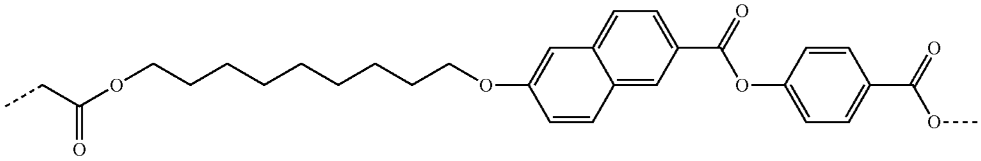
[Chem. 40]
(Sp-ag-1)
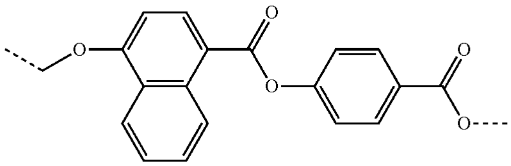
(Sp-ag-2)
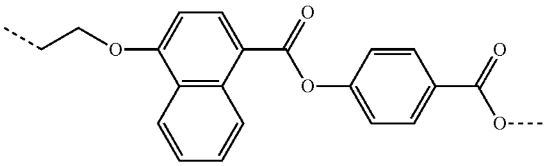

-continued
(Sp-ag-3)
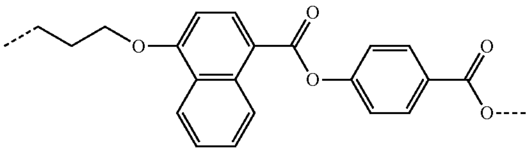
(Sp-ag-4)
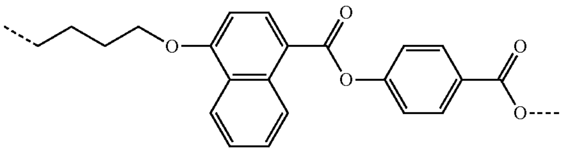
(Sp-ag-5)
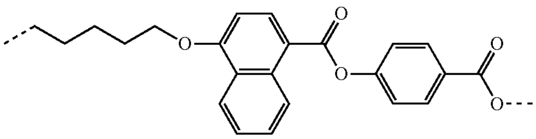
(Sp-ag-6)
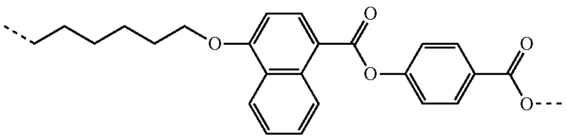
(Sp-ag-7)
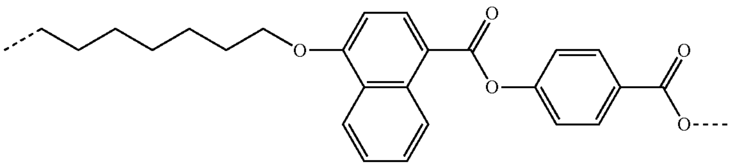
(Sp-ag-8)
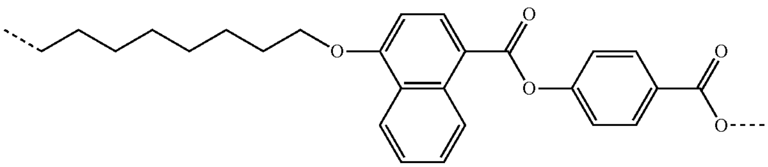
(Sp-ag-9)
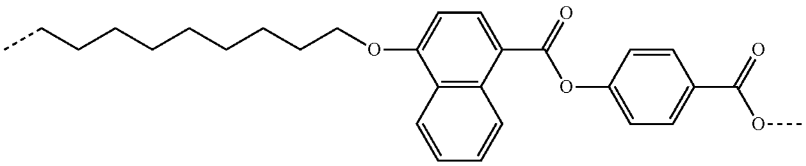
[Chem. 41]
(Sp-ah-1)
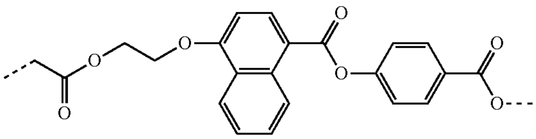
(Sp-ah-2)
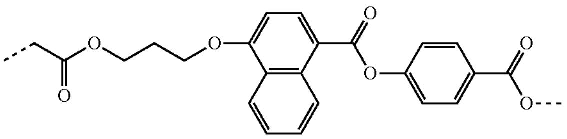
(Sp-ah-3)
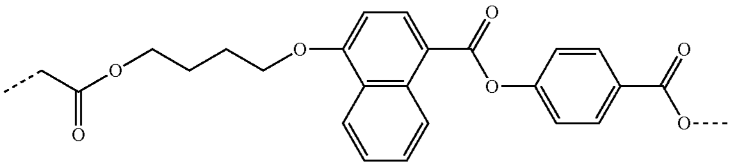
(Sp-ah-4)
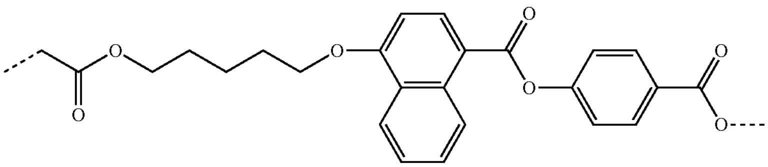
(Sp-ah-5)
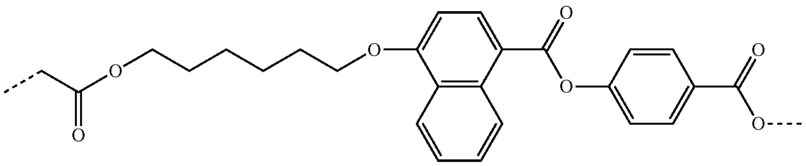

-continued (Sp-ah-6)

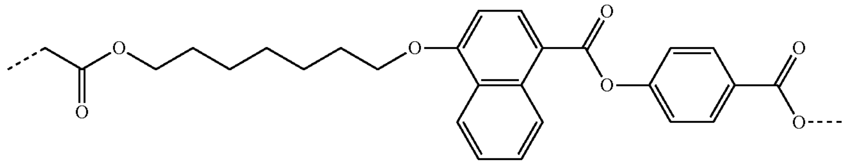

(Sp-ah-7)

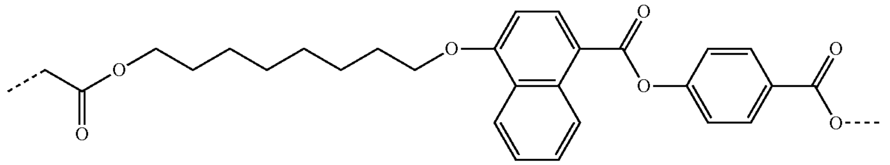

(Sp-ah-8)

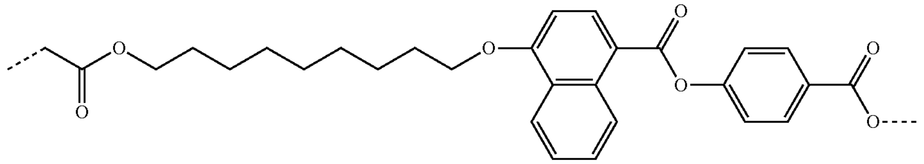

$A^1$ in the general formula (1) is preferably a trans-1,4-cyclohexylene group, a pyrimidine-2,5-diyl group or a 1,4-phenylene group, more preferably a pyrimidine-2,5-diyl group or a 1,4-phenylene group, further preferably a 1,4-phenylene group.

Because the solubility of the polymer of the invention improves, one or more hydrogen atoms binding to the above group of $A^1$ may be substituted with a fluorine atom, a methyl group or a methoxy group.

$X^1$, $X^2$, $X^4$ and $X^5$ in the general formula (1) are not simultaneously hydrogen atoms. That is, the case where only $X^3$ in the para position with respect to the diazenyl group is substituted is not included. Due to this structure, the ability of controlling alignment of a photo-alignment film obtained using the compound of the general formula (1) or the polymer of the general formula (2) is enhanced, and the effect of reducing AC burn-in is obtained. Although the details of the mechanism have not been known yet, it is supposed, as the cause, that the isomerization advances actively because the degree of constrains which the surrounding polymer imposes on the diazenyl group becomes smaller when there is no substituent in the para position with respect to the diazenyl group.

$X^2$ and $X^4$ do not have any crosslinkable double bond. Moreover, at least one of $X^2$ and $X^4$ is not a hydrogen atom when $X^1$, $X^3$ and $X^5$ are simultaneously hydrogen atoms. Due to this structure, the ability of controlling alignment of a photo-alignment film obtained using the compound of the general formula (1) or the polymer of the general formula (2) is enhanced, and the effect of reducing AC burn-in is obtained. Although the details of the mechanism have not been known yet, it is supposed, as the cause, that the isomerization advances actively because there is a space for reaction which is large enough for the isomerization of the diazenyl group when there is a substituent in the meta position with respect to the diazenyl group.

To enhance the ability of controlling alignment of the invention, at least one of $X^2$ and $X^4$ is preferably a fluorine atom, a chlorine atom, a hydroxy group, a nitro group, a cyano group or a group represented by the formula (G).

At least one of $X^1$ to $X^5$ is preferably a linear or branched alkyl group having 1 to 20 carbon atoms (one or more non-adjacent $—CH_2—$'s in the alkyl group may be independently substituted with —O—, —COO—, —OCO—, —CH=CH—, —CF=CF—, $—CF_2O—$, $—OCF_2—$, $—CF_2CF_2—$, —C≡C—, —CO—, —S—, $—Si(CH_3)_2—O—Si(CH_3)$ 2-, —NR'—, —NR'—CO—, —CO—NR'—, —NR'—CO—O—, —O—CO—NR'—, —NR'—CO—NR'—, or —O—CO—O— (in the formulae, R's independently represent hydrogen or an alkyl group having 1 to 5 carbon atoms), and one or more hydrogen atoms of the $—CH_2—$'s in the linear or branched alkyl group may be substituted with a fluorine atom, a chlorine atom, a hydroxy group or a cyano group).

One or more of $X^1$ to $X^5$ are preferably a linear or branched alkyl or alkoxy group having 1 to 20 carbon atoms, and at least one of $X^2$ and $X^4$ is more preferably a linear or branched alkyl or alkoxy group having 1 to 20 carbon atoms.

These preferable groups can further enhance the ability of controlling alignment of the photo-alignment film.

One or more of $X^1$ to $X^5$ are more preferably a branched alkyl group having 3 to 20 carbon atoms. In this case, the ability of controlling alignment of the photo-alignment film can be further enhanced.

Although the details of the mechanism have not been known yet, it is supposed that the influence of the structural change due to photoisomerization on the surroundings, for example the excluded volume effect, is enhanced when a hydrogen atom of the diazenylbenzene, which has a photoisomerizable diazenyl group, is substituted with a relatively bulky branched alkyl group and that the enhanced influence is involved.

With respect to the positions $X^1$ to $X^5$ to be substituted with a branched alkyl group having 3 to 20 carbon atoms, it is preferable that any one or more of $X^1$, $X^2$, $X^4$ and $X^5$ are a branched alkyl group having 3 to 20 carbon atoms, and it is more preferable that at least one of $X^2$ and $X^4$ is a branched alkyl group having 3 to 20 carbon atoms.

When the branched alkyl group is present on the position(s), the influence due to photoisomerization is enhanced, and the ability of controlling alignment of the photo-alignment film can be further enhanced.

The branched alkyl group is preferably a group having 3 to 15 carbon atoms, more preferably a group having 4 to 10 carbon atoms, further preferably a group having 3 to 7 carbon atoms, particularly preferably an isopropyl group, a tertiary butyl group (a t-butyl group), an amyl group or a tert-butoxycarbonyl group.

When the preferable branched alkyl groups are contained, the influence due to photoisomerization is obtained satisfactory, and the ability of controlling alignment of the photo-alignment film can be further enhanced.

One or more non-adjacent —$CH_2$—'s in the branched alkyl group may be substituted with any of the above divalent groups. The divalent group is preferably —O—, —COO— or —OCO—.

Being substituted with the group(s), the ability of controlling alignment of the photo-alignment film can be further enhanced.

When one or more of $X^1$ to $X^5$ are a linear alkyl or alkoxy group having 1 to 20 carbon atoms, the number of the carbon atoms of the group is preferably 1 to 10, more preferably 1 to 8, further preferably 1 to 5.

When the preferable linear alkyl or alkoxy groups are contained, the ability of controlling alignment of the photo-alignment film can be further enhanced.

One or more non-adjacent —$CH_2$—'s in the linear alkyl group may be substituted with any of the above divalent groups but are preferably not substituted. When the —$CH_2$—'s are not substituted, the linear alkyl group becomes a non-polar group, and the ability of controlling alignment of the photo-alignment film can be further enhanced.

$X^3$ may be substituted or unsubstituted and is preferably a hydrogen atom.

In the formula (G) of the general formula (1), $A^2$ is preferably a single bond, a trans-1,4-cyclohexylene group, a pyrimidine-2,5-diyl group or a 1,4-phenylene group, more preferably a single bond.

In the formula (G) of the general formula (1), n is preferably 0.

In the formula (G) of the general formula (1), $Z^2$ is preferably a single bond or a linear alkylene group. The number of the carbon atoms of the alkylene group is preferably 1 to 20, more preferably 1 to 8.

One or more non-adjacent —$CH_2$— groups in the alkylene group are preferably independently substituted with —O—, —COO—, —OCO—, —CH=CH—, —CF=CF—, —$CF_2O$—, —$OCF_2$—, —$CF_2CF_2$—, —C≡C— or —CO—.

In the formula (G), $A^3$ is preferably a trans-1,4-cyclohexylene group, a pyrimidine-2,5-diyl group or a 1,4-phenylene group, more preferably a pyrimidine-2,5-diyl group or a 1,4-phenylene group, further preferably a 1,4-phenylene group.

In the formula (G), R is preferably the linear or branched alkyl group having 4 to 20 carbon atoms described above as one or more substituents of $X^1$ to $X^5$. Preferable specific examples of R include the same groups as the above preferable substituents of $X^1$ to $X^5$.

<<Cured Product>>

The second embodiment of the invention is a cured product obtained by polymerizing the compound of the first embodiment.

The cured product is preferably a polymer obtained through the polymerization of the polymerizable group P of compound (1) and the polymerizable group P of another compound (1). The polymerization method of the polymerizable groups P is not particularly limited, and a general method can be used.

A kind of compound (1) or two or more kinds thereof may be used to form the cured product.

The cured product may contain any component(s) other than the compound (1).

The proportion of the compound (1) based on the total mass of the cured product is preferably 10 to 100% by mass, more preferably 40 to 100% by mass, further preferably 70 to 100% by mass.

<<Polymer>>

The polymer of the third embodiment of the invention has one or more kinds of side-chain unit represented by the general formula (2). The polymer is useful as a material of a photo-alignment film.

<Side-Chain Unit (2)>

A side-chain unit (2) is represented by the general formula (2) and is a side-chain unit containing an azobenzene derivative. The side-chain unit (2) is sometimes called an azo unit below.

[Chem. 42]

(2)

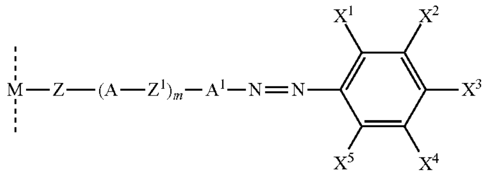

In the formula (2), the broken line represents the main chain of the polymer, and M represents a monomer unit (a repeat unit) of the polymer. The definitions of Z, $Z^1$, A, $A^1$, m and $X^1$ to $X^5$ are the same as the definitions in the formula (1).

M in the formula (2) is a monomer unit forming the main chain of the polymer obtained through the polymerization of the polymerizable groups P which the compound (1) molecules have. A kind of M may be used, or a combination of two or more kinds thereof may be used.

Preferable examples of M include monomer units which constitute at least one polymer main chain selected from the group consisting of polyolefins, polyethers, polyamides, polyesters, polycarbonates and polysiloxanes. Of the examples, monomer units of polyolefins, polyethers, polyamides and polyesters, which are more suitable for the formation of a photo-alignment film, are preferable, and monomer units of polyolefins are more preferable. In the present description, a monomer unit of a polyolefin means a monomer unit formed by a group containing a polymerizable vinyl group, and examples thereof are monomer units which can form polymethacrylate, polyacrylate, polyvinyl, polymethacrylamide, polyacrylamide, polyvinylacetamide or the like.

M is preferably, for example, a monomer unit formed by any of the polymerizable groups represented by the formulae (III-1) to (III-17), more preferably a monomer unit formed by any of the olefinic polymerizable groups represented by the formulae (III-1) to (III-8), further preferably a monomer unit formed by any of the acrylic polymerizable groups represented by the formulae (III-1) to (III-5).

<Second Side-Chain Unit>

The polymer of the invention is preferably a copolymer having more than one kind of side-chain unit. The polymer of the invention is preferably a copolymer with a side-chain unit having a photochemically crosslinkable site (sometimes called a photocrosslinkable unit).

When the polymer is a copolymer, the ability of controlling alignment of the photo-alignment film can be further enhanced.

The photochemically crosslinkable site preferably contains any one or more structures represented by the following formulae (II-1) to (II-8).

[Chem. 43]

(II-1)

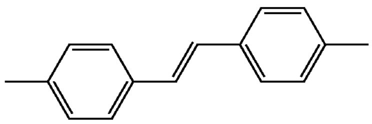

(II-2)

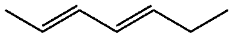

(II-3)

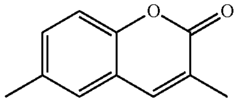

(II-4)

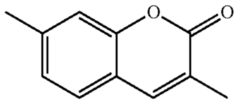

(II-5)

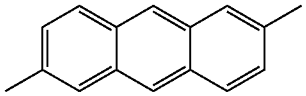

(II-6)

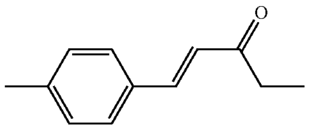

(II-7)

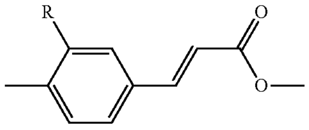

(II-8)

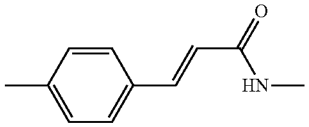

(In the formula, R represents a hydrogen atom or a linear or branched alkyl group having 1 to 9 carbon atoms, and one or more non-adjacent —$CH_2$—'s in the alkyl group may be independently substituted with —O—, —COO— or —OCO—.)

The side-chain unit having the photochemically crosslinkable site is, for example, preferably a side-chain unit (CP) represented by the following formula (CP). A kind of side-chain unit (CP) may be contained in the copolymer, or a combination of two or more kinds thereof may be contained.

[Chem. 44]

(CP)

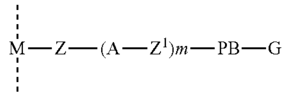

(In the formula (CP), the broken line represents the main chain of the polymer, and M represents a monomer unit of the polymer. PB is the photochemically crosslinkable site. Z, $Z^1$, A and m have the same meanings as those in the formula (1) but are selected independently of those in the formula (2). G is a group represented by the formula (G) but is selected independently of that in the formula (2).)

Examples of M in the formula (CP) include the same monomer units as the monomer units in the formula (2).

M in the formula (CP) may be the same as or different from the monomer unit in the formula (2) but is preferably the same as the monomer unit in the formula (2) to form an excellent photo-alignment film.

A kind of M in the formula (CP) may be used, or a combination of two or more kinds thereof may be used.

In the formula (CP), PB preferably contains any one or more structures represented by the formulae (II-1) to (II-8) and is more preferably a structure represented by the formula (II-6) or the formula (II-7).

The side-chain unit (CP) represented by the formula (CP) is particularly preferably a side-chain unit (3) represented by the following formula (3).

[Chem. 45]

(3)

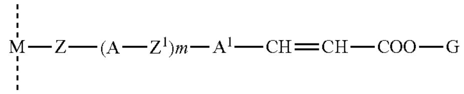

(In the formula (3), the broken line represents the main chain of the polymer, and M represents a monomer unit of the polymer. G is a group represented by the formula (G) but is selected independently of that in the formula (2). Z, $Z^1$, A, $A^1$ and m have the same meanings as those in the formula (2) but are selected independently of those in the formula (2).)

In the formula (3), Z is preferably a linear alkylene group. The number of the carbon atoms of the alkylene group is preferably 2 to 20, more preferably 4 to 15, further preferably 6 to 11.

Because the solubility of the polymer of the invention improves, one or more non-adjacent —$CH_2$— groups in the alkylene group are preferably independently substituted with —O—, —COO— or —OCO—.

Specific examples of Z are preferably those represented by the chemical formula (Sp-a-1) to the chemical formula (Sp-ah1-8). In each of the chemical formulae, the broken line on the left represents the bond to the polymerizable group P, and the broken line on the right represents the bond to A or to $A^1$.

Although Z can be selected according to the need, of these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-l-13) to (Sp-l-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9) and the chemical formulae (Sp-aa-1) to (Sp-aa-9) are more preferable.

In the formula (3), m is preferably 1.

A's in the formula (3) are preferably each independently a trans-1,4-cyclohexylene group, a 1,4-naphthylene group, a 2,6-naphthylene group, a 2,5-furanylene group, a pyrimidine-2,5-diyl group or a 1,4-phenylene group. Of the groups, a 1,4-phenylene group is more preferable because the solubility of the polymer of the invention improves.

$Z^1$ in the formula (3) is preferably a single bond, —COO—, —OCO—, —$OCH_2$—, —$CH_2O$—, —$CF_2O$—, —$OCF_2$—, —$CF_2CF_2$—, —NR—, —CO— or —C≡C—. Of these, —$OCH_2$—, —$CH_2O$—, —$CF_2O$—, —$OCF_2$—, —$CF_2CF_2$—, —NR— or —CO— is more preferable because the solubility of the polymer of the invention improves. Moreover, because the ability of controlling alignment of the invention is enhanced, a single bond, —COO—, —OCO—, —$CF_2O$— or —$OCF_2$— is more preferable, and a single bond, —COO— or —OCO— is further preferable.

$A^1$ in the formula (3) is preferably a trans-1,4-cyclohexylene group, a 1,4-naphthylene group, a 2,6-naphthylene group, a 2,5-furanylene group, a pyrimidine-2,5-diyl group or a 1,4-phenylene group. Of the groups, a 1,4-phenylene group is more preferable because the solubility of the polymer of the invention improves.

In the formula (G) of the formula (3), $A^2$ is preferably a single bond, a trans-1,4-cyclohexylene group, a pyrimidine-2,5-diyl group or a 1,4-phenylene group, more preferably a single bond.

In the formula (G) of the formula (3), n is preferably 0.

In the formula (G) of the formula (3), $Z^2$ is preferably a single bond or a linear alkylene group. The number of the carbon atoms of the alkylene group is preferably 1 to 20, more preferably 1 to 8.

One or more non-adjacent —$CH_2$— groups in the alkylene group are preferably independently substituted with —O—, —COO—, —OCO—, —CH═CH—, —CF═CF—, —$CF_2O$—, —$OCF_2$—, —$CF_2CF_2$—, —C≡C— or —CO—.

In the formula (G) of the formula (3), $A^3$ is preferably a trans-1,4-cyclohexylene group, a pyrimidine-2,5-diyl group or a 1,4-phenylene group, more preferably a pyrimidine-2,5-diyl group or a 1,4-phenylene group, further preferably a 1,4-phenylene group.

In the formula (G) of the formula (3), R is preferably a linear or branched alkyl group having 1 to 20 carbon atoms, more preferably a linear alkyl group having 1 to 10 carbon atoms, further preferably a linear alkyl group having 1 to 5 carbon atoms.

One or more hydrogen atoms of the alkyl group are preferably substituted with a fluorine atom, a chlorine atom, a hydroxy group, a nitro group or a cyano group, and the terminal methyl group of the alkyl group is more preferably substituted with a fluorine atom, a chlorine atom, a hydroxy group, a nitro group or a cyano group.

When the preferable alkyl groups are contained, the solubility of the polymer of the invention can be further improved.

When the polymer of the invention has the side-chain unit (2) and the side-chain unit (CP), the ratio by mole ((2)/(CP)) indicated by side-chain unit (2)/side-chain unit (CP) is preferably 10/1 to 1/100, more preferably 1/1 to 1/50, further preferably 1/8 to 1/25, particularly preferably 1/9 to 1/20.

<Third Side-Chain Unit>

The polymer of the invention may be a copolymer with a side-chain unit having no photochemically crosslinkable site that is different from the side-chain unit represented by the formula (2). The copolymer may contain the side-chain unit (CP) but does not have to contain the side-chain unit (CP).

The side-chain unit is preferably, for example, a side-chain unit (T) represented by the following formula (T). A kind of side-chain unit (T) may be contained in the copolymer, or a combination of two or more kinds thereof may be contained.

[Chem. 46]

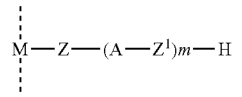

(T)

(In the formula (T), the broken line represents the main chain of the polymer, and M represents a monomer unit of the polymer. H represents a hydrogen atom. Z, $Z^1$, A and m have the same meanings as those in the formula (1), but are selected independently of those in the formula (1).)

Examples of M in the formula (T) include the same monomer units as the monomer units in the formula (2).

M in the formula (T) may be the same as or different from the monomer unit in the formula (2).

A kind of M in the formula (T) may be used, or a combination of two or more kinds thereof may be used.

In the formula (T), Z is preferably a linear alkylene group. The number of the carbon atoms of the alkylene group is preferably 2 to 20, more preferably 3 to 10, further preferably 3 to 7.

Because the solubility of the polymer of the invention improves, one or more non-adjacent —$CH_2$— groups in the alkylene group are preferably independently substituted with —O—, —COO— or —OCO—.

Specific examples of Z are preferably those represented by the chemical formula (Sp-a-1) to the chemical formula (Sp-ah1-8). In each of the chemical formulae, the broken line on the left represents the bond to the polymerizable group P, and the broken line on the right represents the bond to A or to the hydrogen atom (H).

Although Z can be selected according to the need, of these, those represented by the chemical formulae (Sp-a-6) to (Sp-a-16), the chemical formulae (Sp-b-3) to (Sp-b-10), the chemical formulae (Sp-c-3) to (Sp-c-10), the chemical formulae (Sp-d-3) to (Sp-d-12), the chemical formulae (Sp-k-4) to (Sp-k-7), the chemical formulae (Sp-l-13) to (Sp-l-17), the chemical formulae (Sp-o-3) to (Sp-o-14), the chemical formulae (Sp-p-2) to (Sp-p-13), the chemical formulae (Sp-s-1) to (Sp-s-8), the chemical formulae (Sp-t-1) to (Sp-t-8), the chemical formulae (Sp-y-1) to (Sp-y-9) and the chemical formulae (Sp-aa-1) to (Sp-aa-9) are more preferable.

In the formula (T), m is preferably 1.

A's in the formula (T) are preferably each independently a trans-1,4-cyclohexylene group, a 1,4-naphthylene group, a 2,6-naphthylene group, a 2,5-furanylene group, a pyrimidine-2,5-diyl group or a 1,4-phenylene group. Of the groups, a 1,4-phenylene group is more preferable because the solubility of the polymer of the invention improves.

$Z^1$ in the formula (T) is preferably a single bond, —COO—, —OCO—, —$OCH_2$—, —$CH_2O$—, —$CF_2O$—, —$OCF_2$—, —$CF_2CF_2$—, —NR—, —CO— or —C≡C—.

Of these, —$OCH_2$—, —$CH_2O$—, —$CF_2O$—, —$OCF_2$—, —$CF_2CF_2$—, —NR— or —CO— is more preferable because the solubility of the polymer of the invention improves. Moreover, because the ability of controlling alignment of the invention is enhanced, a single bond, —COO—, —OCO—, —$CF_2O$— or —$OCF_2$— is more preferable, and a single bond, —COO— or —OCO— is further preferable.

It is also preferable that one or more hydrogen atoms in the formula (T) are substituted with any functional group selected from a cyano group, a carbonyl group, a hydroxyl group, an amide group, an ether group, an ester group, a thiol group, a sulfonic group, a nitro group and an acetyl group.

When the functional groups are contained, the solubility of the polymer of the invention can be further improved.

When the polymer of the invention has the side-chain unit (2) and the side-chain unit (T), the ratio by mole ((2)/(T)) indicated by side-chain unit (2)/side-chain unit (T) is preferably 1/10 to 10/1, more preferably 1/5 to 5/1, further preferably 1/2 to 2/1, particularly preferably 3/4 to 4/3.

When the polymer of the invention has the side-chain unit (T) and the side-chain unit (CP), the ratio by mole ((T)/(CP)) indicated by side-chain unit (T)/side-chain unit (CP) is preferably 1/50 to 1/2, more preferably 1/20 to 1/3, further preferably 1/10 to 1/4.

<<Synthesis of Compound and Polymer>>

The methods for synthesizing the compound and the polymer of the invention are not particularly limited, and, for example, the methods described in PTL 1 can be applied. When the polymer is synthesized, a known initiator can be used according to the polymerization style of the polymerizable functional group. As the initiator, for example, the known initiators described in Synthesis and Reaction of Polymers (edited by The Society of Polymer Science, Japan, Kyoritsu Shuppan Co., Ltd.) and the like can be used.

The amount of the initiator can be, for example, 0.1 to 10% by mass relative to the total mass of the mixture containing the monomer components to be polymerized. Moreover, the target polymer can also be synthesized through the addition reaction to the main chain of the polymer using a polysiloxane compound.

The polymer of the invention can be obtained through polymerization reaction in a reactor and further purification. Examples of the solvent for the polymerization reaction include benzene, toluene, xylene, ethylbenzene, pentane, hexane, heptane, octane, cyclohexane, cycloheptane, methanol, ethanol, 1-propanol, 2-propanol, ethylene glycol, ethylene glycol monomethyl ether, ethylene glycol dimethyl ether, 2-butanone, acetone, tetrahydrofuran, γ-butyrolactone, N-methyl-pyrrolidone, dimethyl sulfoxide, dimethylformamide and the like. A kind of solvent may be used for the polymerization reaction, or a combination of two or more kinds thereof may be used.

The polymer of the invention can also be obtained by a method of applying a composition containing the monomers onto a substrate, removing the solvent by drying if necessary and then conducting polymerization reaction by heating or light irradiation.

<<Formation of Photo-Alignment Film>>

A photo-alignment film having the ability of controlling alignment is obtained by applying a polarized ultraviolet ray to a film composed of the polymer of the invention. With respect to the method for obtaining a film composed of the polymer, for example, a film can be obtained by applying a solution of the polymer to a substrate and drying the solution.

The photo-alignment film (liquid crystal alignment layer) of the invention can be applied to a liquid crystal display element of the horizontal alignment or vertical alignment mode.

Examples of the material of the substrate include glass, silicon, polyethylene terephthalate, polybutylene terephthalate, polyether sulfones, polycarbonates, triacetylcellulose and the like.

An electrode layer such as Cr, Al, an ITO film composed of $In_2O_3$—$SnO_2$ or a NESA film composed of $SnO_2$ may be provided on the substrate. For the patterning of such an electrode layer, a photoetching method, a method in which a mask is used for forming the electrode layer and the like are used. Moreover, a color filter layer or the like may be formed on the substrate.

Examples of the method for applying a solution containing the polymer onto the substrate include spin coating, die coating, gravure coating, flexography, inkjet printing and the like.

The solid concentration of the solution to be applied is preferably 0.5 to 10% by weight. The solid concentration is further preferably selected from this range considering the method for applying the solution onto the substrate, the viscosity, the volatility and the like.

After applying the polymer solution onto the substrate, the solvent is preferably removed by heating the coated surface. The heating temperature is, for example, preferably 50 to 300° C., more preferably 80 to 200° C. The heating period at a temperature in the preferable range is, for example, preferably 2 to 200 minutes, more preferably 2 to 100 minutes.

A photo-alignment film to which the capability of regulating alignment has been given is obtained by causing the photoisomerization reaction of the azo unit and the photocrosslinking reaction of the photocrosslinkable unit by applying linearly polarized light from the normal line direction of the coating film surface and/or applying unpolarized light or linearly polarized light from an oblique direction to the coating film formed on the substrate. To give a desired pretilt angle, application of linearly polarized light from an oblique direction is preferable. Here, application from an oblique direction means the case where the angle between the direction of the light irradiation and the substrate surface is one degree or more and 89 degrees or less. When the film is used as a photo-alignment film for the vertical alignment, in general, the pretilt angle is preferably 70 to 89.8°. When the film is used as a photo-alignment film for the horizontal alignment, in general, the pretilt angle is preferably 0 to 200.

As the light applied to the coating film, for example, ultraviolet rays and visible rays including light having a wavelength of 150 nm to 800 nm can be used, but ultraviolet rays of 270 nm to 450 nm are particularly preferable.

Examples of the light source include a xenon lamp, a high-pressure mercury lamp, an ultra-high-pressure mercury lamp, a metal halide lamp and the like. Linearly polarized light is obtained by allowing light from such a light source to pass through a polarizing filter or a polarizing prism. Moreover, the range of applied wavelengths of ultraviolet light and visible light obtained from such a light source may be limited using an interference filter, a color filter or the like.

The thickness of the photo-alignment film formed is preferably around 10 to 250 nm, more preferably around 10 to 100 nm.

<<Production Method of Liquid Crystal Display Element>>

Using the photo-alignment film of the invention, a liquid crystal cell having a liquid crystal composition supported between a pair of substrates and a liquid crystal display element obtained using the liquid crystal cell can be produced, for example as follows.

A liquid crystal cell can be produced by preparing two substrates on which the photo-alignment films according to the invention have been formed and placing liquid crystals between the two substrates. The photo-alignment film may be formed on only one of the two substrates.

Examples of the method for producing a liquid crystal cell include the following methods. First, two substrates are arranged in a manner that the photo-alignment films face each other, and the edge parts are pasted together using a sealing agent while constant space (cell gap) is kept between the two substrates. A liquid crystal composition is injected into the cell gap surrounded by the substrate surfaces and the sealing agent, and then the injection hole is sealed. A liquid crystal cell can be thus produced.

A liquid crystal cell can be produced also by a method called ODF (One Drop Fill) process. Example procedures thereof are as follows. For example, an ultraviolet-curing sealing agent is applied to a certain place of a substrate on which the photo-alignment film has been formed, and a liquid crystal composition is dropped onto the photo-alignment film. Then, the other substrate is pasted together in a manner that the photo-alignment films face each other. Next, the sealing agent is cured by applying ultraviolet light to the entire surfaces of the substrates. A liquid crystal cell can be thus produced.

It is desirable to remove the alignment derived from the flow of injection by heating the liquid crystal cell to a temperature at which the liquid crystal photo-alignment films used here exhibit the isotropic phase and then cooling slowly to room temperature.

The liquid crystal composition is not particularly limited, and for example, a known nematic liquid crystal composition can be used. In the case of a liquid crystal cell of the vertical alignment type, one having negative dielectric anisotropy is preferable. In the case of a liquid crystal cell of the horizontal alignment type, one having positive dielectric anisotropy is preferable.

A liquid crystal display element can be obtained by attaching a known polarizing plate to an outer surface of the liquid crystal cell.

<<Production Method of Optically Anisotropic Body>>

The optically anisotropic body of the invention has the photo-alignment film of the invention and a film composed of a polymer of a polymerizable liquid crystal composition formed on the photo-alignment film. This optically anisotropic body is useful for applications such as an optically anisotropic film used for optical compensation of a liquid crystal display element or the like. In the optically anisotropic body, when light travels in the body, the optical properties such as the velocity of the light, the refractive index and the absorption differ with the direction of travel.

Examples of the method for producing the optically anisotropic body of the invention include a method in which the photo-alignment film is formed on a substrate and the polymerizable liquid crystal composition is applied thereon, thereby forming a film of a polymer containing liquid crystal molecules aligned by the photo-alignment film.

When the optically anisotropic body is produced by applying the polymerizable liquid crystal composition onto the photo-alignment film, known coating methods such as bar coating, spin coating, roll coating, gravure coating, spray coating, die coating, cap coating and a dipping method can be used. To improve the coating properties, a known organic solvent may be added to the polymerizable liquid crystal composition. When an organic solvent is added, the organic solvent is removed by a known drying method after applying the polymerizable liquid crystal composition onto the photo-alignment film.

As the method for polymerizing the polymerizable liquid crystal composition, a method in which an active energy ray is applied to the polymerizable liquid crystal composition, a thermal polymerization method and the like are included.

When the polymerizable liquid crystal composition is polymerized by applying an active energy ray, it is preferable to apply the polymerizable liquid crystal composition onto the photo-alignment film and thus cause the polymerization in a state in which the polymerizable liquid crystal molecules are aligned.

When the polymerization of the polymerizable liquid crystal composition is caused by applying an active energy ray, for example, a method in which an ultraviolet ray is applied at an intensity of 1 $W/m^2$ to 10 $kW/m^2$ is used.

When the polymerizable liquid crystal composition is thermally polymerized, the polymerization is preferably conducted at the temperature at which the polymerizable liquid crystal composition shows the liquid crystal phase or lower. A specific heating temperature is, for example, preferably 20° C. to 300° C., more preferably 30° C. to 200° C., further preferably 30° C. to 120° C. When the polymerizable group is a (meth)acryloyloxy group, the polymerization is preferably conducted at a temperature lower than 90° C. At the preferable temperatures, uneven polymerization due to heat can be prevented.

As the polymerization method of the polymerizable liquid crystal composition, either or both of photopolymerization and thermal polymerization can be used.

The optical axis of the optically anisotropic body of the invention can be adjusted by regulating the pretilt angle with the photo-alignment film. In order to adjust the angle that the optical axis forms with the substrate surface to 0 degree to 45 degrees, the pretilt angle is preferably 0 degree to 45 degrees. Similarly, in order to adjust the angle that the optical axis forms with the substrate surface to 45 degrees to 90 degrees, the pretilt angle is preferably 45 degrees to 90 degrees.

Examples of the production steps of the optically anisotropic body having the photo-alignment film of the invention include the following method. In the first step, a coating film of the polymer is formed on a substrate. In the second step, the capability of regulating alignment is given to the coating film by applying light exhibiting anisotropy, and thus a photo-alignment film is formed. In the third step, a film of a polymerizable liquid crystal composition is formed on the photo-alignment film. In the fourth step, the film of the polymerizable liquid crystal composition is polymerized to form the optically anisotropic body. In the fourth step, the isomerization reaction and the crosslinking reaction may advance simultaneously in the photo-alignment film.

Because light is directly applied to the coating film of the polymer in the production steps described above, a photo-alignment film having excellent ability of controlling the alignment of liquid crystal molecules can be obtained.

Another production method is the following method. In the first step, a coating film of the polymer is formed on a substrate. In the second step, a film of a polymerizable liquid crystal composition is formed on the coating film. In the third step, the ability of regulating the alignment of liquid crystals is given to the coating film of the polymer by applying light exhibiting anisotropy, and thus a photo-alignment film is formed. In the fourth step, the film of the polymerizable liquid crystal composition is polymerized to form the optically anisotropic body. Here, the third step and the fourth step may be conducted simultaneously by light irradiation or the like. When the steps are conducted simultaneously, the number of the steps can be reduced.

According to the need, more than one layer composed of an optically anisotropic body may be laminated. A method for forming a laminate of an optically anisotropic body is a method in which a method of forming a single layer is repeated more than once. Examples thereof include a method of forming a first optically anisotropic body layer on a photo-alignment film, forming a new photo-alignment film on the first layer and forming a second optically anisotropic body layer on the photo-alignment film and a method of forming a second optically anisotropic body layer directly on a first optically anisotropic body layer formed on a photo-alignment film.

Examples of the applications of the laminate of an optically anisotropic body having more than one optically anisotropic body layer include an application where the optical compensation of the liquid crystal layer of a liquid crystal display element and that of the polarizing plate are conducted simultaneously, an application where the optical compensation and the enhancement of the brightness of the liquid crystal layer of a liquid crystal display element are conducted simultaneously, an application where the optical compensation and the enhancement of the brightness of the polarizing plate of a liquid crystal display element are conducted simultaneously and the like.

To stabilize the solvent resistance or the heat resistance of the obtained optically anisotropic body, the optically anisotropic body can be subjected to heat aging treatment.

The polymerizable liquid crystal composition used for producing the optically anisotropic body is not particularly limited, and a known liquid crystal composition containing polymerizable liquid crystals which exhibit liquid crystal properties by themselves or in a composition with another liquid crystal compound can be used.

The optically anisotropic body obtained by the above steps may be used as an individual optically anisotropic body after separating the optically anisotropic body layer from the substrate or can be used as an optically anisotropic body having a substrate without separating from the substrate.

EXAMPLES

The invention is described in further detail below using examples, but the invention is not limited by the examples. The structures of the compounds were confirmed by nuclear magnetic resonance (NMR) spectra, mass spectra (MS) and the like. Unless otherwise noted, the "part" and "%" are based on mass.

Synthetic Example 1

As shown in the reaction equations below, 118.53 g of 8-chloro-1-octanol, 110.36 g of methacrylic acid, 240 mg of 4-methoxyphenol, 6.84 g of p-toluenesulfonic acid monohydrate, 690 mL of cyclohexane and 140 mL of diisopropyl ether were mixed and refluxed for 8 hours by heating in an oil bath. After allowing the reaction liquid to cool to 30° C., 400 mL of water was added to the reaction liquid, and the organic layer was extracted. The organic layer was washed twice with 300 mL of a 5% aqueous sodium hydrogen carbonate solution and once with 300 mL of saturated brine. The obtained solution was concentrated and then purified by silica gel chromatography (eluent: a mixed solvent of hexane/ethyl acetate), and 132 g of 8-chlorooctyl methacrylate was obtained.

In 234 g of 10% hydrochloric acid, 26.33 g of 3,5-di-tert-butylaniline was suspended. Sodium nitrite in an amount of 13.27 g was dissolved in 130 mL of water, added to the suspension at 2 to 3° C. and stirred for a while at 2 to 3° C. Next, 13.27 g of phenol was dissolved in 204 g of a 25% aqueous sodium hydroxide solution, dropped at 0 to 2° C. and stirred for a while at 0 to 2° C. Concentrated hydrochloric acid in an amount of 53 mL was added at 2 to 7° C. Precipitates collected by filtration were purified by silica gel chromatography (eluent: a mixed solvent of hexane/ethyl acetate) and recrystallized with a mixed solvent of hexane and toluene, and 7.11 g of 3',5'-di-tert-butyl-4-hydroxyazobenzene was thus obtained as a yellow solid.

To 18 mL of DMF, 3.00 g of 3',5'-di-tert-butyl-4-hydroxyazobenzene, 2.39 g of potassium carbonate and 0.3 mg of methoxyphenol were mixed. 8-Chlorooctyl methacrylate in an amount of 2.37 g was dissolved in 5 mL of DMF and dropped to the mixture at 70 to 85° C. The mixture was stirred at 85° C. for 7.5 hours. After cooling to room temperature, water was added, followed by extraction with ethyl acetate. The organic layer was washed with 10% hydrochloric acid and then with water and dried over anhydrous sodium sulfate. After evaporating the solvent under reduced pressure, the remaining material was purified by silica gel chromatography (eluent: a mixed solvent of hexane/ethyl acetate), and 4.16 g of 8-(4-((3,5-di-tert-butylphenyl)diazenyl)phenoxy)octyl methacrylate (m1) was obtained.

[Chem. 47]

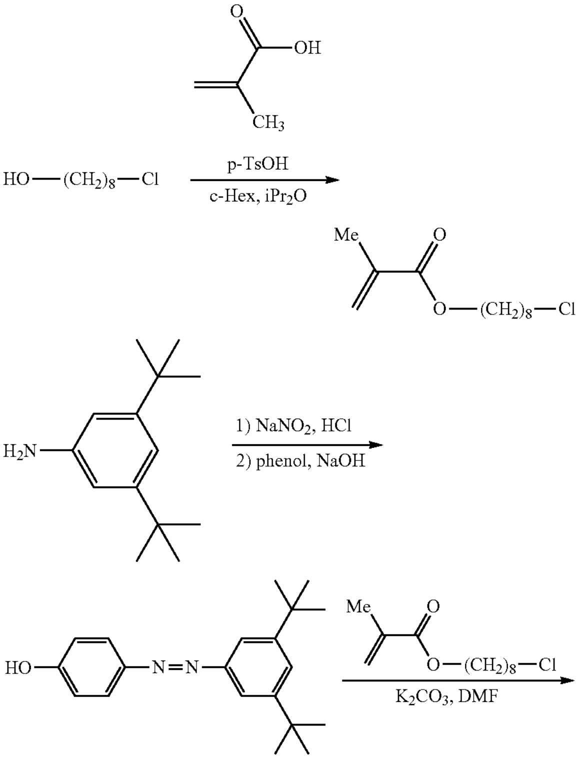

-continued

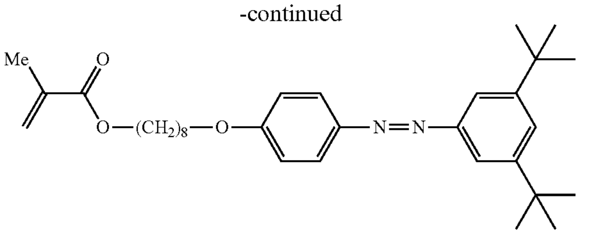

(ml)

Synthetic Example 2

As shown in the reaction equation below, 30.00 g of 3,5-dimethylaniline was suspended in 210 g of 3 N hydrochloric acid. Sodium nitrite in an amount of 17.10 g was dissolved in 120 mL of water, added to the suspension at 2 to 3° C. and stirred for a while at 2 to 3° C. Next, 23.30 g of phenol was dissolved in 270 g of a 10% aqueous sodium hydroxide solution, dropped at 0 to 2° C. and stirred for a while at 0 to 2° C. Concentrated hydrochloric acid in an amount of 50 mL was added at 2 to 7° C. Precipitates collected by filtration were purified by silica gel chromatography (eluent: a mixed solvent of hexane/ethyl acetate) and recrystallized with a mixed solvent of hexane and toluene, and 35.4 g of 3',5'-dimethyl-4-hydroxyazobenzene was thus obtained as a yellow solid.

To 54 mL of DMF, 6.00 g of 3',5'-dimethyl-4-hydroxyazobenzene, 6.05 g of potassium carbonate and 1.25 mg of methoxyphenol were mixed. 8-Chlorooctyl methacrylate in an amount of 6.30 g which was obtained as an intermediate in Synthetic Example 1 was dissolved in 6 mL of DMF and dropped to the mixture at 70 to 85° C. The mixture was stirred at 85° C. for 7.5 hours. After cooling to room temperature, water was added to cause crystallization. Crystals obtained by filtration were purified by silica gel chromatography (eluent: a mixed solvent of hexane/ethyl acetate) and recrystallized with a hexane solvent, and 8 g of 8-(4-((3,5-dimethylphenyl)diazenyl)phenoxy)octyl methacrylate (m2) was thus obtained.

[Chem. 48]

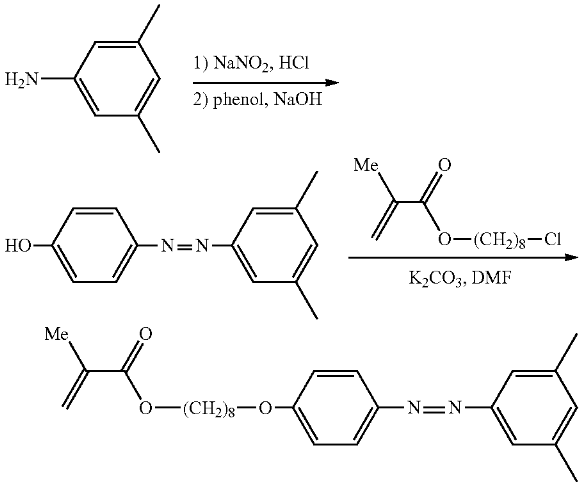

(m2)

Synthetic Example 3

As shown in the reaction equations below, 192.63 g of 6-chloro-1-hexanol, 235.40 g of acrylic acid, 468 mg of 4-methoxyphenol, 13.38 g of p-toluenesulfonic acid monohydrate, 1350 mL of cyclohexane and 270 mL of diisopropyl ether were mixed and refluxed for 8 hours by heating in an oil bath. After allowing the reaction liquid to cool to 30° C., 800 mL of water was added to the reaction liquid, and the organic layer was extracted. The organic layer was washed twice with 600 mL of a 5% aqueous sodium hydrogen carbonate solution and once with 600 mL of saturated brine. The obtained solution was concentrated and then purified by silica gel chromatography (eluent: a mixed solvent of hexane/ethyl acetate), and 260 g of 6-chlorohexyl acrylate was obtained.

1-Iodo-3-nitrobenzene in an amount of 50.00 g, 50 mL of triethylamine, 100 mL of DMF, 4.60 g of tetrakis(triphenylphosphine)palladium and 1.52 g of copper iodide were mixed. To the mixture, 13.67 g of 1-pentyne was dropped at 82 to 87° C. The mixture was stirred at 80° C. for 1.0 hour. After cooling to room temperature, ethyl acetate and water were added, and the liquids were separated. The obtained solution was concentrated and purified by silica gel chromatography (eluent: a mixed solvent of hexane/ethyl acetate), and 26.80 g of 1-nitro-3-(pent-1-yn-1-yl)benzene was thus obtained.

1-Nitro-3-(pent-1-yn-1-yl)benzene in an amount of 15.00 g, 1.50 g of 5 wt % palladium on carbon and 52 mL of ethanol were mixed and stirred at a hydrogen pressure of 0.5 MPa at 40° C. for 18 hours. The catalyst was removed by filtration, and the obtained solution was concentrated. Thus, 12.00 g of 3-pentylaniline was obtained.

3-Pentylaniline in an amount of 9.00 g was suspended in 18.00 g of 6 N hydrochloric acid. Sodium nitrite in an amount of 3.80 g was dissolved in 70 mL of water, added to the suspension at 2 to 3° C. and stirred for a while at 2 to 3° C. Next, 5.20 g of phenol was dissolved in 66 g of a 10% aqueous sodium hydroxide solution, dropped at 0 to 2° C. and stirred for a while at 0 to 2° C. Concentrated hydrochloric acid in an amount of 8 mL was added at 2 to 7° C. Next, ethyl acetate was added, and the liquids were separated, followed by washing. The obtained solution was concentrated and then purified by silica gel chromatography (eluent: a mixed solvent of hexane/ethyl acetate), and recrystallization with a mixed solvent of hexane and toluene was repeated. Thus, 5.00 g of 3'-pentyl-4-hydroxyazobenzene was obtained as a yellow solid.

To 40 mL of DMF, 4.00 g of 3'-pentyl-4-hydroxyazobenzene, 3.69 g of potassium carbonate and 1.00 mg of methoxyphenol were mixed. 6-Chlorohexyl acrylate in an amount of 3.64 g was dissolved in 4.0 mL of DMF and dropped to the mixture at 70 to 85° C. The mixture was stirred at 85° C. for 6 hours. After cooling to room temperature, water was added to cause crystallization. Crystals obtained by filtration were purified by silica gel chromatography (eluent: hexane) and recrystallized with a methanol solvent, and 5.1 g of 6-(4-(3-pentylphenyl diazenyl)phenoxy)hexyl acrylate (m3) was thus obtained.

[Chem. 49]

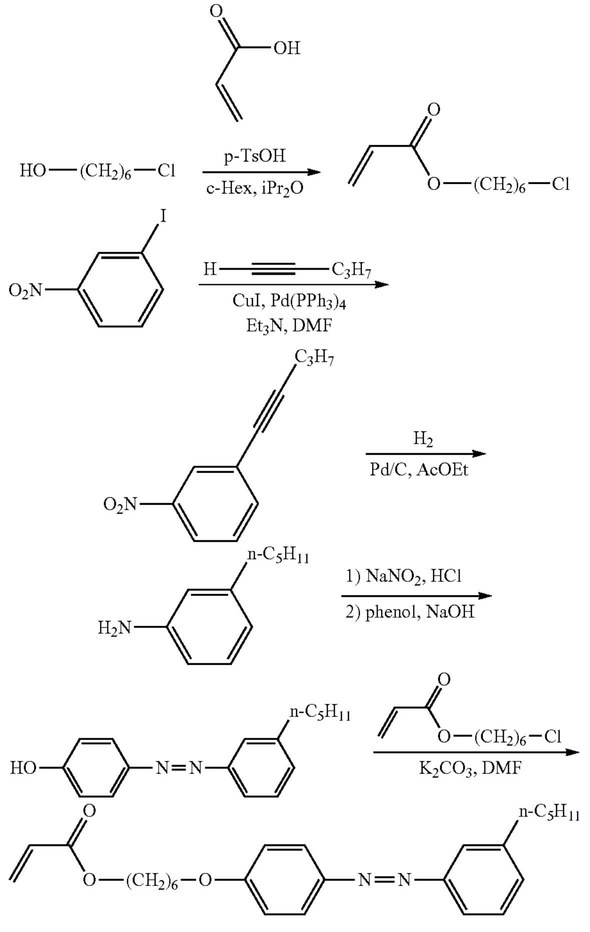

(m3)

Synthetic Example 4

As shown in the reaction equations below, 192.63 g of 6-chloro-1-hexanol, 242.40 g of methacrylic acid, 468 mg of 4-methoxyphenol, 13.38 g of p-toluenesulfonic acid monohydrate, 1350 mL of cyclohexane and 270 mL of diisopropyl ether were mixed and refluxed for 8 hours by heating in an oil bath. After allowing the reaction liquid to cool to 30° C., 800 mL of water was added to the reaction liquid, and the organic layer was extracted. The organic layer was washed twice with 600 mL of a 5% aqueous sodium hydrogen carbonate solution and once with 600 mL of saturated brine. The obtained solution was concentrated and then purified by silica gel chromatography (eluent: a mixed solvent of hexane/ethyl acetate), and 270 g of 6-chlorohexyl methacrylate was obtained.

p-Hydroxybenzaldehyde in an amount of 49.80 g, 99.20 g of potassium carbonate and 650 mL of DMF were mixed. To the mixture, 87.93 g of 6-chlorohexyl methacrylate was dropped at 90° C. The mixture was stirred at 90° C. for 6 hours. After cooling the reaction liquid to 10° C., 1300 mL of water was dropped to the reaction liquid, and a solid was precipitated. The solid was collected by filtration, and 116.26 g of 6-(4-formylphenoxy)hexyl methacrylate was obtained.

6-(4-Formylphenoxy)hexyl methacrylate in an amount of 116.14 g, 2100 mL of methanol, an aqueous sodium dihydrogen phosphate solution (obtained by dissolving 43 g of sodium dihydrogen phosphate dihydrate in 570 mL of water) and 73 mL of a 30% hydrogen peroxide solution were added one by one. An aqueous sodium chlorite solution (obtained by dissolving 61.9 g of sodium chlorite with the purity of 80% in 500 mL of water) was added by dropping. After dropping, the reaction liquid was stirred at 45° C. for 3 hours, and the reaction was finished. After slowly cooling the reaction liquid to 20° C., 2250 mL of water was dropped to the reaction liquid, and a solid was precipitated. The solid was collected by filtration, and 72.7 g of 4-((6-(methacryloyloxy)hexyl)oxy)benzoic acid was thus obtained.

4-((6-(Methacryloyloxy) hexyl)oxy)benzoic acid in an amount of 0.99 g, 1.00 g of 3',5'-di-tert-butyl-4-hydroxyazobenzene, 7.87 mg of 4-dimethylaminopyridine and 5 mL of dichloromethane were mixed. While the internal temperature was kept at 10° C. or lower, 0.49 g of diisopropylcarbodiimide was dropped, followed by stirring at 15-25° C. for 3 hours. Water was added to the reaction liquid to inactivate the reaction. The obtained precipitates were separated by filtration, and the obtained solution was purified by column chromatography (eluent: dichloromethane). Recrystallization was conducted with methanol after concentration, and 0.50 g of 4-((3,5-di-tert-butylphenyl)diazanyl)phenyl 4-((6-(methacryloyloxy)hexyl)oxy)benzoate (m4) was thus obtained.

[Chem. 50]

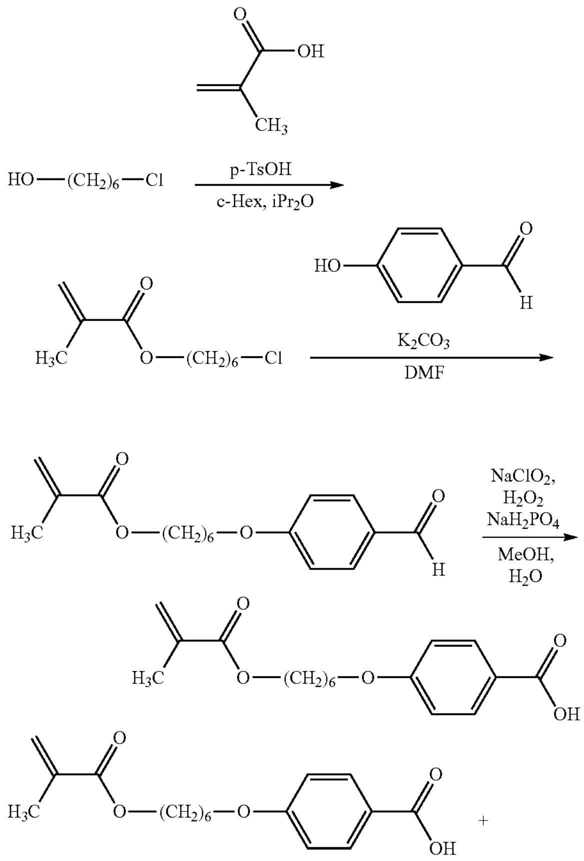

-continued

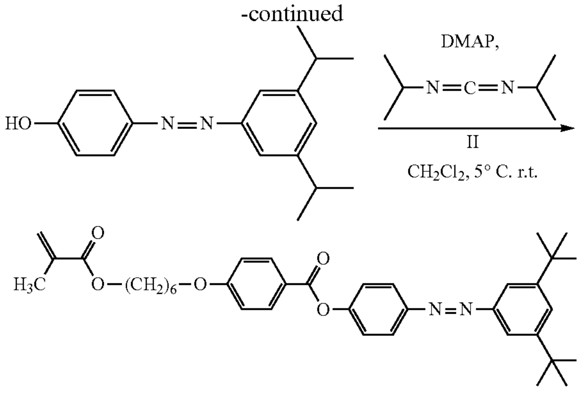

(m4)

Synthetic Example 51

As shown in the reaction equation below, 31.50 g of 5-nitroisophthalic acid, 1.09 g of DMF and 120 mL of $CH_2Cl_2$ were mixed. Oxalyl dichloride in an amount of 20.83 g was dropped to the mixture and then refluxed by heating for 2 hours. The obtained solution was concentrated, and 37.00 g of 5-nitroisophthaloyl dichloride was thus obtained.

5-Nitroisophthaloyl dichloride in an amount of 37.00 g and 120 mL of THF were mixed. tert-Butoxy potassium in an amount of 23.44 g was dissolved in 176 mL of THF and dropped to the mixture at 5-10° C. After reacting at room temperature for 2 hours, 200 mL of water and 400 mL of toluene were added, and the liquids were separated. The obtained solution was concentrated and purified by column chromatography (eluent: a mixed solvent of hexane/ethyl acetate), and 43.42 g of di-tert-butyl-5-nitroisophthalate was thus obtained.

Di-tert-butyl-5-nitroisophthalate in an amount of 40.00 g, 4.00 g of 5 wt % palladium on carbon and 160 mL of ethanol were mixed and stirred at a hydrogen pressure of 0.5 MPa at 40° C. for 10 hours. The catalyst was removed by filtration, and the obtained solution was concentrated. Thus, 34.50 g of di-tert-butyl-5-aminoisophthalate was obtained.

In 1.7 M hydrochloric acid, 15.00 g of di-tert-butyl-5-aminoisophthalate was suspended. Sodium nitrite in an amount of 3.53 g was dissolved in 35 mL of water, added to the suspension at 2 to 3° C. and stirred for a while at 2 to 3° C. Next, the mixture was diluted with 300 mL of MeOH. Phenol in an amount of 4.81 g was dissolved in an aqueous potassium hydroxide solution, dropped at 0 to 2° C. and stirred for a while at 0 to 2° C. After adding hydrochloric acid at 2 to 7° C., precipitates collected by filtration were purified by silica gel chromatography (eluent: a mixed solvent of hexane/ethyl acetate), and 6.32 g of di-tert-butyl 5-((4-hydroxyphenyl)diazenyl) isophthalate was thus obtained.

To 23 mL of DMF, 3.00 g of di-tert-butyl 5-((4-hydroxy-phenyl)diazenyl)isophthalate, 1.77 g of potassium carbonate and 0.5 mg of methoxyphenol were mixed. 8-Chlorooctyl methacrylate in an amount of 1.75 g which was obtained as an intermediate in Synthetic Example 1 was dissolved in 2 mL of DMF and dropped to the mixture at 70 to 85° C. The mixture was stirred at 85° C. for 7.5 hours. After cooling to room temperature, water was added, followed by extraction with ethyl acetate. The organic layer was washed with water and dried over anhydrous sodium sulfate. After evaporating the solvent under reduced pressure, the remaining material was purified by silica gel chromatography (eluent: a mixed solvent of hexane/ethyl acetate), and 2.69 g of di-tert-butyl 5-((4-((1-(methacryloyloxy)octyl)oxy)phenyl)diazanyl) isophthalate (m5) was obtained.

[Chem. 51]

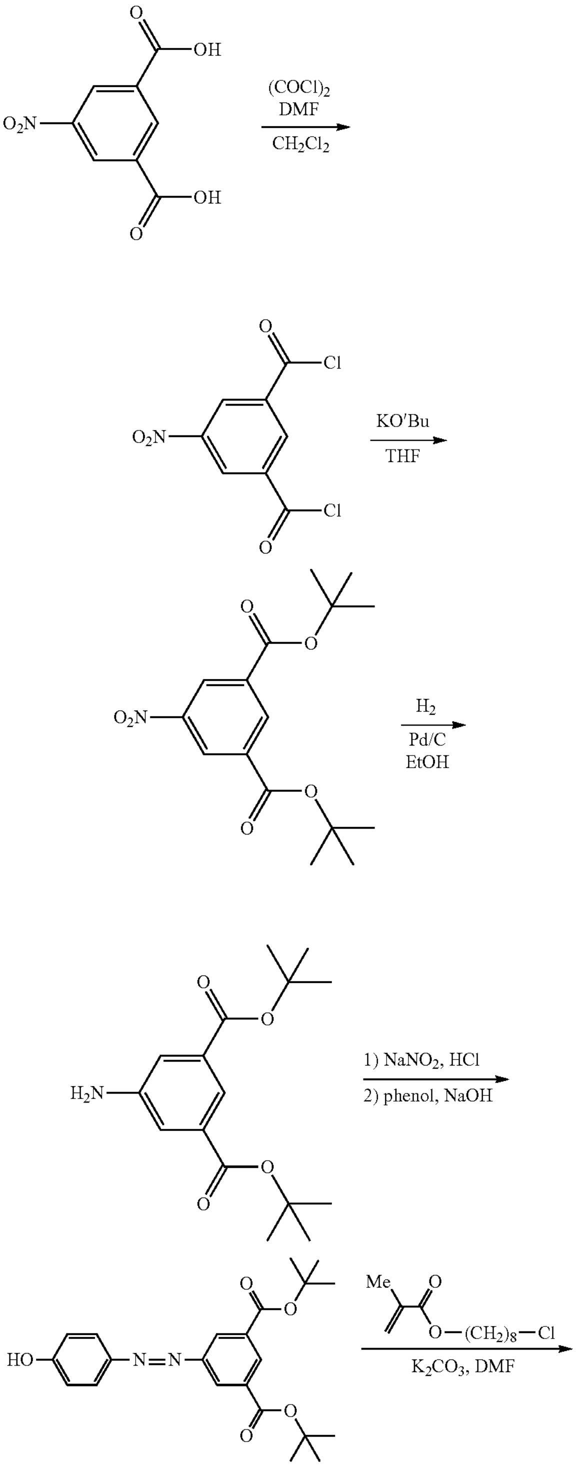

-continued

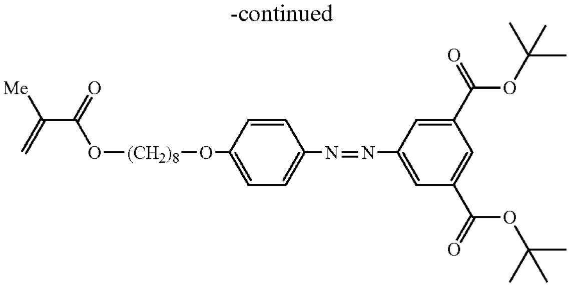

(m5)

Synthetic Example 6

As shown in the reaction equation below, 10.00 g of 3-(tert-butyl) aniline was suspended in 30 g of 6 N hydrochloric acid. Sodium nitrite in an amount of 4.62 g was dissolved in 80 mL of water, added to the suspension at 2 to 3° C. and stirred for a while at 2 to 3° C. Next, 6.30 g of phenol was dissolved in 80 g of a 10% aqueous sodium hydroxide solution, dropped at 0 to 2° C. and stirred for a while at 0 to 2° C., and then hydrochloric acid was added at 2 to 7° C. Precipitates collected by filtration were purified by silica gel chromatography (eluent: a mixed solvent of hexane/ethyl acetate) and recrystallized with a mixed solvent of hexane and toluene, and 10.22 g of 4-((3-(tert-butyl) phenyl)diazanyl)phenol was thus obtained.

To 45 mL of DMF, 5.00 g of 4-((3-(tert-butyl)phenyl) diazanyl)phenol, 4.62 g of potassium carbonate and 1.0 mg of methoxyphenol were mixed. 8-Chlorooctyl methacrylate in an amount of 4.58 g which was obtained as an intermediate in Synthetic Example 1 was dissolved in 5 mL of DMF and dropped to the mixture at 70 to 85° C. The mixture was stirred at 85° C. for 7.5 hours. After cooling to room temperature, water was added, followed by extraction with ethyl acetate. The organic layer was washed with 10% hydrochloric acid and then with water and dried over anhydrous sodium sulfate. After evaporating the solvent under reduced pressure, the remaining material was purified by silica gel chromatography (eluent: a mixed solvent of hexane/ethyl acetate), and 5.32 g of 8-(4-((3-tert-butylphenyl)diazenyl)phenoxy)octyl methacrylate (m6) was obtained.

[Chem. 52]

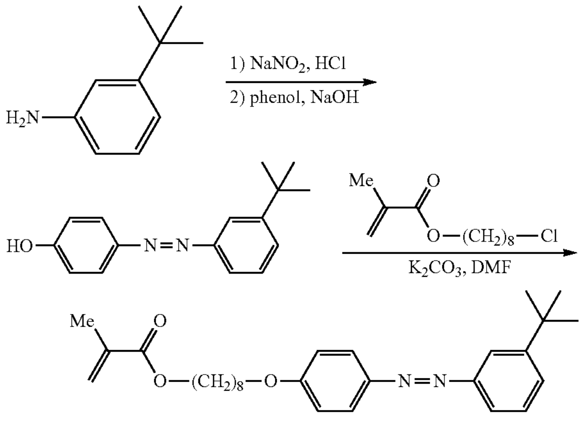

(m6)

Synthetic Example 7

As shown in the reaction equation below, 18.00 g of 3-isopropylaniline was suspended in 54 g of 6 N hydrochloric acid. Sodium nitrite in an amount of 9.18 g was dissolved in 145 mL of water, added to the suspension at 2 to 3° C. and stirred for a while at 2 to 3° C. Next, 12.53 g of phenol was dissolved in 130 g of a 10% aqueous sodium hydroxide solution, dropped at 0 to 2° C. and stirred for a while at 0 to 2° C., and then hydrochloric acid was added at 2 to 7° C. Precipitates collected by filtration were purified by silica gel chromatography (eluent: a mixed solvent of hexane/ethyl acetate) and recrystallized with a mixed solvent of hexane and toluene, and 20.80 g of 4-((3-isopropylphenyl)diazanyl) phenol was thus obtained.

To 90 mL of DMF, 10.00 g of 4-((3-isopropylphenyl) diazanyl)phenol, 9.78 g of potassium carbonate and 2.0 mg of methoxyphenol were mixed. 8-Chlorooctyl methacrylate in an amount of 9.68 g which was obtained as an intermediate in Synthetic Example 1 was dissolved in 10 mL of DMF and dropped to the mixture at 70 to 85° C. The mixture was stirred at 85° C. for 7.5 hours. After cooling to room temperature, water was added, followed by extraction with ethyl acetate. The organic layer was washed with 10% hydrochloric acid and then with water and dried over anhydrous sodium sulfate. After evaporating the solvent under reduced pressure, the remaining material was purified by silica gel chromatography (eluent: a mixed solvent of hexane/ethyl acetate), and 11.45 g of 8-(4-((3-isopropylphenyl)diazenyl)phenoxy)octyl methacrylate (m7) was obtained.

[Chem. 53]

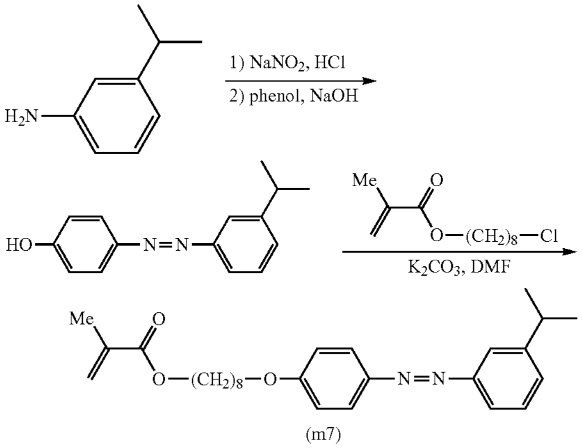

(m7)

Synthetic Example 8

As shown in the reaction equations below, 4.00 g of 6-aminohexan-1-ol, 5.7 mL of triethylamine and 40 mL of $CH_2Cl_2$ were mixed. Di-tert-butyl dicarbonate in an amount of 7.45 g was dropped to the mixture and stirred at 25° C. for 3 hours. Next, a saturated aqueous sodium hydrogen carbonate solution and ethyl acetate were added, and the liquids were separated. The obtained solution was concentrated and then purified by silica gel chromatography (eluent: a mixed solvent of hexane/ethyl acetate), and 7.20 g of tert-butyl-(6-hydroxyhexyl)carbamate was obtained.

In 234 g of 10% hydrochloric acid, 26.33 g of 3,5-di-tert-butylaniline was suspended. Sodium nitrite in an amount of 13.27 g was dissolved in 130 mL of water, added to the suspension at 2 to 3° C. and stirred for a while at 2 to 3° C. Next, 13.27 g of phenol was dissolved in 204 g of a 25% aqueous sodium hydroxide solution, dropped at 0 to 2° C. and stirred for a while at 0 to 2° C. Concentrated hydrochloric acid in an amount of 53 mL was added at 2 to 7° C. Precipitates collected by filtration were purified by silica gel chromatography (eluent: a mixed solvent of hexane/ethyl acetate) and recrystallized with a mixed solvent of hexane and toluene, and 7.11 g of 3',5'-di-tert-butyl-4-hydroxyazobenzene was thus obtained as a yellow solid.

tert-Butyl-(6-hydroxyhexyl)carbamate in an amount of 2.59 g, 3.70 g of 3',5'-di-tert-butyl-4-hydroxyazobenzene, 3.60 g of triphenylphosphine and 30 mL of THF were mixed. Diisopropyl azodicarboxylate in an amount of 2.65 g was dropped to the mixture at 5 to 10° C. and then stirred at 25° C. for 3 hours. After adding 1 mL of water, the reaction liquid was concentrated. By purifying by silica gel chromatography (eluent: a mixed solvent of hexane/ethyl acetate), 4.65 g of tert-butyl(6-(4-((3,5-di-tert-butylphenyl)diazanyl)phenoxy)hexyl)carbamate was obtained.

tert-Butyl(6-(4-((3,5-di-tert-butylphenyl)diazanyl)phenoxy)hexyl)carbamate in an amount of 3.00 g, 6 mL of trifluoroacetic acid and 15 mL of $CH_2Cl_2$ were mixed and stirred at 25° C. for 3 hours. After concentrating the reaction liquid, a saturated sodium hydrogen carbonate solution and ethyl acetate were added, and the liquids were separated. The obtained solution was concentrated, and 1.64 g of 6-(4-((3,5-di-tert-butylphenyl)diazanyl)phenoxy)hexan-1-amine was obtained.

6-(4-((3,5-Di-tert-butylphenyl)diazanyl)phenoxy)hexan-1-amine in an amount of 1.5 g, 0.2 mL of pyridine and 15 mL of $CH_2Cl_2$ were mixed. Methacryloyl chloride in an amount of 1.53 g was dropped to the mixture at 5 to 10° C. and then stirred at 25° C. for 3 hours. Next, 10% hydrochloric acid and ethyl acetate were added, and the liquids were separated. The obtained solution was concentrated and purified by silica gel chromatography (eluent: a mixed solvent of hexane/ethyl acetate), and 0.52 g of N-(6-(4-((3,5-di-tert-butylphenyl)diazanyl)phenoxy)hexyl)methacrylamide (m8) was thus obtained.

[Chem. 54]

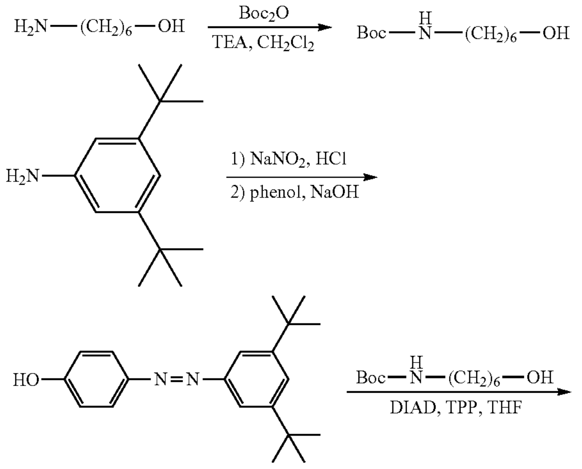

-continued

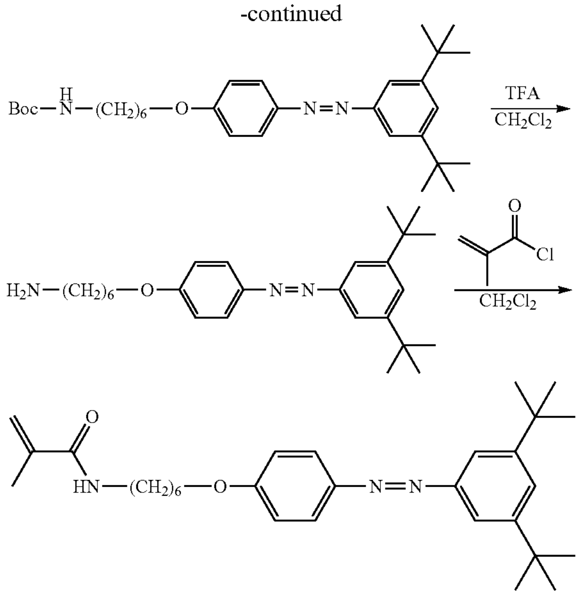

(m8)

Synthetic Example 9

As shown in the reaction equation below, 1 g of 3'-pentyl-4-hydroxyazobenzene which was obtained as an intermediate in Synthetic Example 3, 0.88 g of potassium carbonate and 0.2 mg of methoxyphenol were mixed to 8 mL of DMF. 6-Chlorohexyl methacrylate in an amount of 0.76 g was dissolved in 1 mL of DMF and dropped to the mixture at 70 to 85° C. The mixture was stirred at 85° C. for 6 hours. After cooling to room temperature, water was added to cause crystallization. Crystals obtained by filtration were purified by silica gel chromatography (eluent: hexane) and recrystallized with a methanol solvent, and 1.22 g of 6-(4-(3-pentylphenyl diazenyl)phenoxy)hexyl methacrylate (m9) was thus obtained.

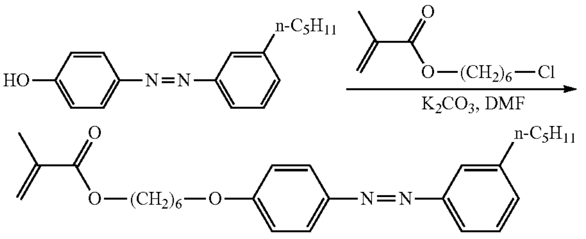

(m9)

Synthetic Example 10

As shown in the reaction equation below, 40 g of 2-(3-nitrophenyl)acetic acid, 1.60 g of DMF and 160 mL of $CH_2Cl_2$ were mixed. Oxalyl dichloride in an amount of 30.71 g was dropped to the mixture and then refluxed by heating for 2 hours. The obtained solution was concentrated, and 43.90 g of 2-(3-nitrophenyl)acetyl chloride was thus obtained.

2-(3-Nitrophenyl)acetyl chloride in an amount of 40.00 g and 200 mL of THF were mixed. tert-Butoxy potassium in an amount of 26.99 g was dissolved in 100 mL of THF and dropped to the mixture at 5-10° C. After reacting at room temperature for 2 hours, 200 mL of water and 600 mL of toluene were added, and the liquids were separated. The obtained solution was concentrated and purified by column chromatography (eluent: a mixed solvent of hexane/ethyl acetate), and 28.53 g of tert-butyl-2-(3-nitrophenyl)acetate was thus obtained.

tert-Butyl-2-(3-nitrophenyl)acetate in an amount of 25.00 g, 2.50 g of 5 wt % palladium on carbon and 150 mL of THF were mixed and stirred at a hydrogen pressure of 0.3 MPa at 25° C. for 6 hours. The catalyst was removed by filtration, and the obtained solution was concentrated. Thus, 21.0 g of tert-butyl-2-(3-aminophenyl)acetate was obtained.

In 88 mL of 10% hydrochloric acid, 20 g of tert-butyl-2-(3-aminophenyl)acetate was suspended. Sodium nitrite in an amount of 7.3 g was dissolved in 75 mL of water, added to the suspension at 2 to 3° C. and stirred for a while at 2 to 3° C. Next, a solution obtained by mixing 9.08 g of phenol, 40.9 g of sodium carbonate and 250 mL of water was dropped at 0 to 2° C. and stirred for a while at 0 to 2° C. After adding 10% hydrochloric acid at 2 to 7° C., precipitates collected by filtration were purified by silica gel chromatography (eluent: a mixed solvent of hexane/ethyl acetate), and 24.1 g of tert-butyl-2-(3-((4-hydroxyphenyl)diazanyl)phenyl)acetate was thus obtained.

To 300 mL of DMF, 20.00 g of tert-butyl-2-(3-((4-hydroxyphenyl)diazanyl)phenyl)acetate, 17.70 g of potassium carbonate and 4 mg of methoxyphenol were mixed. To the mixture, 17.88 g of 8-chlorooctyl methacrylate which was obtained as an intermediate in Synthetic Example 1 was dropped at 70 to 85° C. The mixture was stirred at 85° C. for 7.5 hours. After cooling to room temperature, water was added, and precipitates were obtained. The precipitates were filtered and purified by silica gel chromatography (eluent: a mixed solvent of hexane/ethyl acetate) and by recrystallization (EtOH), and 25.06 g of 8-(4-((3-(2-(tert-butoxy)-2-oxoethyl)phenyl)diazanyl)phenoxy)octyl methacrylate (m10) was obtained.

[Chem. 56]

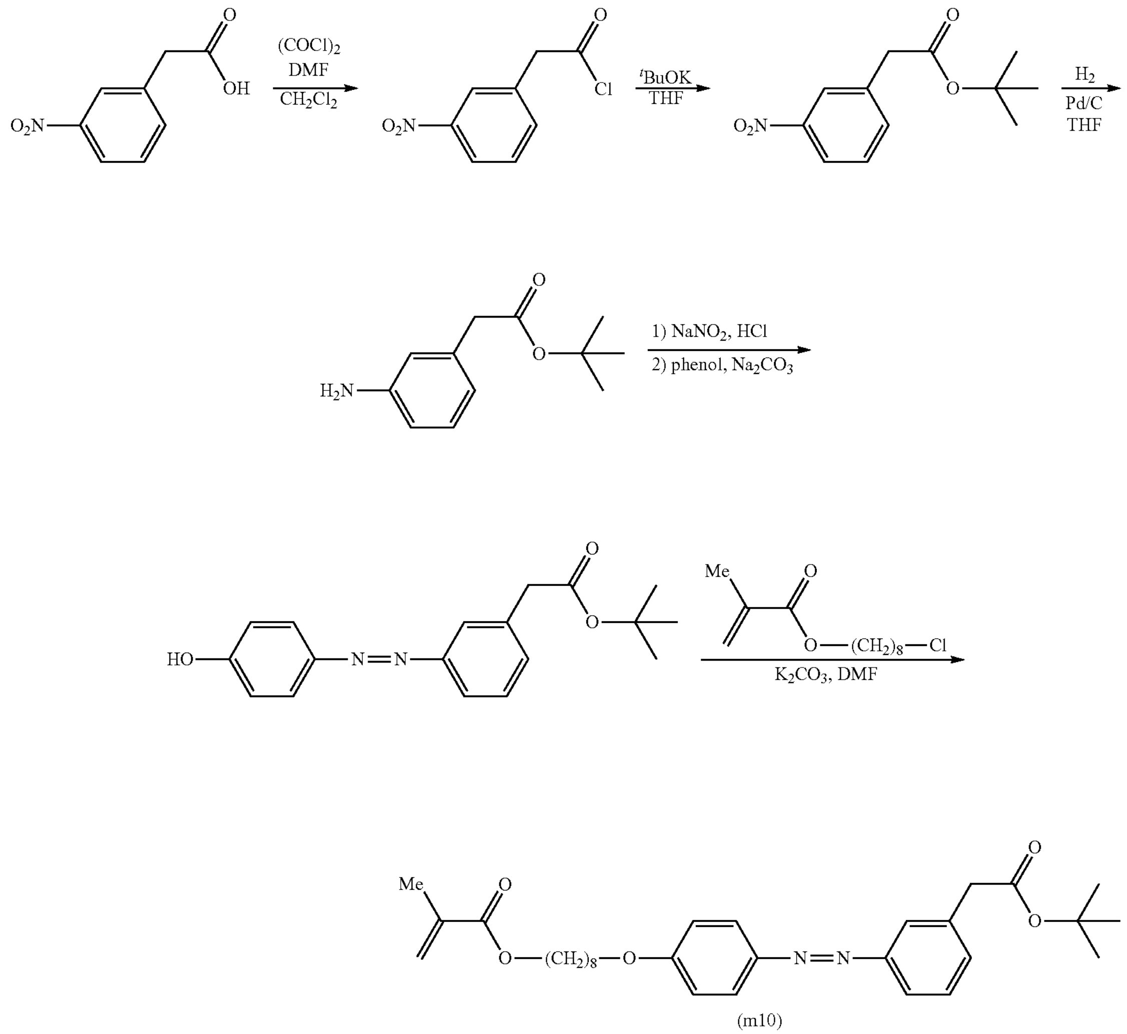

(m10)

Synthetic Example 11

As shown in the reaction equations below, 34 g of 10-bromo-1-decanol, 22 g of methacrylic acid, 70 mg of 4-methoxyphenol, 2 g of p-toluenesulfonic acid monohydrate, 200 mL of cyclohexane and 40 mL of diisopropyl ether were mixed and refluxed for 8 hours by heating in an oil bath. After allowing the reaction liquid to cool to 30° C., 100 mL of water was added to the reaction liquid, and the organic layer was extracted. The organic layer was washed twice with 100 mL of a 5% aqueous sodium hydrogen carbonate solution and once with 100 mL of saturated brine. The organic layer after washing was concentrated under reduced pressure, and 50 g of a compound (a-1-1), which was colorless liquid, was obtained. In a reactor, 23 g of p-hydroxybenzaldehyde, 46 g of potassium carbonate and 46 g of the compound (a-l-1) were suspended in 300 mL of DMF and stirred at 90° C. for 6 hours, and the reaction was finished. After cooling the reaction liquid to 10° C., 650 mL of water was dropped to the reaction liquid, and a solid was precipitated. The solid was collected by filtration, and 72 g of a compound (a-1-2), which was a brown granular solid, was obtained. In a reactor, 66 g of the compound (a-1-2) was dissolved in 980 mL of methanol, and an aqueous sodium dihydrogen phosphate solution (obtained by dissolving 19 g of sodium dihydrogen phosphate dihydrate in 250 mL of water) and a 30% hydrogen peroxide solution (32 mL) were added to the solution one by one. An aqueous sodium chlorite solution (obtained by dissolving 27 g of sodium chlorite with the purity of 80% in 220 mL of water) was added by dropping. After dropping, the reaction liquid was stirred at 45° C. for 3 hours, and the reaction was finished. After slowly cooling the reaction liquid to 20° C., water was dropped to the reaction liquid, and a solid was precipitated. The solid was collected by filtration, and the solid was washed by sprinkling water over the solid. The thus-obtained crude product of colorless scaly crystals was dried under reduced pressure for 8 hours, and 47 g of a compound (a-1-3), which was colorless crystals, was obtained. Separately, 54 g of 1-ethyl-3-(3-dimethylaminopropyl)carbodiimide hydrochloride and 0.3 g of 4-dimethylaminopyridine were dissolved in 406 mL of 2-cyanoethanol. A solution obtained by dissolving 50 g of ferulic acid in 203 mL of 2-cyanoethanol was dropped to the solution at 10° C. over an hour, and the obtained solution was stirred at room temperature for 4 hours. After mixing the reaction liquid and cold water at 15° C., a mixed solvent of toluene/THF was added to the mixture liquid, and the organic layer was extracted. The organic layer was washed with 200 mL of saturated brine and then concentrated, and the obtained yellow solid was recrystallized. Thus, 37 g of a compound (a-1-4), which was a white solid, was obtained.

In 140 mL of dichloromethane, 39 g of the compound (a-1-3), 28 g of the compound (a-1-4) and 0.3 g of 4-dimethylaminopyridine were suspended, and 172 g of diisopropylcarbodiimide was dropped while the internal temperature was kept at 10° C. or lower, followed by stirring at 15 to 25° C. for 3 hours. After confirming that the raw materials disappeared, water was added to the reaction liquid to inactivate the reaction. The obtained precipitates were separated by filtration, and a dichloromethane solution containing the precipitates was prepared and then purified by column chromatography. After evaporating dichloromethane from the dichloromethane solution under reduced pressure, methanol was added, and crystals were precipitated by cooling to 0° C. The crystals were collected by filtration and dried under reduced pressure, and 51 g of a cinnamate methacrylate monomer (a-1) was obtained.

[Chem. 57]

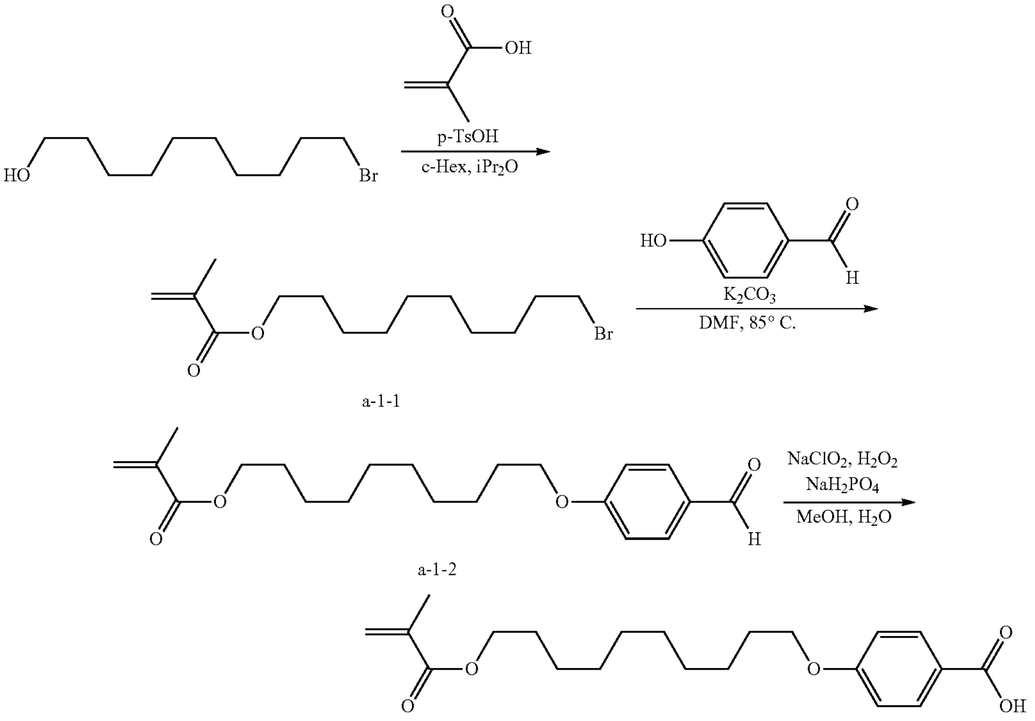

a-1-1 a-1-2 a-1-3

-continued

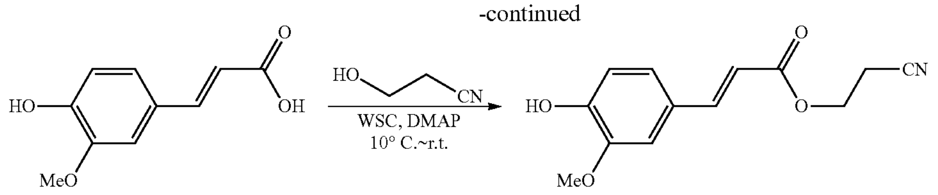

a-1-4

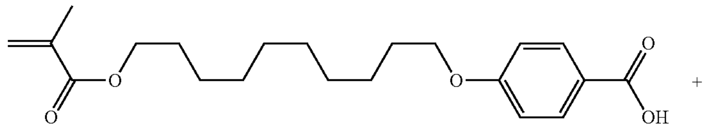

a-1-3

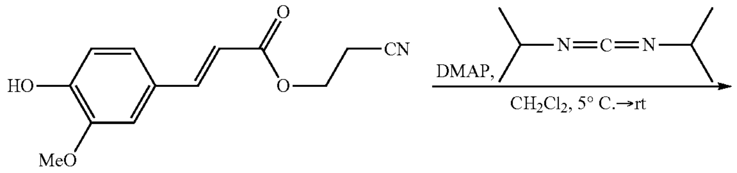

a-1-4

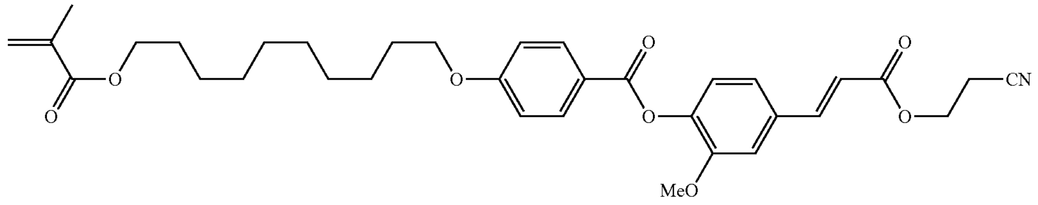

a-1

Synthetic Example 12

As shown in the reaction equation below, 0.2477 g of (m1) obtained in Synthetic Example 1, 5.00 g of 4-((E)-2-(2-methoxyethoxy) carbonylethenyl-1-yl)-2-methoxyphenyl 4-((6-(methacryloyloxy) hexyl)oxy)benzoate which was synthesized by the same method as that described in WO2013/002224 and 16.0 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The then 2.70 g of a copolymer (p1) was obtained by drying under reduced pressure. The molecular weights thereof, which were measured by gel permeation chromatography (GPC), were Mw=327,529 and Mw/Mn=2.34.

[Chem. 58]

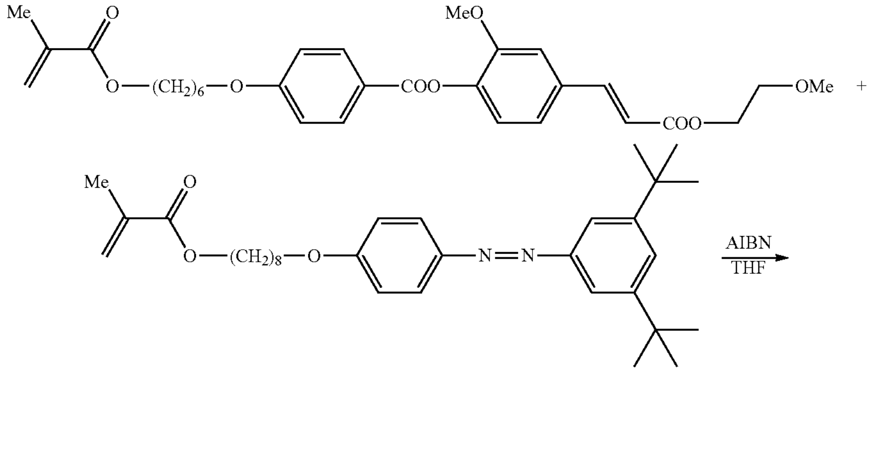

-continued

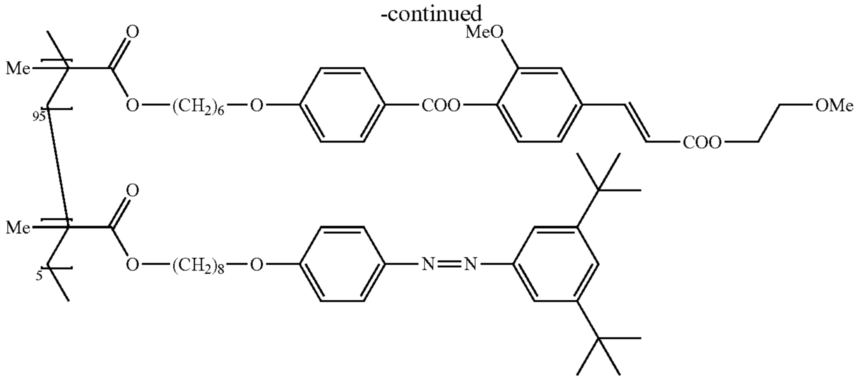

(p1)

Synthetic Example 13

As shown in the reaction equation below, 0.1350 g of (m1) obtained in Synthetic Example 1, 3.00 g of (a-1) obtained above and 8.8 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 1.46 g of a copolymer (p2) was obtained by drying under reduced pressure. The molecular weights thereof, which were measured by gel permeation chromatography (GPC), were Mw=337,529 and Mw/Mn=2.55.

[Chem. 59]

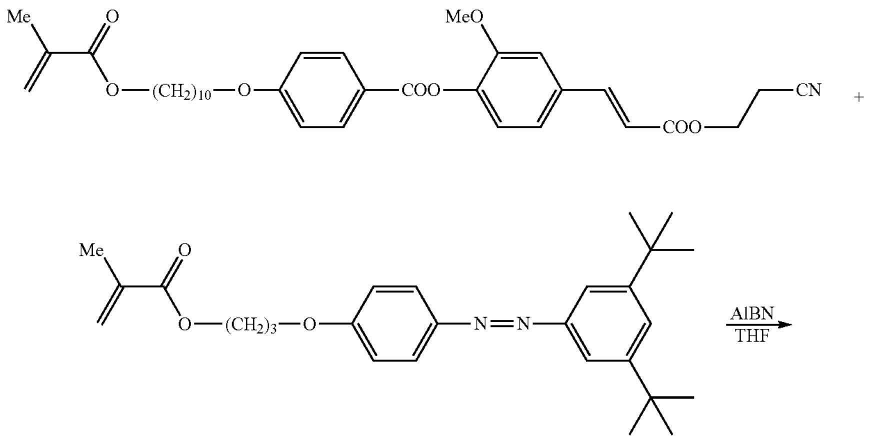

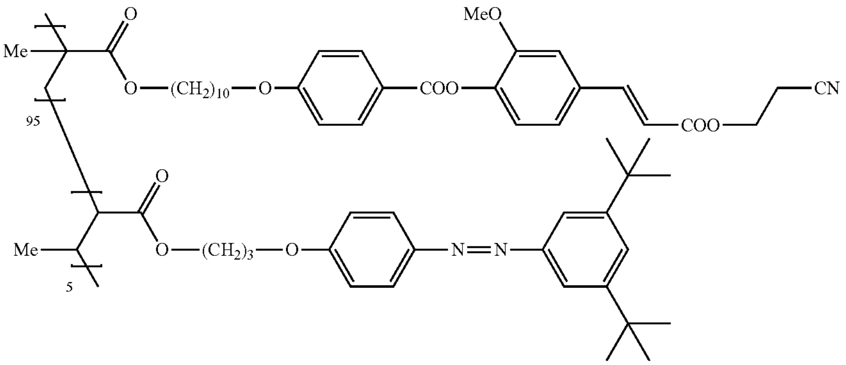

(p2)

Synthetic Example 14

As shown in the reaction equation below, 0.2856 g of (m1) obtained in Synthetic Example 1, 2.00 g of (a-1) obtained above and 26.1 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 1.00 g of a copolymer (p3) was obtained by drying under reduced pressure. The molecular weights thereof, which were measured by gel permeation chromatography (GPC), were Mw=184,527 and Mw/Mn=2.24.

[Chem. 60]

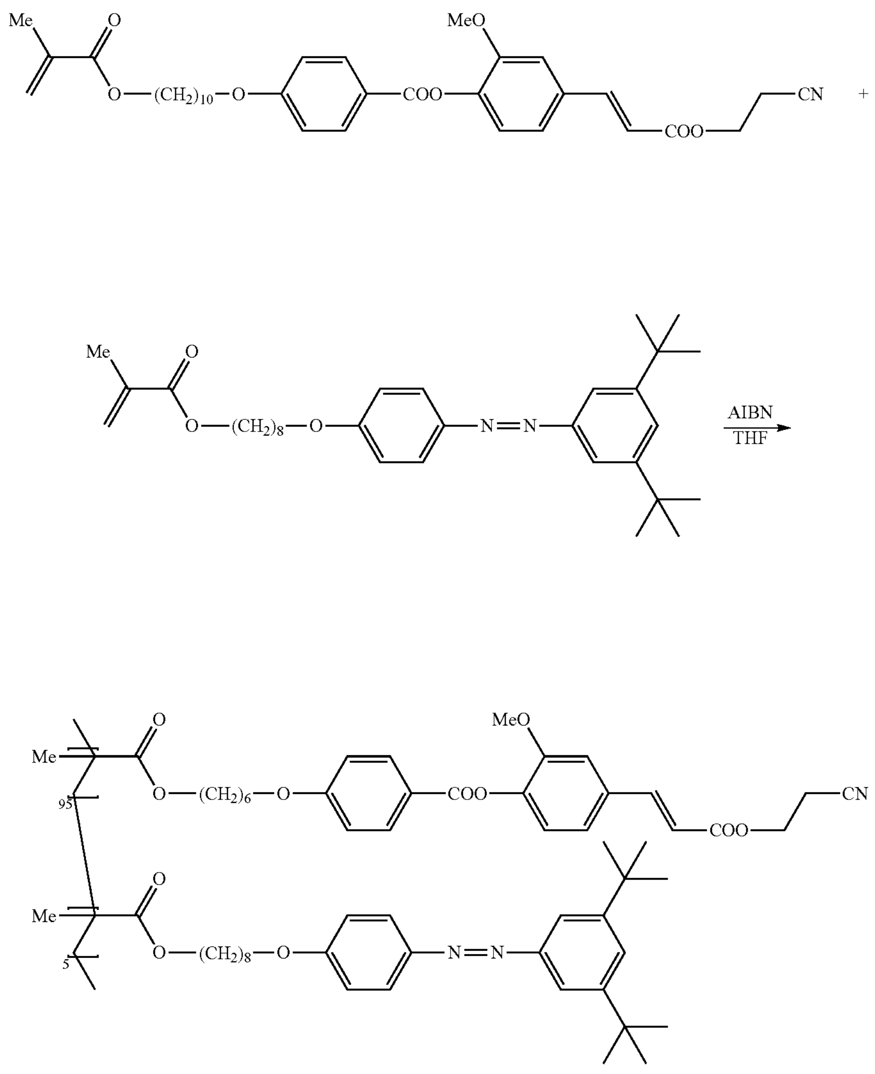

(p3)

Synthetic Example 15

As shown in the reaction equation below, 0.1130 g of (m2) obtained in Synthetic Example 2, 3.00 g of (a-1) obtained above and 8.8 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.56 g of a copolymer (p4) was obtained by drying under reduced pressure. The molecular weights thereof, which were measured by gel permeation chromatography (GPC), were Mw=185,104 and Mw/Mn=1.96.

[Chem. 61]

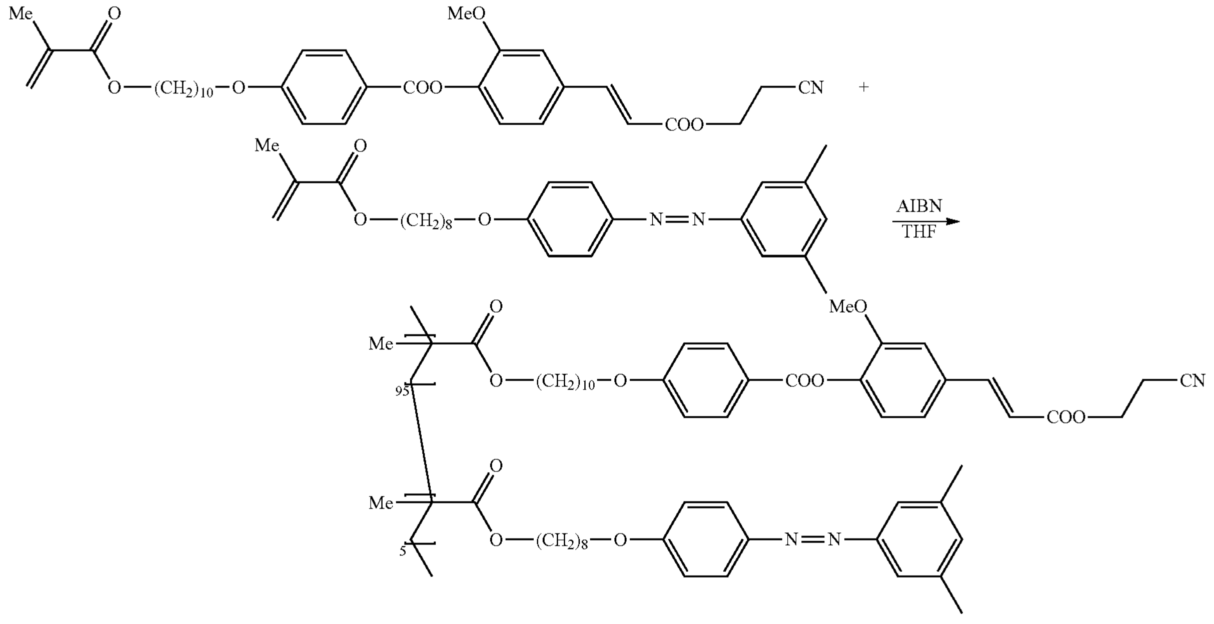

(p4)

Synthetic Example 16

As shown in the reaction equation below, 0.188 g of 6-(4-(3-pentylphenyl diazenyl) phenoxy)hexyl acrylate (m3) obtained in Synthetic Example 3, 5.00 g of (a-1) obtained above and 14.6 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 1.56 g of a copolymer (p5) was obtained by drying under reduced pressure. The molecular weights thereof, which were measured by gel permeation chromatography (GPC), were Mw=288,886 and Mw/Mn=2.73.

[Chem. 62]

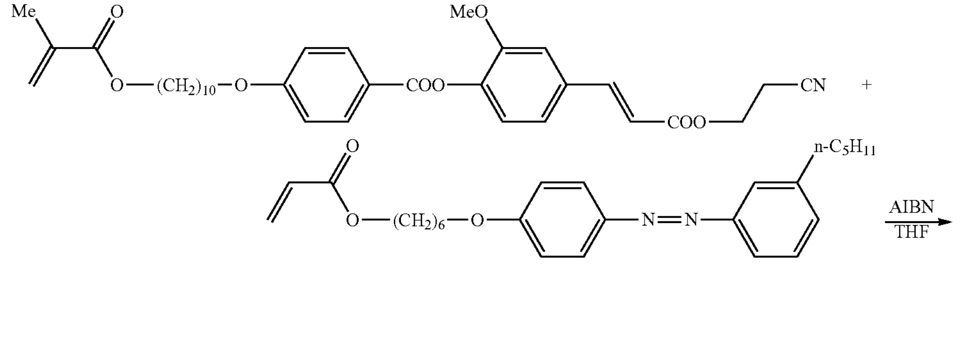

-continued

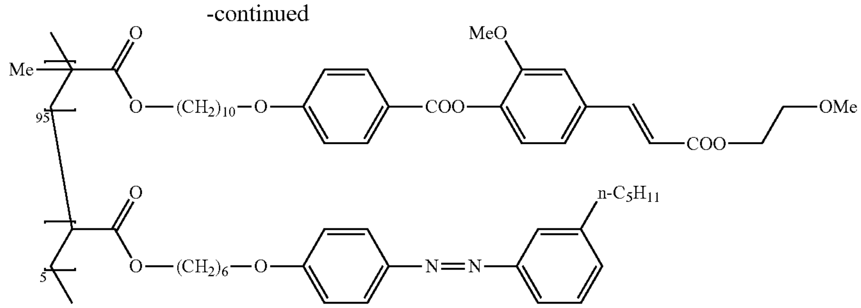

(p5)

Synthetic Example 17

As shown in the reaction equation below, 0.090 g of (m4) obtained in Synthetic Example 4, 1.69 g of (a-1) obtained above and 9.2 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.75 g of a copolymer (p6) was obtained by drying under reduced pressure. The molecular weights thereof, which were measured by gel permeation chromatography (GPC), were Mw=247842 and Mw/Mn=2.16.

[Chem. 63]

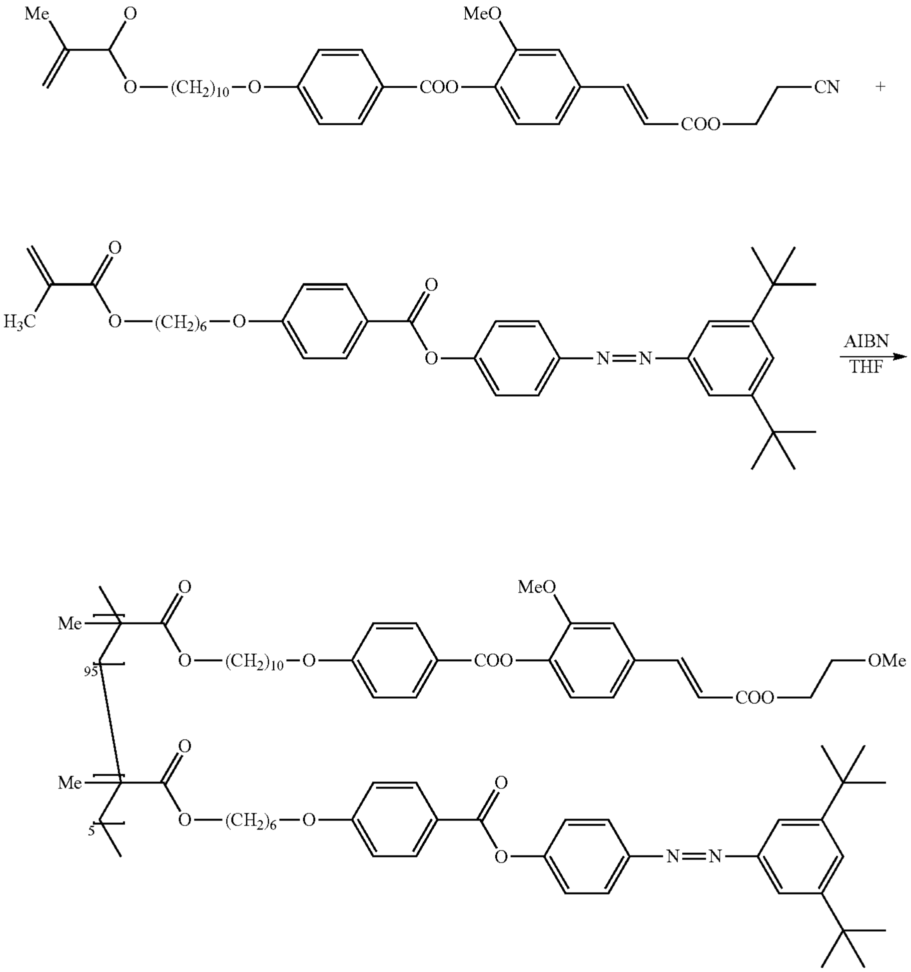

(P6)

Synthetic Example 18

As shown in the reaction equation below, 0.100 g of (m5) obtained in Synthetic Example 5, 1.89 g of (a-1) obtained above and 9.8 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.70 g of a copolymer (p7) was obtained by drying under reduced pressure. The molecular weights thereof, which were measured by gel permeation chromatography (GPC), were Mw=198756 and Mw/Mn=2.30.

[Chem. 64]

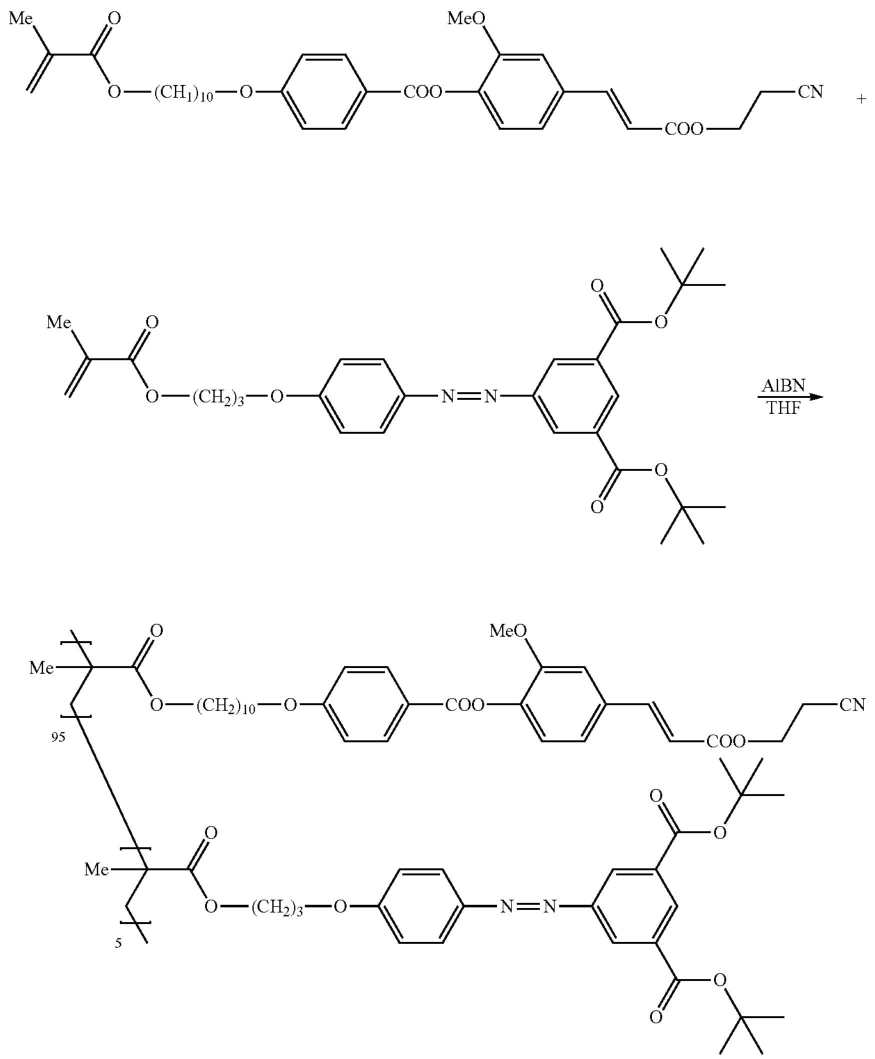

(p7)

Synthetic Example 19

As shown in the reaction equation below, 0.250 g of (m6) obtained in Synthetic Example 6, 6.23 g of (a-1) obtained above and 22.3 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 1.90 g of a copolymer (p8) was obtained by drying under reduced pressure. The molecular weights thereof, which were measured by gel permeation chromatography (GPC), were Mw=224529 and Mw/Mn=2.26.

[Chem. 65]

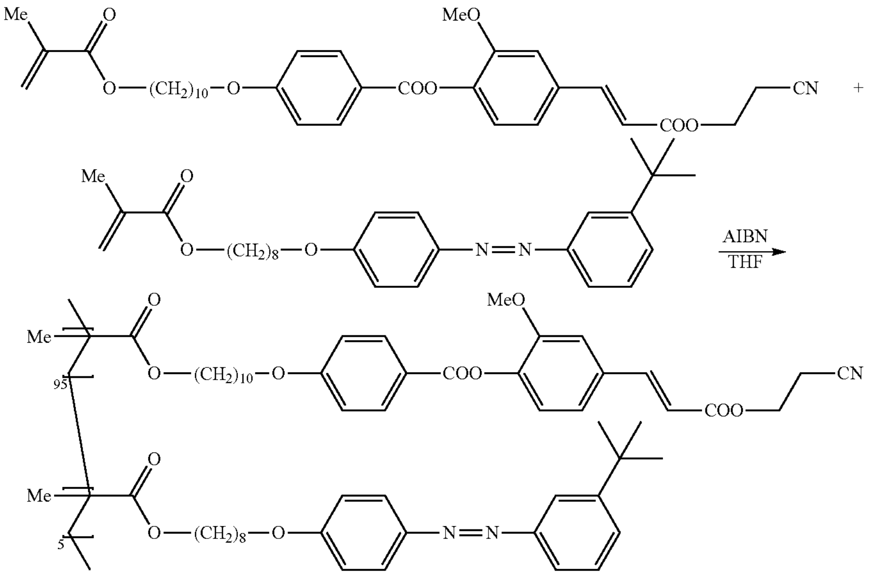

(p8)

Synthetic Example 20

As shown in the reaction equation below, 0.200 g of (m7) obtained in Synthetic Example 7, 5.15 g of (a-1) obtained above and 21.0 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 1.76 g of a copolymer (p9) was obtained by drying under reduced pressure. The molecular weights thereof, which were measured by gel permeation chromatography (GPC), were Mw=239812 and Mw/Mn=2.09.

[Chem. 66]

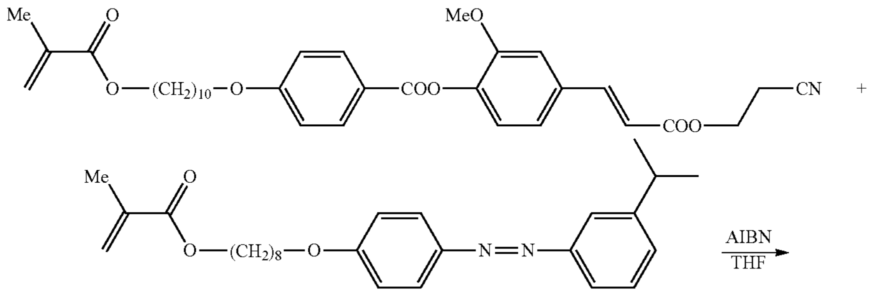

-continued

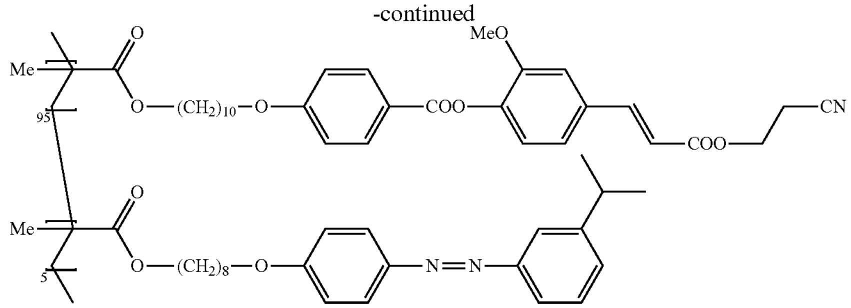

(p9)

Synthetic Example 21

As shown in the reaction equation below, 0.085 g of (m8) obtained in Synthetic Example 8, 2.00 g of (a-1) obtained above and 7.5 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.40 g of a copolymer (p10) was obtained by drying under reduced pressure. The molecular weights thereof, which were measured by gel permeation chromatography (GPC), were Mw=258116 and Mw/Mn=2.13.

[Chem. 67]

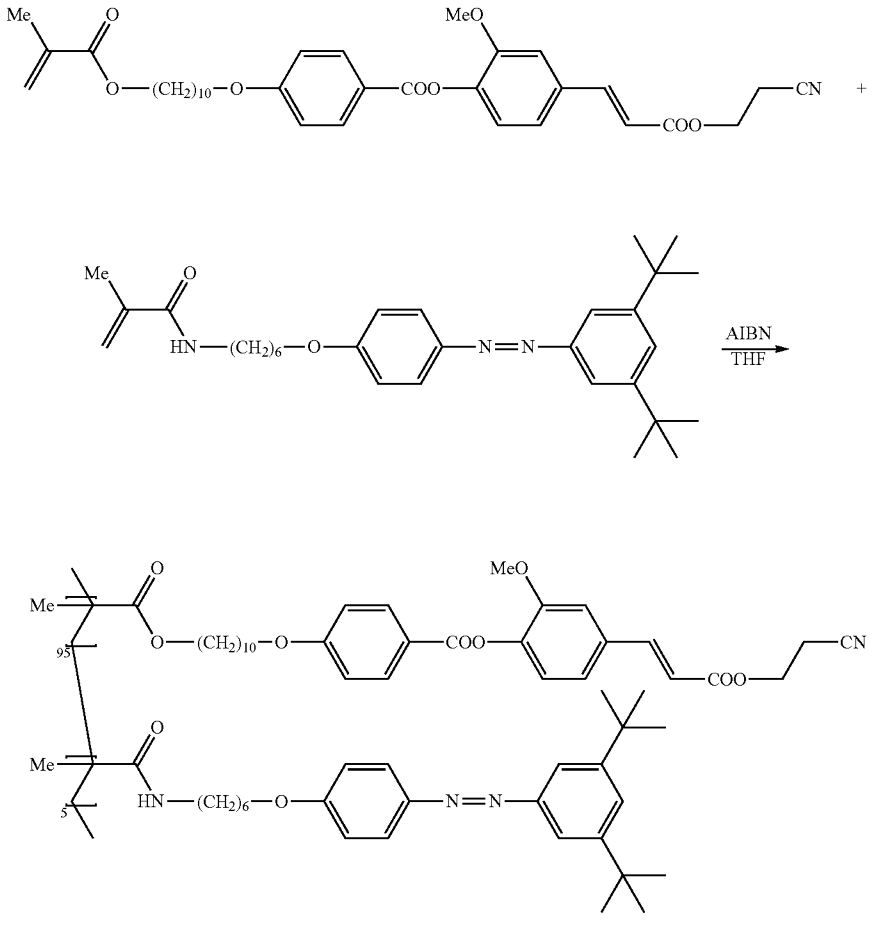

(p10)

Synthetic Example 22

As shown in the reaction equation below, 0.174 g of (m9) obtained in Synthetic Example 9, 2.00 g of (a-1) obtained above and 24.68 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.90 g of a copolymer (p11) was obtained by drying under reduced pressure. The molecular weights thereof, which were measured by gel permeation chromatography (GPC), were Mw=237,825 and Mw/Mn=2.10.

[Chem. 68]

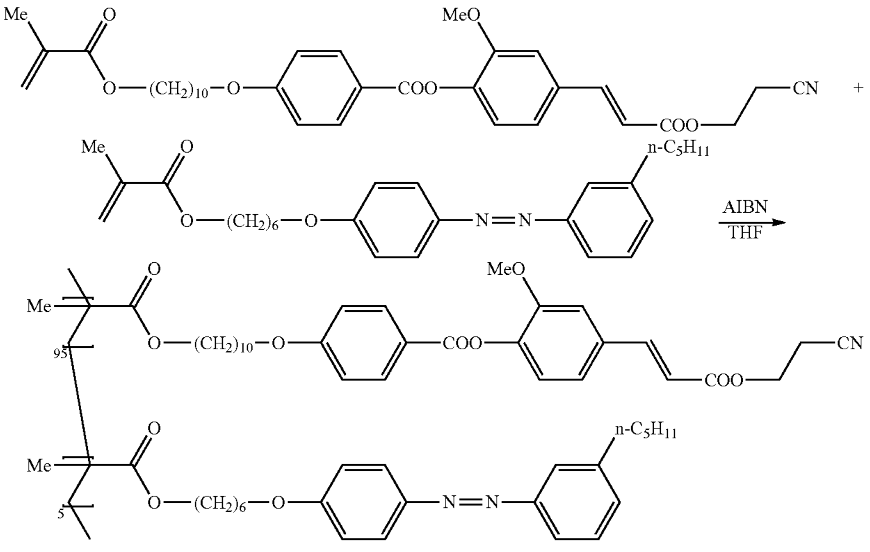

p11

Synthetic Example 23

As shown in the reaction equation below, 0.100 g of (m10) obtained in Synthetic Example 10, 2.21 g of (a-1) obtained above and 11.0 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.50 g of a copolymer (p12) was obtained by drying under reduced pressure. The molecular weights thereof, which were measured by gel permeation chromatography (GPC), were Mw=265371 and Mw/Mn=2.29.

[Chem. 69]

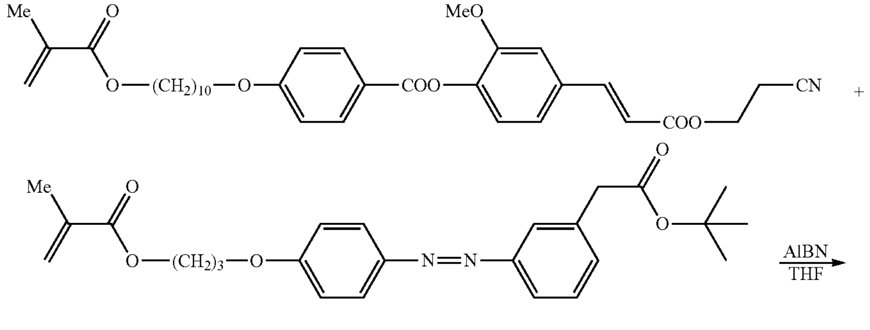

-continued

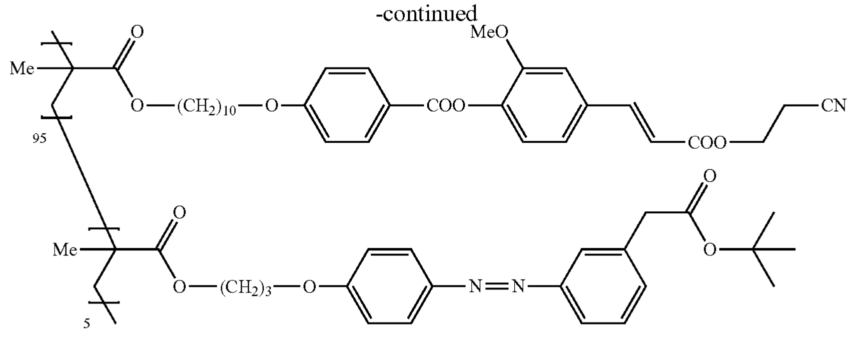

(p12)

Synthetic Example 24

As shown in the reaction equation below, 0.235 g of (m3) obtained in Synthetic Example 3, 3.00 g of (a-1) obtained above, 0.171 g of 4-((6-(methacryloyloxy)hexyl)oxy)benzoic acid which was obtained as an intermediate in Synthetic Example 4 and 20.3 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.90 g of a copolymer (p13) was obtained by drying under reduced pressure. The molecular weights thereof, which were measured by gel permeation chromatography (GPC), were Mw=192,727 and Mw/Mn=2.02.

[Chem. 70]

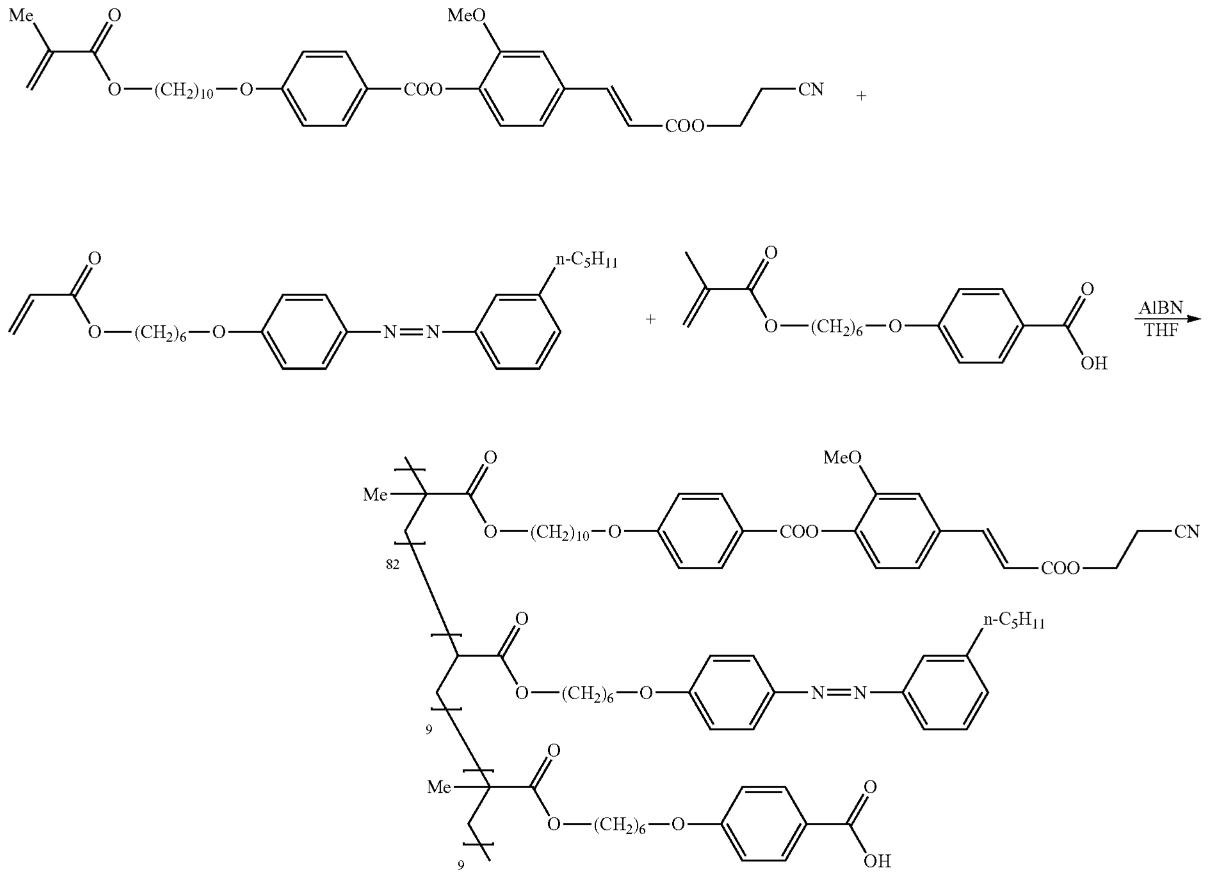

(p13)

Synthetic Example 25

As shown in the reaction equation below, 0.286 g of (m3) obtained in Synthetic Example 3, 3.65 g of (a-1) obtained above, 0.068 g of N-(methoxymethyl) acrylamide and 24.7 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.69 g of a copolymer (p14) was obtained by drying under reduced pressure. The molecular weights thereof, which were measured by gel permeation chromatography (GPC), were Mw=207,632 and Mw/Mn=2.37.

[Chem. 71]

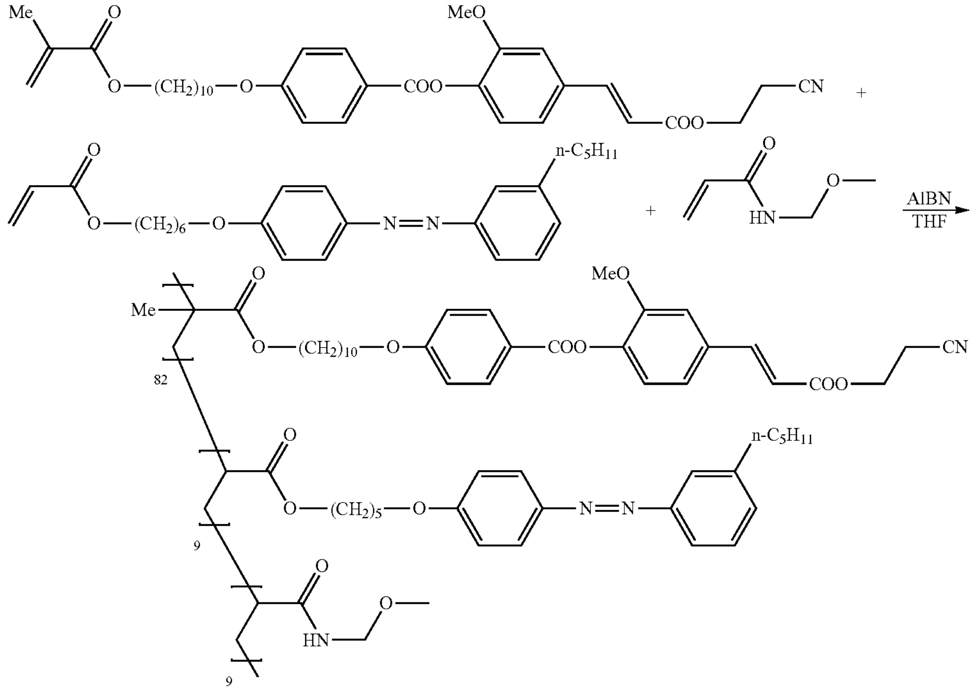

(p14)

Synthetic Example 26

As shown in the reaction equation below, 0.250 g of (m1) obtained in Synthetic Example 1, 2.66 g of (a-1) obtained above, 0.064 g of 2-hydroxyethyl methacrylate and 18 mg of AIBN were dissolved in THF and reacted in a nitrogen atmosphere at 60° C. Then, the reaction mixture was cooled to room temperature and added to hexane, and the polymerization product was precipitated. The solvent was removed by decantation, and the precipitates were dissolved again in THF and precipitated with hexane. The decantation operation was further conducted seven times, and then 0.75 g of a copolymer (p15) was obtained by drying under reduced pressure. The molecular weights thereof, which were measured by gel permeation chromatography (GPC), were Mw=223567 and Mw/Mn=2.41.

[Chem. 72]

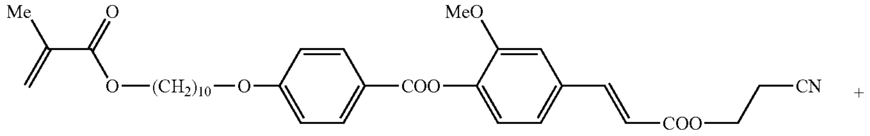

-continued

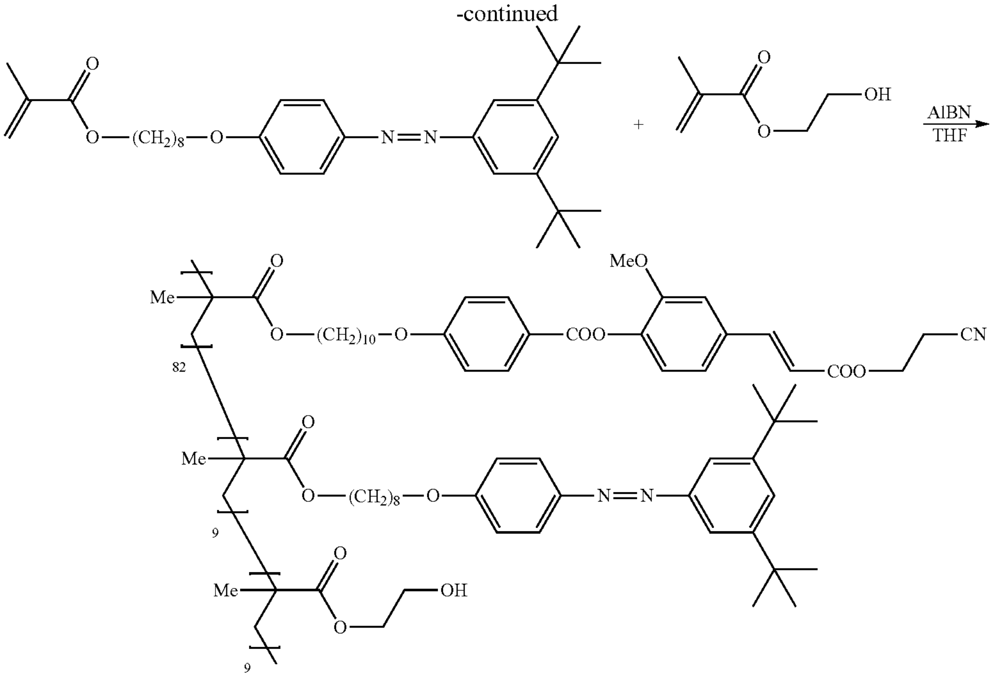

(p15)

Synthetic Example 27

As shown in the reaction equations below, the compound represented by the formula (33) was put into a reactor having a thermometer and a stirrer, suspended in an aqueous hydrochloric acid solution, reacted with sodium nitrite while ice cooling and then reacted with phenol and sodium hydroxide, and the compound represented by the formula (34) was obtained.

The compound represented by the formula (4) and potassium carbonate were added to the reactor having a thermometer and a stirrer and reacted with the compound represented by the formula (34), and the compound represented by the formula (ref-m) was obtained.

[Chem. 73]

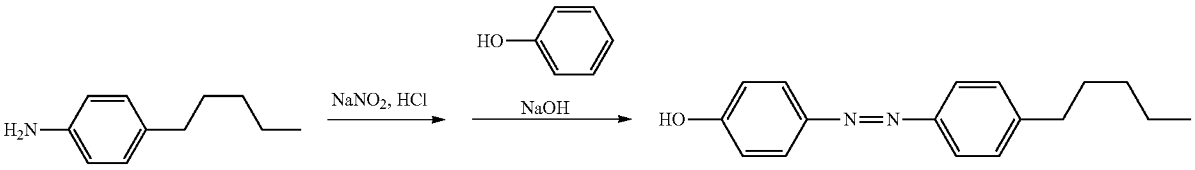

(33)

(34)

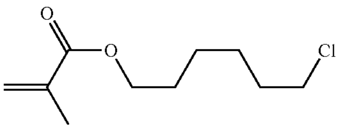

(4)

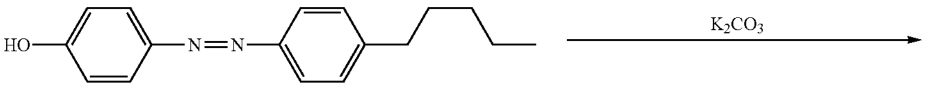

(34)

-continued

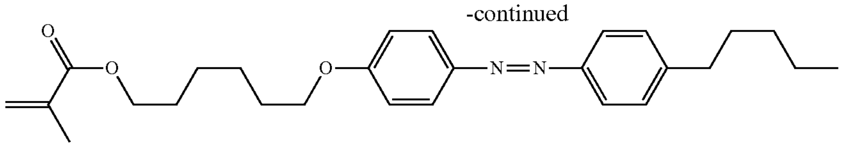

ref-m

In a flask, 20.0 g of the monomer (a-1), 0.78 g of the monomer (ref-m), 55.5 mg of AIBN and 80 mL of tetrahydrofuran (THF) were mixed and stirred in a nitrogen atmosphere at 55° C. for 7 hours. Then, hexane in an amount which was five times more than the amount of the monomers used (5 mL per 1 g of the monomers) (100 mL in this Synthetic Example) was added to precipitate the reaction mixture, and the supernatant was removed by decantation. The reaction mixture was dissolved again in THF in an amount which was three times more than the amount of the monomers used (3 mL per 1 g of the monomers) (60 mL in this Synthetic Example), and hexane in an amount which was five times more than the amount of the monomers used (5 mL per 1 g of the monomers) (100 mL in this Synthetic Example) was added to precipitate the reaction mixture. The supernatant was removed by decantation. The operations of re-dissolution in THF, precipitation with hexane and decantation were further conducted three times. Then, the obtained reaction mixture was dried under reduced pressure in a shaded environment at 20° C. at 0.13 kPa for 24 hours, and 9.1 g of (Ref-p) below was obtained.

The molecular weights of the obtained polymer were determined by gel permeation chromatography (GPC) under the conditions described below. The weight-average molecular weight (Mw) was 235,306 on polystyrene basis, and the distribution ratio (Mw/Mn) was 2.16. The residual monomer amount was 0.24%.

[Chem. 74]

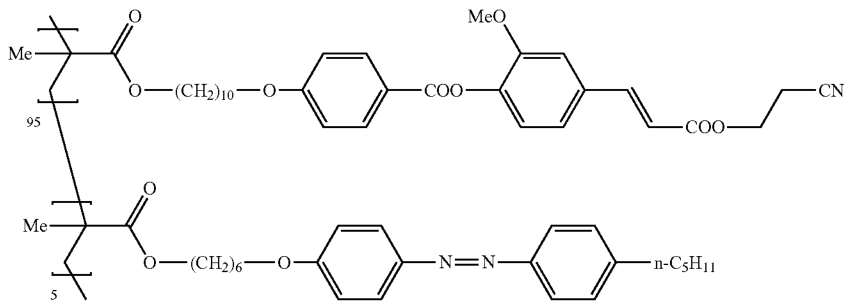

Ref-p

Example 1

A polymer solution for a photo-alignment film was obtained by dissolving the copolymer (p1) in N-methyl-2-pyrrolidone (NMP below), then adding 2-butoxyethanol, adjusting the weight ratio to become NMP:2-butoxyethanol: P1=47.5:47.5:5 and filtering using MS PTFE syringe filter (5 μm, 1 μm, 0.45 μm) manufactured by Membrane Solutions Limited. The solution was spin coated on an IPS3035-2up substrate manufactured by FPD Solution and a facing substrate to thicknesses of about 90 nm using a spin coater IH-DX-2 manufactured by Mikasa Co., Ltd. Then, the solution was dried on a digital hot plate NINOS ND1 manufactured by AS ONE at 80° C. for 3 minutes and further dried using an oven DO-600FA manufactured by AS ONE in an air atmosphere at 150° C. for 5 minutes. After drying, the films were slowly cooled to room temperature. Next, linearly polarized light of 313 nm with an irradiance of 20 mw/$cm^2$ was applied to the dried films for 7.5 seconds at 150 mJ/cm using a polarized light irradiator manufactured by Mejiro Precision, and photo-alignment films of Example 1 were produced.

With respect to the substrates on which the photo-alignment films were formed, Structbond XN-21-S manufactured by Mitsui Chemicals, Inc. was applied to the IPS3035-2up substrate side using a seal dispenser shot-mini manufactured by Musashi Engineering, Inc. Then, the sealing agent was dried at 90° C. for 30 minutes, and the substrates were pasted together. After pasting the substrates together, a glass cell was produced by pressing and heating at 150° C. for 90 minutes. After slowly cooling to room temperature, liquid crystals PA0500 manufactured by DIC Corporation were vacuum-injected into the produced cell using a vacuum injector manufactured by Mikasa Co., Ltd. After the injection, the cell opening was sealed by applying a sealing material 3026B manufactured by 3M and applying ultraviolet rays to the part around the sealing material only using an UV irradiator manufactured by Fujiwara Scientific Co., Ltd.

Wires were attached to the obtained liquid crystal cell and heated at 92° C. for 2 minutes. Then, the VT curve on each electrode was obtained using LCD5200 manufactured by Otsuka Electronics Co., Ltd. Then, stress of 60° C., 60 Hz, 64 hours and 10V was applied to the electrodes in a thermostat chamber manufactured by ESPEC CORP. After the application, the VT curves were obtained again using LCD5200, and the ratio of light transmittances on each electrode at 4V between before and after the stress application was calculated. That is, the value obtained by dividing the transmittance before the application T1 by the transmittance after the application T2 (T1/T2) was defined as the evaluation parameter of AC burn-in. The evaluation parameter is 1 in the ideal state without AC burn-in, and the evaluation parameter becomes greater than 1 when the state differs from the ideal state.

The AC burn-in of the copolymer (p1) was 1.04.

The nematic liquid crystal mixture PA0500 manufactured by DIC Corporation was prepared by mixing the liquid crystal compounds shown in Table 1 in the amounts described in the same table. As a result of thermal analysis of the obtained nematic liquid crystal mixture PA0500, the nematic-isotropic liquid phase transition temperature (clearing point) was 85.6° C. The extraordinary refractive index $n_e$ at a wavelength of 589 nm was 1.596, and the ordinary refractive index $n_o$ at a wavelength of 589 nm was 1.491. The dielectric anisotropy was +7.0, and $K_{22}$ (twist elastic modulus) was 7.4 pN.

TABLE 1

| Liquid Crystal Compound | Mixed Amount (% by mass) |
|---|---|
| 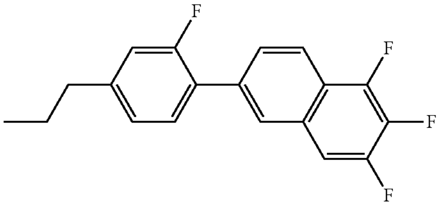 [SMILES: CCCc1ccc(-c2ccc3c(F)c(F)c(F)cc3c2)c(F)c1] | 9 |
| 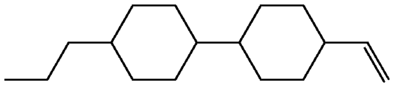 [SMILES: C=CC1CCC(C2CCC(CCC)CC2)CC1] | 37 |
| 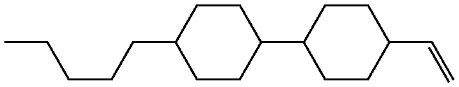 | 2 |
| 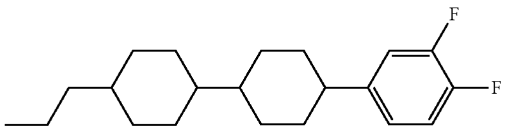 [SMILES: CCCC1CCC(C2CCC(c3ccc(F)c(F)c3)CC2)CC1] | 12 |
| 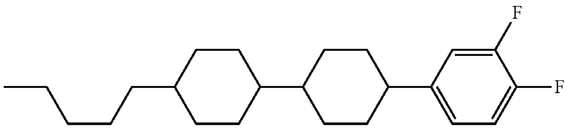 [SMILES: CCCCCC1CCC(C2CCC(c3ccc(F)c(F)c3)CC2)CC1] | 12 |
| 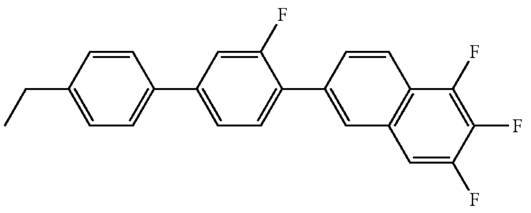 [SMILES: CCc1ccc(-c2ccc(-c3ccc4c(F)c(F)c(F)cc4c3)c(F)c2)cc1] | 4 |

TABLE 1-continued

| Liquid Crystal Compound | Mixed Amount (% by mass) |
|---|---|
| 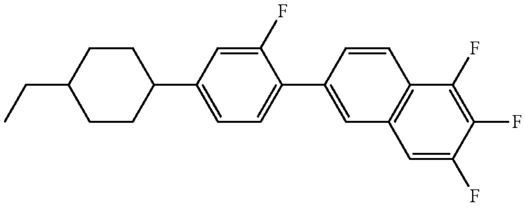 [SMILES: CCC1CCC(c2ccc(-c3ccc4c(F)c(F)c(F)cc4c3)c(F)c2)CC1] | 6 |
| 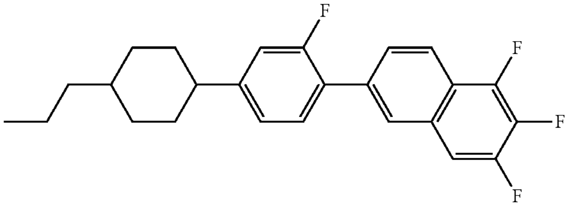 [SMILES: CCCC1CCC(c2ccc(-c3ccc4c(F)c(F)c(F)cc4c3)c(F)c2)CC1] | 13 |
| 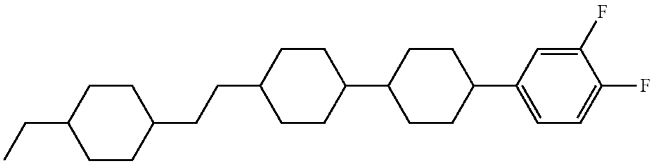 [SMILES: CCC1CCC(CCC2CCC(C3CCC(c4ccc(F)c(F)c4)CC3)CC2)CC1] | 5 |

Examples 2 to 15

By the same method as in Example 1, photo-alignment films and liquid crystal cells were produced using the copolymers (p2) to (p15), and the AC burn-in was measured. The results are shown in Table 2.

Comparative Example 1

By the same method as in Example 1, photo-alignment films and a liquid crystal cell were produced using the copolymer (Ref-p), and the AC burn-in was measured. The results are shown in Table 2.

TABLE 2

| | Example | | | | | | | |
|---|---|---|---|---|---|---|---|---|
| Polymer | p1 | p2 | p3 | p4 | p5 | p6 | p7 | p8 |
| AC burn-in | 1.04 | 1.00 | 1.02 | 1.03 | 1.03 | 1.02 | 1.02 | 1.03 |

| | Example | | | | | | | Comparative Example |
|---|---|---|---|---|---|---|---|---|
| Polymer | p9 | p10 | p11 | p12 | p13 | p14 | p15 | Ref-p |
| AC burn-in | 1.04 | 1.02 | 1.02 | 1.03 | 1.02 | 1.01 | 1.04 | 1.09 |

From the above results, it was confirmed that the AC burn-in of the liquid crystal cells having the photo-alignment films of the Examples according to the invention was reduced. This means that the photo-alignment films of the Examples according to the invention exhibit excellent ability of controlling alignment. Also, because the amount of irradiation with the polarized ultraviolet rays was low when the photo-alignment films were produced, it was found that the photo-alignment polymers of the Examples according to the invention are highly sensitive to polarized ultraviolet rays.

<Preparation of Photo-Alignment Film and Optically Anisotropic Body>

Example 16

Five parts of the copolymer (p1) were dissolved in a mixed solvent of 47.5 parts of N-methyl-2-pyrrolidone and 47.5 parts of 2-butoxyethanol and stirred at room temperature for 10 minutes. Next, the solution was applied onto two glass plates, which were substrates, using a spin coater. Here, on one glass plate of the pair of glass plates, interdigitated array ITO electrodes had been formed with separation distance of 5 μm along the long side of the glass plate. Subsequently, the two glass plates, onto which the solution had been applied, were heated at 80° C. for 3 minutes and further at 180° C. for 5 minutes, and coating films of the copolymer (p1) with thicknesses of about 0.1 μm were obtained. The copolymer (p1) was evenly applied on the glass plates, and flat and smooth films were formed.

Next, ultraviolet light (313 nm, irradiance of 20 mW/cm$^2$) was applied as a parallel ray from an ultra-high-pressure mercury lamp through a wavelength cut filter, a band-pass filter and a polarizing filter to the surfaces of the glass plates on which the coating films had been formed, and photo-alignment films (photo-alignment layers) were obtained. The ultraviolet light applied was linearly polarized light, and the ultraviolet light was applied from the normal line direction to the glass plate surfaces so that the direction of the vibration of the electric field of the linearly polarized light became parallel to the interdigitated array ITO electrodes (the direction of the long side of the glass plates). The irradiation energy of the ultraviolet light was 100 mJ/cm$^2$.

A polymerizable liquid crystal composition (LC-3) containing the liquid crystal compounds shown in Table 3 in the amounts described in the same table was applied onto the photo-alignment films obtained above with a spin coater and dried at 80° C. for one minute, and then ultraviolet rays were applied at 1 J/$cm^2$ in a nitrogen atmosphere to polymerize the polymerizable liquid crystal composition (LC-1). An optically anisotropic body was thus obtained.

The obtained optically anisotropic body was evaluated by the following method. As a result, the alignment was graded A, and excellent alignment could be achieved with a low amount of irradiation of 100 mJ/$cm^2$. The alignment direction was observed and was homogeneous alignment. Moreover, it was found to be possible to give the alignment to the optically anisotropic body of the invention and to regulate the alignment direction thereof with a very low amount of irradiation with ultraviolet rays during its production.

(Evaluation Method of Alignment)

The appearance of the optically anisotropic body was visually examined and further observed with a polarizing microscope, and the optically anisotropic body was graded from A to E below.

A: Uniform alignment was observed visually, and no defects were observed with the polarizing microscope.

B: Although uniform alignment was observed visually, the alignment area observed with the polarizing microscope was 90 to 100%.

C: The visually observed alignment was not as uniform as in A or B, but the alignment area observed with the polarizing microscope was 60 to 90%.

D: Almost no alignment was observed visually, but the alignment area observed with the polarizing microscope was 40 to 60%.

E: No alignment was observed visually, and the alignment area observed with the polarizing microscope was 40% or less.

TABLE 3

| Compound | Mixed Amount (% by mass) |
|---|---|
| 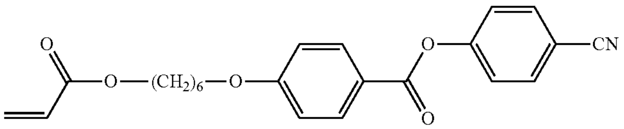 | 25 |
| 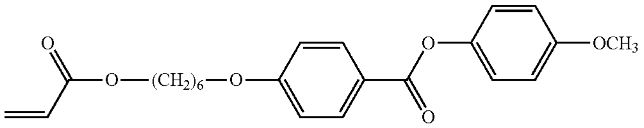 | 25 |
| 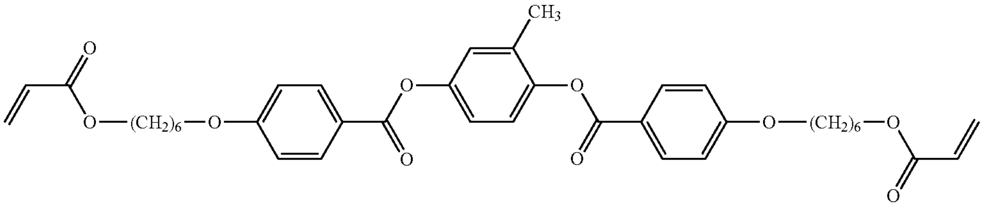 | 10 |
| 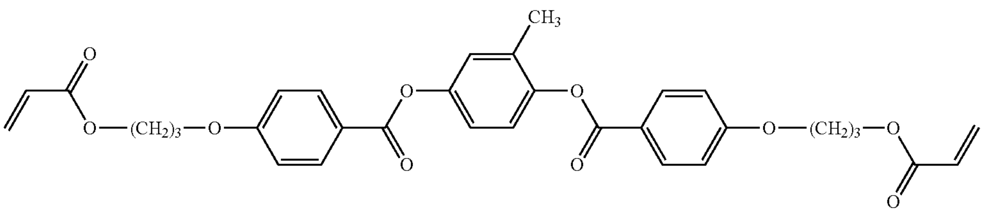 | 38.3 |
| Irgacure 651 (photoinitiator) | 1 |
| Irganox 1076 (stabilizer) | 0.1 |
| Fluorad FC171 | 0.6 |

Examples 17 to 30

Optically anisotropic bodies were obtained in the same manner as in Example 16 except that the copolymers (p2) to (p15) were used, respectively, instead of the copolymer (p1). The obtained optically anisotropic bodies were evaluated by the above method, and as a result, the alignment was graded A. The alignment directions were observed and were homogeneous alignment. Accordingly, optically anisotropic bodies having excellent alignment could be produced with a low amount of irradiation of 100 $mJ/cm^2$ as in Example 16.

Comparative Example 2

An optically anisotropic body was obtained in the same manner as in Example 16 except that the copolymer (Ref-p) was used instead of the copolymer (p1) and that the polymerizable liquid crystal composition (LC-1) was used. The obtained optically anisotropic body was evaluated, and as a result, the alignment was graded B. The alignment direction was observed and was homogeneous alignment.

From the above results, it was found that the optically anisotropic bodies of the Examples according to the invention have excellent alignment. Moreover, because the amount of irradiation with the polarized ultraviolet rays was low when the photo-alignment films constituting the optically anisotropic bodies were formed, it was found that the polymers of the Examples according to the invention are highly sensitive to polarized ultraviolet rays.

INDUSTRIAL APPLICABILITY

The compound and the polymer of the invention can be applied widely in the technical field of liquid crystal display elements.

The invention claimed is:

1. A compound represented by the following formula (1):

(1)

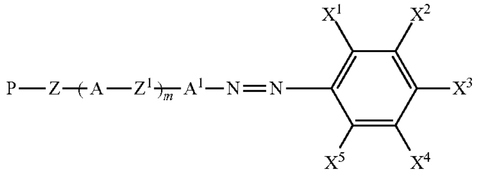

wherein in the formula (1),

P represents a polymerizable group,

A and A' each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, which may be unsubstituted or substituted such that one or more hydrogen atoms in these groups may be substituted with a fluorine atom, a chlorine atom or a linear or branched alkyl group having 1 to 20 carbon atoms wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in the alkyl group having 1 to 20 carbon atoms may be substituted with a fluorine atom, a chlorine atom, a hydroxy group or a cyano group, $X^1$ to $X^5$ each independently represent a hydrogen atom, a fluorine atom, a chlorine atom, a hydroxy group, a nitro group, a cyano group or the following formula (G):

$$-A^2-(Z^2-A^3)_n-R \qquad (G)$$

wherein in the formula (G), $A^2$ and $A^3$ each independently represent a single bond, a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, which may be unsubstituted or substituted such that one or more hydrogen atoms in these groups may be substituted with a fluorine atom, a chlorine atom or a linear or branched alkyl group having 1 to 20 carbon atoms wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in the alkyl group having 1 to 20 carbon atoms may be substituted with a fluorine atom, a chlorine atom, a hydroxy group or a cyano group, $X^1$, $X^2$, $X^4$ and $X^5$ are not simultaneously hydrogen atoms, Z, $Z^1$ and $Z^2$ each independently represent a single bond or a linear or branched alkylene group having 1 to 40 carbon atoms, wherein one or more non-adjacent —$CH_2$—'s in the alkylene group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in —$CH_2$—'s in the alkylene group may be substituted with a fluorine atom, a chlorine atom, a hydroxy group or a cyano group, m and n each independently represent 0 or 1, and R represents a hydrogen atom or a linear or branched alkyl group having 1 to 40 carbon atoms, wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in —$CH_2$—'s in the alkyl group having 1 to 40 carbon atoms may be substituted with a fluorine atom, a chlorine atom, a hydroxy group or a cyano group, with the proviso that R is not a hydrogen atom when n is 0 and $A^2$ is a single bond.

2. The compound according to claim 1, wherein in the formula (1), $X^2$ and $X^4$ do not have any crosslinkable double bond, and at least one of $X^2$ and $X^4$ is not a hydrogen atom when $X^1$, $X^3$ and $X^5$ are simultaneously hydrogen atoms.

3. The compound according to claim 1, wherein one or more of $X^1$ to $X^5$ are a linear or branched alkyl group having 1 to 20 carbon atoms wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in —$CH_2$—'s in the alkyl group having 1 to 20 carbon atoms may be substituted with a fluorine atom, a chlorine atom, a hydroxy group or a cyano group.

4. A cured product obtained by polymerizing the compound according to claim 1.

5. A polymer having one or more kinds of side-chain units represented by the following formula (2):

(2)

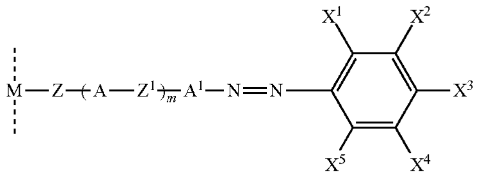

wherein in the formula (2), the broken line represents the main chain of the polymer, M represents a monomer unit of the polymer, A and $A^1$ each independently represent a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, which may be unsubstituted or substituted such that one or more hydrogen atoms in these groups may be substituted with a fluorine atom, a chlorine atom or a linear or branched alkyl group having 1 to 20 carbon atoms wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, —CH═CH—, —C≡C— or —O—CO—O—wherein in the formulae, R's independently represent a hydrogen atom or an alkyl group having 1 to 5 carbon atoms, and one or more hydrogen atoms in the alkyl group having 1 to 20 carbon atoms may be substituted with a fluorine atom, a chlorine atom, a hydroxy group or a cyano group, $X^1$ to $X^5$ each independently represent a hydrogen atom, a fluorine atom, a chlorine atom, a hydroxy group, a nitro group, a cyano group or the following formula (G):

$$-A^2-(Z^2-A^3)_n-R \quad (G)$$

wherein in the formula (G), $A^2$ and $A^3$ each independently represent a single bond, a trans-1,4-cyclohexylene group, a trans-1,3-dioxane-2,5-diyl group, a 1,4-naphthylene group, a 2,6-naphthylene group, a pyridine-2,5-diyl group, a pyrimidine-2,5-diyl group, a 2,5-thiophenylene group, a 2,5-furanylene group or a 1,4-phenylene group, which may be unsubstituted or substituted such that one or more hydrogen atoms in these groups may be substituted with a fluorine atom, a chlorine atom or a linear or branched alkyl group having 1 to 20 carbon atoms wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in the alkyl group having 1 to 20 carbon atoms may be substituted with a fluorine atom, a chlorine atom, a hydroxy group or a cyano group, $X^1$, $X^2$, $X^4$ and $X^5$ are not simultaneously hydrogen atoms, Z, $Z^1$ and $Z^2$ each independently represent a single bond or a linear or branched alkylene group having 1 to 40 carbon atoms, wherein one or more non-adjacent —$CH_2$—'s in the alkylene group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— in the formulae, R's independently represent a hydrogen atom or an alkyl group having 1 to 5 carbon atoms, and one or more hydrogen atoms on —$CH_2$—'s in the alkylene group may be substituted with a fluorine atom, a chlorine atom, a hydroxy group or a cyano group, m and n each independently represent 0 or 1, and R represents a hydrogen atom or a linear or branched alkyl group having 1 to 40 carbon atoms, wherein one or more non-adjacent —$CH_2$—'s in the alkyl group may be independently substituted with —O—, —COO—, —OCO—, —CH═CH—, —CF═CF—, —$CF_2O$—, —$OCF_2$—, —$CF_2CF_2$—, —C≡C—, —CO—, —S—, —$Si(CH_3)_2$—O—$Si(CH_3)_2$—, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms on —$CH_2$—'s in the alkyl group having 1 to 40 carbon atoms may be substituted with a fluorine atom, a chlorine atom, a hydroxy group or a cyano group, with the proviso that R is not a hydrogen atom when n is 0 and $A^2$ is a single bond.

6. The polymer according to claim 5, wherein at least one of $X^2$ and $X^4$ is a fluorine atom, a chlorine atom, a hydroxy group, a nitro group, a cyano group or a group represented by the formula (G).

7. The polymer according to claim 6, wherein at least one of $X^2$ and $X^4$ is a group represented by the formula (G).

8. The polymer according to claim 5, wherein at least one of $X^1$ to $X^5$ is a linear or branched alkyl group having 1 to 20 carbon atoms wherein one or more non-adjacent $—CH_2—$'s in the alkyl group may be independently substituted with —O—, —COO—, —OCO—, —CH═—, —CF═—, $—CF_2O—$, $—OCF_2—$, $—CF_2CF_2—$, —C═—, —CO—, —S—, $—Si(CH_3)_2—O—Si(CH_3)_2—$, —NR'—, —NR'—CO—, —CO—NR'—, —NR'—CO—O—, —O—CO—NR'—, —NR'—CO—NR'—, or —O—CO—O— wherein in the formulae, R's independently represent a hydrogen atom or an alkyl group having 1 to 5 carbon atoms, and one or more hydrogen atoms in the alkyl group having 1 to 20 carbon atoms may be substituted with a fluorine atom, a chlorine atom, a hydroxy group or a cyano group.

9. The polymer according to claim 8, wherein at least one of $X^1$ to $X^5$ is a linear or branched alkyl group having 1 to 5 carbon atoms.

10. The polymer according to claim 9, wherein at least one of $X^2$ and $X^4$ is a linear or branched alkyl group having 1 to 5 carbon atoms.

11. The polymer according to claim 5, wherein M is a monomer unit constituting at least one polymer main chain selected from the group consisting of polyolefins, polyethers, polyamides, polyesters, polycarbonates and polysiloxanes.

12. The polymer according to claim 11, wherein M is a monomer unit constituting at least one polymer main chain selected from polymethacrylate and polyacrylate.

13. The polymer according to claim 5, which is a copolymer.

14. The polymer according to claim 13, which is a copolymer with a side-chain unit having a photochemically crosslinkable site.

15. The polymer according to claim 14, wherein the photochemically crosslinkable site contains one or more structures represented by the following formulae (II-1) to (II-8):

(II-1)

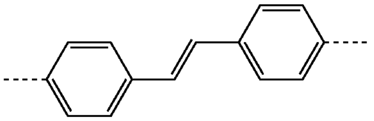

(II-2)

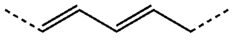

(II-3)

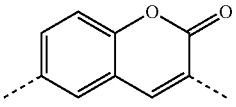

(II-4)

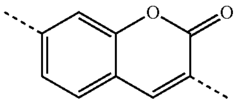

-continued (II-5)

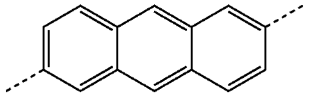

(II-6)

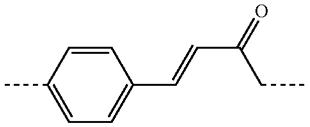

(II-7)

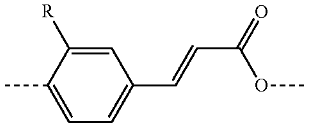

(II-8)

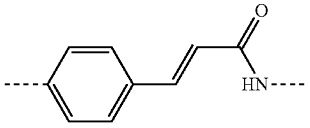

wherein in the formula, R represents a hydrogen atom or a linear or branched alkyl group having 1 to 9 carbon atoms, provided that one or more non-adjacent $—CH_2—$'s in the alkyl group may be independently substituted with —O—, —COO— or —OCO—.

16. The polymer according to claim 14, wherein the side-chain unit having a photochemically crosslinkable site is represented by the following formula (3):

(3)

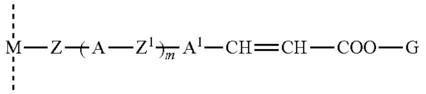

wherein in the formula (3), the broken line represents the main chain of the polymer, M represents a monomer unit of the polymer, G has the same meanings as the formula (G), but is selected independently of that in the formula (2), and Z, $Z^1$, A, $A^1$ and m have the same meanings as those in the formula (2) but are selected independently of those in the formula (2).

17. The polymer according to claim 13, which is a copolymer with a side-chain unit having no photochemically crosslinkable site that is different from the side-chain unit represented by the formula (2).

18. The polymer according to claim 17, wherein the side-chain unit having no crosslinkable site has any functional group selected from a cyano group, a carbonyl group, a hydroxyl group, an amide group, an ether group, an ester group, a thiol group, a sulfonic group, a nitro group and an acetyl group.

19. A photo-alignment film comprising of the compound according to claim 1.

20. An optically anisotropic body comprising the photo-alignment film according to claim 19.

21. A liquid crystal display element comprising the photo-alignment film according to claim 19.

* * * * *